US010544163B2

(12) United States Patent
Kudo et al.

(10) Patent No.: US 10,544,163 B2
(45) Date of Patent: Jan. 28, 2020

(54) CONDENSED HETEROCYCLIC COMPOUNDS AND PESTICIDES

(71) Applicant: Nissan Chemical Corporation, Chuo-ku (JP)

(72) Inventors: Takao Kudo, Funabashi (JP); Keisuke Tsuji, Funabashi (JP); Kenkichi Noto, Funabashi (JP); Yukihiro Maizuru, Funabashi (JP); Hiroto Matsui, Shiraoka (JP); Masaki Kobayashi, Shiraoka (JP); Hotaka Imanaka, Shiraoka (JP)

(73) Assignee: Nissan Chemical Corporation, Chuo-ku (JP)

( * ) Notice: Subject to any disclaimer, the term of this patent is extended or adjusted under 35 U.S.C. 154(b) by 0 days.

(21) Appl. No.: 16/083,079

(22) PCT Filed: Mar. 10, 2017

(86) PCT No.: PCT/JP2017/009763
§ 371 (c)(1),
(2) Date: Sep. 7, 2018

(87) PCT Pub. No.: WO2017/155103
PCT Pub. Date: Sep. 14, 2017

(65) Prior Publication Data
US 2019/0062344 A1  Feb. 28, 2019

(30) Foreign Application Priority Data

Mar. 10, 2016 (JP) .................................. 2016-047064
Mar. 17, 2016 (JP) .................................. 2016-054191
(Continued)

(51) Int. Cl.
*C07D 513/04* (2006.01)
*C07D 471/04* (2006.01)
(Continued)

(52) U.S. Cl.
CPC ........... *C07D 513/04* (2013.01); *A01N 43/90* (2013.01); *A61K 31/437* (2013.01); *C07D 471/04* (2013.01); *C07D 487/04* (2013.01)

(58) Field of Classification Search
CPC .. C07D 513/04; C07D 471/04; C07D 487/04; A01N 43/90; A61K 31/437
See application file for complete search history.

(56) References Cited

U.S. PATENT DOCUMENTS

2012/0196891 A1  8/2012 Iwakoshi
2013/0090353 A1  4/2013 Iwakoshi et al.
(Continued)

FOREIGN PATENT DOCUMENTS

EP  2 274 983 A1  1/2011
EP  2 955 178 A1  12/2015
(Continued)

OTHER PUBLICATIONS

International Search Report dated May 23, 2017, in PCT/JP2017/009763, filed Mar. 10, 2017.

*Primary Examiner* — Timothy R Rozof
(74) *Attorney, Agent, or Firm* — Oblon, McClelland, Maier & Neustadt, L.L.P.

(57) ABSTRACT

To provide novel pesticides, especially insecticides or acaricides.
A condensed heterocyclic compound represented by the formula (1) or its salt, or N-oxide thereof:

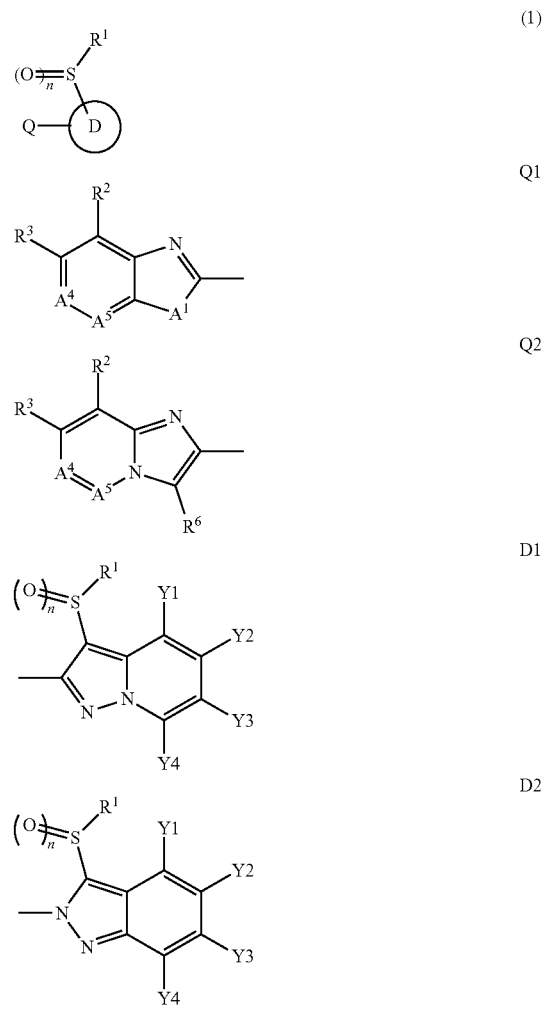

wherein Q is a structure represented by Q1, Q2 or the like, D substituted with —S(O)$_n$R$^1$ is a structure represented by
(Continued)

D1 or D2, $A^1$ is $N(A^{1\ a})$ or the like, $A^{1\ a}$ is $C_1$-$C_6$ alkyl or the like, $A^4$ is a nitrogen atom or $C(R^4)$, $A^5$ is a nitrogen atom or $C(R^5)$, $R^1$ is $C_1$-$C_6$ alkyl or the like, each of $R^2$, $R^5$ and $R^6$ is independently a hydrogen atom or $C_1$-$C_6$ alkyl, each of $R^3$, $R^4$, Y1, Y2, Y3 and Y4 is independently a halogen atom, halo ($C_1$-$C_6$) alkyl or the like, and n is an integer of 0, 1 or 2.

11 Claims, No Drawings

(30) Foreign Application Priority Data

| | | |
|---|---|---|
| Oct. 7, 2016 | (JP) | 2016-199515 |
| Dec. 28, 2016 | (JP) | 2016-255131 |

(51) Int. Cl.

| | |
|---|---|
| *C07D 487/04* | (2006.01) |
| *A01N 43/90* | (2006.01) |
| *A61K 31/473* | (2006.01) |
| *A61K 31/437* | (2006.01) |

(56) References Cited

U.S. PATENT DOCUMENTS

| | | |
|---|---|---|
| 2013/0252981 A1 | 9/2013 | Takahashi et al. |
| 2015/0094329 A1 | 4/2015 | Nokura et al. |
| 2015/0166573 A1 | 6/2015 | Takahashi et al. |
| 2015/0181880 A1 | 7/2015 | Takahashi et al. |
| 2015/0191474 A1 | 7/2015 | Takahashi et al. |
| 2015/0246911 A1 | 9/2015 | Takahashi et al. |
| 2015/0313234 A1 | 11/2015 | Takahashi et al. |
| 2015/0373982 A1 | 12/2015 | Takahashi et al. |
| 2016/0002260 A1 | 1/2016 | Tanabe et al. |
| 2016/0021886 A1 | 1/2016 | Yonemura et al. |
| 2016/0227779 A1 | 8/2016 | Alig et al. |
| 2016/0255837 A1 | 9/2016 | Edmunds et al. |
| 2016/0368915 A1 | 12/2016 | Tanabe et al. |
| 2017/0073342 A1 | 3/2017 | Fischer et al. |
| 2017/0135348 A1 | 5/2017 | Tanabe et al. |
| 2018/0022760 A1 | 1/2018 | Kudo et al. |

FOREIGN PATENT DOCUMENTS

| | | |
|---|---|---|
| EP | 2 955 179 A1 | 12/2015 |
| EP | 2 963 022 A1 | 1/2016 |
| EP | 3 241 830 A1 | 11/2017 |
| JP | 2017-186327 A | 10/2017 |
| JP | 2018-24657 A | 2/2018 |
| JP | 2018-24658 A | 2/2018 |
| JP | 2018-27943 A | 2/2018 |
| JP | 2018-30834 A | 3/2018 |
| JP | 2018-43953 A | 3/2018 |
| JP | 2018-70585 A | 5/2018 |
| WO | WO 2009/131237 A1 | 10/2009 |
| WO | WO 2010/125985 A1 | 11/2010 |
| WO | WO 2011/043404 A1 | 4/2011 |
| WO | WO 2011/162364 A1 | 12/2011 |
| WO | WO 2012/074135 A1 | 6/2012 |
| WO | WO 2012/086848 A1 | 6/2012 |
| WO | WO 2013/018928 A1 | 2/2013 |
| WO | WO 2013/180193 A1 | 12/2013 |
| WO | WO 2013/180194 A1 | 12/2013 |
| WO | WO 2013/191112 A1 | 12/2013 |
| WO | WO 2013/191113 A1 | 12/2013 |
| WO | WO 2013/191188 A1 | 12/2013 |
| WO | WO 2013/191189 A1 | 12/2013 |
| WO | WO 2014/104407 A1 | 7/2014 |
| WO | WO 2014/123205 A1 | 8/2014 |
| WO | WO 2014/123206 A1 | 8/2014 |
| WO | WO 2014/132971 A1 | 9/2014 |
| WO | WO 2014/132972 A1 | 9/2014 |
| WO | WO 2014/142292 A1 | 9/2014 |
| WO | WO 2014/148451 A1 | 9/2014 |
| WO | WO 2014/157600 A1 | 10/2014 |
| WO | WO 2015/000715 A1 | 1/2015 |
| WO | WO 2015/002211 A1 | 1/2015 |
| WO | WO 2015/059088 A1 | 4/2015 |
| WO | WO 2015/071180 A1 | 5/2015 |
| WO | WO 2015/087458 A1 | 6/2015 |
| WO | WO 2015/091945 A1 | 6/2015 |
| WO | WO 2015/121136 A1 | 8/2015 |
| WO | WO 2015/133603 A1 | 9/2015 |
| WO | WO 2015/198859 A1 | 12/2015 |
| WO | WO 2016/005263 A1 | 1/2016 |
| WO | WO 2016/091731 A1 | 6/2016 |
| WO | WO 2016/107742 A1 | 7/2016 |
| WO | WO 2016/129684 A1 | 8/2016 |
| WO | WO 2016/142326 A1 | 9/2016 |
| WO | WO 2016/142327 A1 | 9/2016 |
| WO | WO 2016/162318 A1 | 10/2016 |
| WO | WO 2017/001311 A1 | 1/2017 |
| WO | WO 2017/026384 A1 | 2/2017 |
| WO | WO 2017/061497 A1 | 4/2017 |
| WO | WO 2017/072039 A1 | 5/2017 |
| WO | WO 2017/077968 A1 | 5/2017 |
| WO | WO 2017/093180 A1 | 6/2017 |
| WO | WO 2017/125340 A1 | 7/2017 |
| WO | WO 2017/133994 A1 | 8/2017 |
| WO | WO 2017/144341 A1 | 8/2017 |
| WO | WO 2017/146220 A1 | 8/2017 |
| WO | WO 2017/155103 A1 | 9/2017 |
| WO | WO 2017/174414 A1 | 10/2017 |
| WO | WO 2017/174449 A1 | 10/2017 |
| WO | WO 2018/003976 A1 | 1/2018 |
| WO | WO 2018/015289 A1 | 1/2018 |
| WO | WO 2018/033455 A1 | 2/2018 |
| WO | WO 2018/043597 A1 | 3/2018 |
| WO | WO 2018/050825 A1 | 3/2018 |
| WO | WO 2018/052119 A1 | 3/2018 |
| WO | WO 2018/052136 A1 | 3/2018 |
| WO | WO 2018/070503 A1 | 4/2018 |
| WO | WO 2018/084141 A1 | 5/2018 |
| WO | WO 2018/084142 A1 | 5/2018 |
| WO | WO 2018/095953 A1 | 5/2018 |
| WO | WO 2018/105632 A1 | 6/2018 |

CONDENSED HETEROCYCLIC COMPOUNDS AND PESTICIDES

TECHNICAL FIELD

The present invention relates to a novel condensed heterocyclic compound and its salt, and a pesticide containing the compound as an active ingredient.

BACKGROUND ART

Patent Documents 1 to 31 disclose various condensed heterocyclic compounds, however, they failed to disclose the condensed heterocyclic compounds of the present invention. Usefulness of the condensed heterocyclic compounds of the present invention as pesticides, especially, as insecticides, acaricides or parasiticides against internal or external parasites in or on a mammal, fish or bird is not disclosed at all.

PRIOR ART DOCUMENTS

Patent Documents

Patent Document 1: WO2016/005263
Patent Document 2: WO2015/198859
Patent Document 3: WO2015/133603
Patent Document 4: WO2015/121136
Patent Document 5: WO2015/091945
Patent Document 6: WO2015/087458
Patent Document 7: WO2015/071180
Patent Document 8: WO2015/059088
Patent Document 9: WO2015/002211
Patent Document 10: WO2015/000715
Patent Document 11: WO2014/157600
Patent Document 12: WO2014/148451
Patent Document 13: WO2014/142292
Patent Document 14: WO2014/132972
Patent Document 15: WO2014/132971
Patent Document 16: WO2014/123206
Patent Document 17: WO2014/123205
Patent Document 18: WO2014/104407
Patent Document 19: WO2013/180194
Patent Document 20: WO2013/180193
Patent Document 21: WO2013/191113
Patent Document 22: WO2013/191189
Patent Document 23: WO2013/191112
Patent Document 24: WO2013/191188
Patent Document 25: WO2013/018928
Patent Document 26: WO2012/086848
Patent Document 27: WO2012/074135
Patent Document 28: WO2011/162364
Patent Document 29: WO2011/043404
Patent Document 30: WO2010/125985
Patent Document 31: WO2009/131237

DISCLOSURE OF INVENTION

Technical Problem

With the advance of development of pesticides targeted at various pest insects such as agricultural pest insects, forest pest insects or hygienic pest insects, various pesticides have been put into practical use.

However, recently, control of pest insects with conventional insecticides or fungicides has become difficult in more and more cases, as pest insects acquire resistance to them over many years of their use. Problems of the high toxicity of some conventional pesticides and of the disturbance of the ecosystem by some conventional pesticides which remain in the environment for a long period are becoming apparent. Under these circumstances, development of novel pesticides with high pesticidal activity, low toxicity and low persistence is always expected.

It is an object of the present invention to provide a novel pesticide which has excellent pesticidal activities, which has low toxicity, for example, which has little harmful effect on non-target organisms such as mammals, fishes and useful insects, and which has low persistence.

Solution to Problems

The present inventors have conducted extensive studies to achieve the above object and as a result, found that a novel condensed heterocyclic compound represented by the following formula (1) of the present invention is a very useful compound which has excellent pesticidal activities particularly insecticidal and acaricidal activities, and which has little harmful effect on non-target organisms such as mammals, fishes and useful insects, and accomplished the present invention.

That is, the present invention relates to the following [1] to [95].

[1] A condensed heterocyclic compound represented by the formula (1) or its salt, or N-oxide thereof:

wherein Q is a structure represented by Q1, Q2, Q3, Q4, Q5 or Q6:

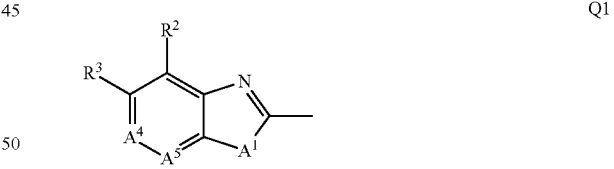

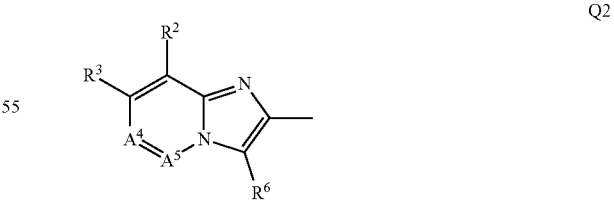

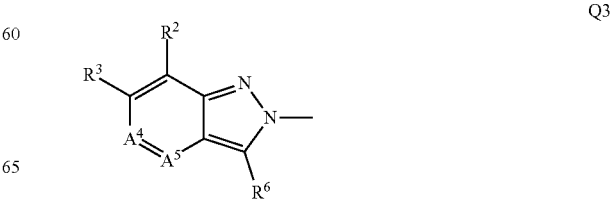

-continued

Q4
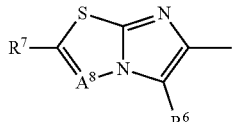

Q5
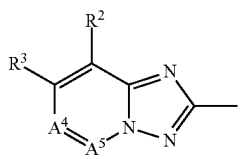

Q6
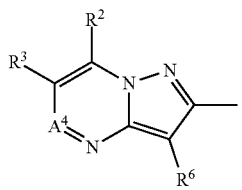

D substituted with —S(O)$_n$R$^1$ is a structure represented by D1 or D2:

D1
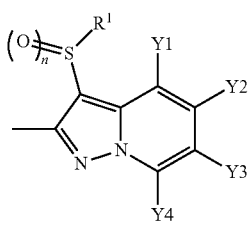

D2
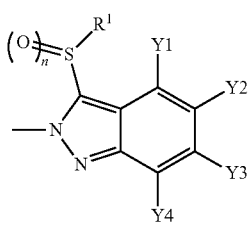

A$^1$ is N(A$^{1\ a}$), an oxygen atom or a sulfur atom,
A$^4$ is a nitrogen atom or C(R$^4$),
A$^5$ is a nitrogen atom or C(R$^5$),
A$^8$ is a nitrogen atom or C(R$^8$),
R$^1$ is C$_1$-C$_6$ alkyl or halo (C$_1$-C$_6$) alkyl,
each of R$^2$, R$^5$, R$^6$ and R$^8$ is independently a hydrogen atom or C$_1$-C$_6$ alkyl,
each of R$^3$, R$^4$ and R$^7$ is independently a hydrogen atom, a halogen atom, halo (C$_1$-C$_6$) alkyl, halo (C$_1$-C$_6$) alkylthio, halo (C$_1$-C$_6$) alkylsulfinyl or halo (C$_1$-C$_6$) alkylsulfonyl,
each of Y1, Y2, Y3 and Y4 is independently a hydrogen atom, a halogen atom, C$_3$-C$_6$ cycloalkyl, (C$_3$-C$_6$) cycloalkyl optionally substituted with Y$^a$, C$_1$-C$_6$ alkyl, halo (C$_1$-C$_6$) alkyl, C$_1$-C$_6$ alkoxy, halo (C$_1$-C$_6$) alkoxy, C$_1$-C$_6$ alkylthio, halo (C$_1$-C$_6$) alkylthio, C$_1$-C$_6$ alkylsulfinyl, halo (C$_1$-C$_6$) alkylsulfinyl, C$_1$-C$_6$ alkylsulfonyl, halo (C$_1$-C$_6$) alkylsulfonyl, —NH$_2$, —NHR$^{9\ o\ g}$, cyano, nitro, G1 or G2,
R$^{9\ o\ g}$ is C$_1$-C$_6$ alkyl, halo (C$_1$-C$_6$) alkyl, C$_1$-C$_6$ alkylcarbonyl, halo (C$_1$-C$_6$) alkylcarbonyl, C$_1$-C$_6$ alkoxycarbonyl, halo (C$_1$-C$_6$) alkoxycarbonyl, C$_1$-C$_6$ alkylsulfonyl or halo (C$_1$-C$_6$) alkylsulfonyl, G1 is a structure represented by G1-1, G1-2, G1-3 or G1-4:

G1-1
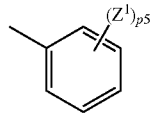

G1-2
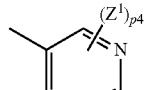

G1-3
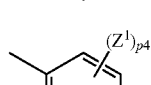

G1-4
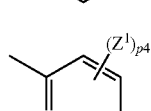

G2 is a structure represented by G2-1, G2-2, G2-3 or G2-4,

G2-1

G2-2
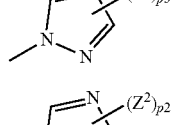

G2-3
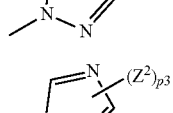

G2-4

A$^{1\ a}$ is a hydrogen atom or C$_1$-C$_6$ alkyl,
each of Z$^1$ and Z$^2$ is independently a halogen atom, C$_1$-C$_6$ alkyl, halo (C$_1$-C$_6$) alkyl, C$_1$-C$_6$ alkoxy, halo (C$_1$-C$_6$) alkoxy, C$_1$-C$_6$ alkylthio, halo (C$_1$-C$_6$) alkylthio, C$_1$-C$_6$ alkylsulfinyl, halo (C$_1$-C$_6$) alkylsulfinyl, C$_1$-C$_6$ alkylsulfonyl, halo (C$_1$-C$_6$) alkylsulfonyl, cyano or nitro, when p2, p3, p4 or p5 is an integer of at least 2, each of Z$^1$ and Z$^2$ may be identical with or different from one another,
Y$^a$ is cyano, —C(O)OH or —C(O)NH$_2$,
p2 is an integer of 0, 1 or 2,
p3 is an integer of 0, 1, 2 or 3,
p4 is an integer of 0, 1, 2, 3 or 4,
p5 is an integer of 0, 1, 2, 3, 4 or 5, and
n is an integer of 0, 1 or 2.

[2] The condensed heterocyclic compound or its salt, or N-oxide thereof according to the above [1], wherein the formula (1) is represented by the formula (1-1):

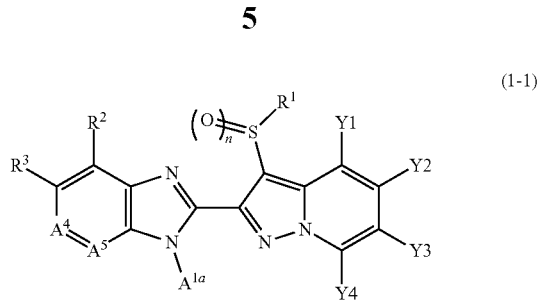

(1-1)

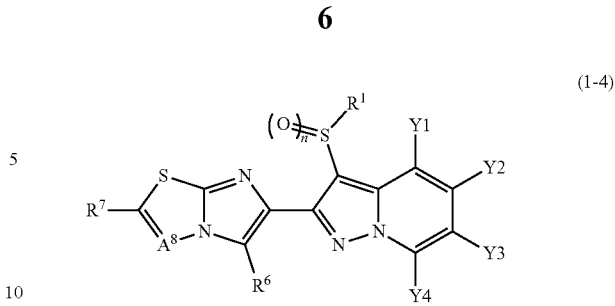

(1-4)

wherein $R^1$ is $C_1$-$C_6$ alkyl, and $A^{1a}$ is $C_1$-$C_6$ alkyl.

[3] The condensed heterocyclic compound or its salt, or N-oxide thereof according to the above [2], wherein each of $R^2$, $R^4$ and $R^5$ is a hydrogen atom, $R^3$ is halo ($C_1$-$C_6$) alkyl, halo ($C_1$-$C_6$) alkylthio, halo ($C_1$-$C_6$) alkylsulfinyl or halo ($C_1$-$C_6$) alkylsulfonyl, Y1 is a hydrogen atom or a halogen atom, and each of Y2, Y3 and Y4 is independently a hydrogen atom, a halogen atom, halo ($C_1$-$C_6$) alkyl, $C_1$-$C_6$ alkylthio, $C_1$-$C_6$ alkylsulfinyl, $C_1$-$C_6$ alkylsulfonyl, G1 or G2.

[4] The condensed heterocyclic compound or its salt, or N-oxide thereof according to the above [3], wherein $A^4$ is $C(R^4)$, $A^5$ is a nitrogen atom, $R^3$ is halo ($C_1$-$C_6$) alkyl, halo ($C_1$-$C_6$) alkylthio or halo ($C_1$-$C_6$) alkylsulfinyl, Y2 is a hydrogen atom, a halogen atom, halo ($C_1$-$C_6$) alkyl, $C_1$-$C_6$ alkylthio, $C_1$-$C_6$ alkylsulfinyl, $C_1$-$C_6$ alkylsulfonyl or G1, Y3 is a hydrogen atom, a halogen atom, halo ($C_1$-$C_6$) alkyl or G2, Y4 is a hydrogen atom, G1 is G1-1, G2 is G2-2, $Z^2$ is halo ($C_1$-$C_6$) alkyl, p3 is an integer of 1, p5 is an integer of 0, and n is an integer of 0 or 2.

[5] The condensed heterocyclic compound or its salt, or N-oxide thereof according to the above [3], wherein $A^4$ is a nitrogen atom, $A^5$ is $C(R^5)$, $R^3$ is halo ($C_1$-$C_6$) alkyl, Y3 is a hydrogen atom or a halogen atom, each of Y2 and Y4 is a hydrogen atom, and n is an integer of 0 or 2.

[6] The condensed heterocyclic compound or its salt, or N-oxide thereof according to the above [1], wherein the formula (1) is represented by the formula (1-3):

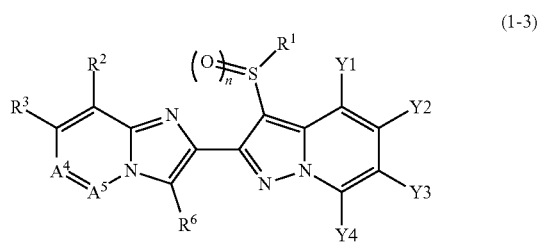

(1-3)

wherein $A^4$ is a nitrogen atom, $A^5$ is $C(R^5)$, $R^1$ is $C_1$-$C_6$ alkyl, each of $R^2$ and $R^5$ is a hydrogen atom, $R^3$ is halo ($C_1$-$C_6$) alkyl, Y1 is a hydrogen atom or a halogen atom, each of Y2, Y3 and Y4 is independently a hydrogen atom, a halogen atom, halo ($C_1$-$C_6$) alkyl, $C_1$-$C_6$ alkylthio, $C_1$-$C_6$ alkylsulfinyl, $C_1$-$C_6$ alkylsulfonyl, G1 or G2.

[7] The condensed heterocyclic compound or its salt, or N-oxide thereof according to the above [6], wherein $R^6$ is a hydrogen atom, each of Y1, Y3 and Y4 is a hydrogen atom, Y2 is halo ($C_1$-$C_6$) alkyl, and n is an integer of 2.

[8] The condensed heterocyclic compound or its salt, or N-oxide thereof according to the above [1], wherein the formula (1) is represented by the formula (1-4):

wherein $A^8$ is a nitrogen atom, $R^1$ is $C_1$-$C_6$ alkyl, $R^7$ is halo ($C_1$-$C_6$) alkyl, Y1 is a hydrogen atom or a halogen atom, each of Y2, Y3 and Y4 is independently a hydrogen atom, a halogen atom, halo ($C_1$-$C_6$) alkyl, $C_1$-$C_6$ alkylthio, $C_1$-$C_6$ alkylsulfinyl, $C_1$-$C_6$ alkylsulfonyl, G1 or G2.

[9] The condensed heterocyclic compound or its salt, or N-oxide thereof according to the above [8], wherein $R^6$ is a hydrogen atom, each of Y1, Y3 and Y4 is a hydrogen atom, Y2 is halo ($C_1$-$C_6$) alkyl, and n is an integer of 2.

[10] The condensed heterocyclic compound or its salt, or N-oxide thereof according to the above [1], wherein the formula (1) is represented by the formula (1-2):

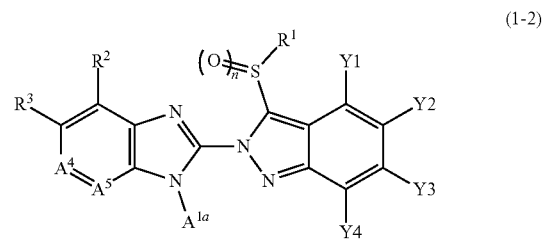

(1-2)

wherein $R^1$ is $C_1$-$C_6$ alkyl, and $A^{1a}$ is $C_1$-$C_6$ alkyl.

[11] The condensed heterocyclic compound or its salt, or N-oxide thereof according to the above [10], wherein $A^4$ is $C(R^4)$, $A^5$ is a nitrogen atom, $R^3$ is halo ($C_1$-$C_6$) alkyl, Y3 is a halogen atom, halo ($C_1$-$C_6$) alkyl, —$NH_2$ or nitro, each of $R^2$, $R^4$, Y1, Y2 and Y4 is a hydrogen atom, and n is an integer of 0 or 2.

[12] The condensed heterocyclic compound or its salt, or N-oxide thereof according to the above [10], wherein $A^4$ is a nitrogen atom, $A^5$ is $C(R^5)$, each of $R^3$ and Y3 is independently halo ($C_1$-$C_6$) alkyl, each of $R^2$, $R^5$, Y1, Y2 and Y4 is a hydrogen atom, and n is an integer of 0 or 2.

[13] The condensed heterocyclic compound or its salt, or N-oxide thereof according to the above [1], wherein the formula (1) is represented by the formula (1-6):

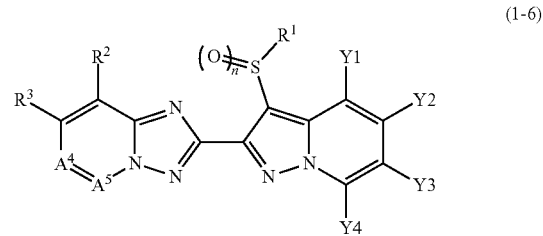

(1-6)

wherein $A^4$ is $C(R^4)$, $A^5$ is $C(R^5)$, $R^1$ is $C_1$-$C_6$ alkyl, each of $R^2$, $R^4$ and $R^5$ is a hydrogen atom, $R^3$ is halo ($C_1$-$C_6$) alkyl, Y1 is a hydrogen atom or a halogen atom, each of Y2, Y3 and Y4 is independently a hydrogen atom, a halogen atom, halo ($C_1$-$C_6$) alkyl, $C_1$-$C_6$ alkylthio, $C_1$-$C_6$ alkylsulfinyl, $C_1$-$C_6$ alkylsulfonyl, G1 or G2.

[14] The condensed heterocyclic compound or its salt, or N-oxide thereof according to the above [13], wherein each of Y1, Y3 and Y4 is a hydrogen atom, Y2 is halo ($C_1$-$C_6$) alkyl, and n is an integer of 0 or 2.

[15] The condensed heterocyclic compound or its salt, or N-oxide thereof according to the above [1], wherein Q is a structure represented by Q1, and D substituted with —S(O)$_n$R$^1$ is D1.

[16] The condensed heterocyclic compound or its salt, or N-oxide thereof according to the above [1], wherein Q is a structure represented by Q2, and D substituted with —S(O)$_n$R$^1$ is D1.

[17] The condensed heterocyclic compound or its salt, or N-oxide thereof according to the above [1], wherein Q is a structure represented by Q3, and D substituted with —S(O)$_n$R$^1$ is D1.

[18] The condensed heterocyclic compound or its salt, or N-oxide thereof according to the above [1], wherein Q is a structure represented by Q4, and D substituted with —S(O)$_n$R$^1$ is D1.

[19] The condensed heterocyclic compound or its salt, or N-oxide thereof according to the above [1], wherein Q is a structure represented by Q5, and D substituted with —S(O)$_n$R$^1$ is D1.

[20] The condensed heterocyclic compound or its salt, or N-oxide thereof according to the above [1], wherein Q is a structure represented by Q6, and D substituted with —S(O)$_n$R$^1$ is D1.

[21] The condensed heterocyclic compound or its salt, or N-oxide thereof according to the above [1], wherein Q is a structure represented by Q1, and D substituted with —S(O)$_n$R$^1$ is D2.

[22] The condensed heterocyclic compound or its salt, or N-oxide thereof according to the above [1], [15] or [21], wherein A$^1$ is N(A$^{1\ a}$).

[23] The condensed heterocyclic compound or its salt, or N-oxide thereof according to the above [1], [15] or [21], wherein A$^1$ is an oxygen atom or a sulfur atom.

[24] The condensed heterocyclic compound or its salt, or N-oxide thereof according to any one of the above [1] to [3], [10], [15] to [17], [19] and [21], wherein A$^4$ is a nitrogen atom, and A$^5$ is a nitrogen atom.

[25] The condensed heterocyclic compound or its salt, or N-oxide thereof according to any one of the above [1] to [3], [10], [15] to [17], [19] and [21], wherein A$^4$ is C(R$^4$), and A$^5$ is C(R$^5$).

[26] The condensed heterocyclic compound or its salt, or N-oxide thereof according to any one of the above [1] to [3], [10], [15] to [17], [19] and [21], wherein A$^4$ is a nitrogen atom, and A$^5$ is C(R$^5$).

[27] The condensed heterocyclic compound or its salt, or N-oxide thereof according to any one of the above [1] to [3], [10], [15] to [17], [19] and [21], wherein A$^4$ is C(R$^4$), and A$^5$ is a nitrogen atom.

[28] The condensed heterocyclic compound or its salt, or N-oxide thereof according to the above [1] or [20], wherein A$^4$ is C(R$^4$).

[29] The condensed heterocyclic compound or its salt, or N-oxide thereof according to the above [1] or [20], wherein A$^4$ is a nitrogen atom.

[30] The condensed heterocyclic compound or its salt, or N-oxide thereof according to the above [1] or [18], wherein A$^8$ is a nitrogen atom.

[31] The condensed heterocyclic compound or its salt, or N-oxide thereof according to the above [1] or [18], wherein A$^8$ is C(R$^8$).

[32] The condensed heterocyclic compound or its salt, or N-oxide thereof according to any one of the above [1] to [31], wherein R$^1$ is $C_1$-$C_6$ alkyl.

[33] The condensed heterocyclic compound or its salt, or N-oxide thereof according to any one of the above [1] to [31], wherein R$^1$ is halo ($C_1$-$C_6$) alkyl.

[34] The condensed heterocyclic compound or its salt, or N-oxide thereof according to any one of the above [1] to [33], wherein each of R$^2$, R$^5$, R$^6$ and R$^8$ is independently a hydrogen atom or $C_1$-$C_6$ alkyl.

[35] The condensed heterocyclic compound or its salt, or N-oxide thereof according to any one of the above [1] to [34], wherein each of R$^3$, R$^4$ and R$^7$ is independently a hydrogen atom, a halogen atom, halo ($C_1$-$C_6$) alkyl, halo ($C_1$-$C_6$) alkylthio, halo ($C_1$-$C_6$) alkylsulfinyl or halo ($C_1$-$C_6$) alkylsulfonyl.

[36] The condensed heterocyclic compound or its salt, or N-oxide thereof according to any one of the above [1] to [35], wherein R$^3$ is a hydrogen atom, a halogen atom or halo ($C_1$-$C_6$) alkyl.

[37] The condensed heterocyclic compound or its salt, or N-oxide thereof according to any one of the above [1] to [35], wherein R$^3$ is halo ($C_1$-$C_6$) alkyl.

[38] The condensed heterocyclic compound or its salt, or N-oxide thereof according to any one of the above [1] to [35], wherein R$^3$ is halo ($C_1$-$C_6$) alkylthio, halo ($C_1$-$C_6$) alkylsulfinyl or halo ($C_1$-$C_6$) alkylsulfonyl.

[39] The condensed heterocyclic compound or its salt, or N-oxide thereof according to any one of the above [1] to [38], wherein R$^4$ is a hydrogen atom, a halogen atom or halo ($C_1$-$C_6$) alkyl.

[40] The condensed heterocyclic compound or its salt, or N-oxide thereof according to any one of the above [1] to [38], wherein R$^4$ is a hydrogen atom or halo ($C_1$-$C_6$) alkyl.

[41] The condensed heterocyclic compound or its salt, or N-oxide thereof according to any one of the above [1] to [38], wherein R$^4$ is a hydrogen atom, halo ($C_1$-$C_6$) alkylthio, halo ($C_1$-$C_6$) alkylsulfinyl or halo ($C_1$-$C_6$) alkylsulfonyl.

[42] The condensed heterocyclic compound or its salt, or N-oxide thereof according to any one of the above [1] to [41], wherein R$^7$ is a hydrogen atom, a halogen atom or halo ($C_1$-$C_6$) alkyl.

[43] The condensed heterocyclic compound or its salt, or N-oxide thereof according to any one of the above [1] to [41], wherein R$^7$ is halo ($C_1$-$C_6$) alkyl.

[44] The condensed heterocyclic compound or its salt, or N-oxide thereof according to any one of the above [1] to [41], wherein R$^7$ is halo ($C_1$-$C_6$) alkylthio, halo ($C_1$-$C_6$) alkylsulfinyl or halo ($C_1$-$C_6$) alkylsulfonyl.

[45] The condensed heterocyclic compound or its salt, or N-oxide thereof according to any one of the above [1] to [44], wherein each of Y1, Y2, Y3 and Y4 is independently a hydrogen atom, a halogen atom, $C_3$-$C_6$ cycloalkyl, ($C_3$-$C_6$) cycloalkyl optionally substituted with Y$^a$, $C_1$-$C_6$ alkyl, halo ($C_1$-$C_6$) alkyl, $C_1$-$C_6$ alkoxy, halo ($C_1$-$C_6$) alkoxy, $C_1$-$C_6$ alkylthio, halo ($C_1$-$C_6$) alkylthio, $C_1$-$C_6$ alkylsulfinyl, halo ($C_1$-$C_6$) alkylsulfinyl, $C_1$-$C_6$ alkylsulfonyl, halo ($C_1$-$C_6$) alkylsulfonyl, —NH$_2$, —NHR$^{9\ 0\ g}$, cyano, nitro, G1 or G2.

[46] The condensed heterocyclic compound or its salt, or N-oxide thereof according to any one of the above [1] to [44], wherein each of Y1, Y2, Y3 and Y4 is independently a hydrogen atom, a halogen atom, halo ($C_1$-$C_6$) alkyl, G1 or G2.

[47] The condensed heterocyclic compound or its salt, or N-oxide thereof according to any one of the above [1] to [44], wherein each of Y1, Y2, Y3 and Y4 is independently a hydrogen atom, a halogen atom or halo ($C_1$-$C_6$) alkyl.

[48] The condensed heterocyclic compound or its salt, or N-oxide thereof according to any one of the above [1] to [44], wherein each of Y1, Y2, Y3 and Y4 is independently a hydrogen atom, G1 or G2.

[49] The condensed heterocyclic compound or its salt, or N-oxide thereof according to any one of the above [1] to [44], wherein each of Y1, Y2, Y3 and Y4 is independently a hydrogen atom, —$NH_2$ or nitro.

[50] The condensed heterocyclic compound or its salt, or N-oxide thereof according to any one of the above [1] to [44], wherein each of Y1, Y2, Y3 and Y4 is independently a hydrogen atom, $C_3$-$C_6$ cycloalkyl, ($C_3$-$C_6$) cycloalkyl optionally substituted with $Y^a$, $C_1$-$C_6$ alkyl, $C_1$-$C_6$ alkoxy, halo ($C_1$-$C_6$) alkoxy, $C_1$-$C_6$ alkylthio, halo ($C_1$-$C_6$) alkylthio, $C_1$-$C_6$ alkylsulfinyl, halo ($C_1$-$C_6$) alkylsulfinyl, $C_1$-$C_6$ alkylsulfonyl, halo ($C_1$-$C_6$) alkylsulfonyl, —$NHR^{9\ o\ g}$ or cyano.

[51] The condensed heterocyclic compound or its salt, or N-oxide thereof according to any one of the above [1] to [44], wherein each of Y1, Y2, Y3 and Y4 is independently a hydrogen atom, halo ($C_1$-$C_6$) alkoxy, halo ($C_1$-$C_6$) alkylthio or halo ($C_1$-$C_6$) alkylsulfonyl.

[52] The condensed heterocyclic compound or its salt, or N-oxide thereof according to any one of the above [1] to [44], wherein each of Y1, Y2, Y3 and Y4 is independently a hydrogen atom, $C_3$-$C_6$ cycloalkyl, ($C_3$-$C_6$) cycloalkyl optionally substituted with $Y^a$, $C_1$-$C_6$ alkyl, $C_1$-$C_6$ alkoxy, $C_1$-$C_6$ alkylthio, $C_1$-$C_6$ alkylsulfinyl or $C_1$-$C_6$ alkylsulfonyl.

[53] The condensed heterocyclic compound or its salt, or N-oxide thereof according to any one of the above [1] to [52], wherein Y1 is a hydrogen atom or a halogen atom.

[54] The condensed heterocyclic compound or its salt, or N-oxide thereof according to any one of the above [1] to [52], wherein Y1 is a hydrogen atom.

[55] The condensed heterocyclic compound or its salt, or N-oxide thereof according to any one of the above [1] to [52], wherein Y1 is a halogen atom.

[56] The condensed heterocyclic compound or its salt, or N-oxide thereof according to any one of the above [1] to [55], wherein Y2 is a hydrogen atom, a halogen atom, halo ($C_1$-$C_6$) alkyl, G1 or G2.

[57] The condensed heterocyclic compound or its salt, or N-oxide thereof according to any one of the above [1] to [55], wherein Y2 is a hydrogen atom, a halogen atom or halo ($C_1$-$C_6$) alkyl.

[58] The condensed heterocyclic compound or its salt, or N-oxide thereof according to any one of the above [1] to [55], wherein Y2 is a hydrogen atom, G1 or G2.

[59] The condensed heterocyclic compound or its salt, or N-oxide thereof according to any one of the above [1] to [55], wherein Y2 is a halogen atom.

[60] The condensed heterocyclic compound or its salt, or N-oxide thereof according to any one of the above [1] to [55], wherein Y2 is halo ($C_1$-$C_6$) alkyl.

[61] The condensed heterocyclic compound or its salt, or N-oxide thereof according to any one of the above [1] to [60], wherein Y3 is a hydrogen atom, a halogen atom, halo ($C_1$-$C_6$) alkyl, G1 or G2.

[62] The condensed heterocyclic compound or its salt, or N-oxide thereof according to any one of the above [1] to [60], wherein Y3 is a hydrogen atom, a halogen atom or halo ($C_1$-$C_6$) alkyl.

[63] The condensed heterocyclic compound or its salt, or N-oxide thereof according to any one of the above [1] to [60], wherein Y3 is a hydrogen atom, G1 or G2.

[64] The condensed heterocyclic compound or its salt, or N-oxide thereof according to any one of the above [1] to [60], wherein Y3 is a halogen atom.

[65] The condensed heterocyclic compound or its salt, or N-oxide thereof according to any one of the above [1] to [60], wherein Y3 is halo ($C_1$-$C_6$) alkyl.

[66] The condensed heterocyclic compound or its salt, or N-oxide thereof according to any one of the above [1] to [65], wherein Y4 is a hydrogen atom, a halogen atom, halo ($C_1$-$C_6$) alkyl, G1 or G2.

[67] The condensed heterocyclic compound or its salt, or N-oxide thereof according to any one of the above [1] to [65], wherein Y4 is a hydrogen atom, a halogen atom or halo ($C_1$-$C_6$) alkyl.

[68] The condensed heterocyclic compound or its salt, or N-oxide thereof according to any one of the above [1] to [65], wherein Y4 is a hydrogen atom, G1 or G2.

[69] The condensed heterocyclic compound or its salt, or N-oxide thereof according to any one of the above [1] to [65], wherein Y4 is a hydrogen atom.

[70] The condensed heterocyclic compound or its salt, or N-oxide thereof according to any one of the above [1] to [65], wherein Y4 is a halogen atom or halo ($C_1$-$C_6$) alkyl.

[71] The condensed heterocyclic compound or its salt, or N-oxide thereof according to any one of the above [1] to [70], wherein G1 is a structure represented by G1-1.

[72] The condensed heterocyclic compound or its salt, or N-oxide thereof according to any one of the above [1] to [70], wherein G1 is a structure represented by G1-2, G1-3 or G1-4.

[73] The condensed heterocyclic compound or its salt, or N-oxide thereof according to any one of the above [1] to [72], wherein G2 is a structure represented by G2-1.

[74] The condensed heterocyclic compound or its salt, or N-oxide thereof according to any one of the above [1] to [72], wherein G2 is a structure represented by G2-2, G2-3 or G2-4.

[75] The condensed heterocyclic compound or its salt, or N-oxide thereof according to any one of the above [1] to [74], wherein $A^{1\ a}$ is a hydrogen atom.

[76] The condensed heterocyclic compound or its salt, or N-oxide thereof according to any one of the above [1] to [74], wherein $A^{1\ a}$ is $C_1$-$C_6$ alkyl.

[77] The condensed heterocyclic compound or its salt, or N-oxide thereof according to any one of the above [1] to [76], wherein $Z^1$ is a halogen atom, $C_1$-$C_6$ alkyl, halo ($C_1$-$C_6$) alkyl, $C_1$-$C_6$ alkoxy, halo ($C_1$-$C_6$) alkoxy, $C_1$-$C_6$ alkylthio, halo ($C_1$-$C_6$) alkylthio, $C_1$-$C_6$ alkylsulfinyl, halo ($C_1$-$C_6$) alkylsulfinyl, $C_1$-$C_6$ alkylsulfonyl, halo ($C_1$-$C_6$) alkylsulfonyl, cyano or nitro.

[78] The condensed heterocyclic compound or its salt, or N-oxide thereof according to any one of the above [1] to [76], wherein $Z^1$ is a halogen atom, $C_1$-$C_6$ alkyl, halo ($C_1$-$C_6$) alkyl, $C_1$-$C_6$ alkoxy, halo ($C_1$-$C_6$) alkoxy, cyano or nitro.

[79] The condensed heterocyclic compound or its salt, or N-oxide thereof according to any one of the above [1] to [76], wherein $Z^1$ is $C_1$-$C_6$ alkylthio, halo ($C_1$-$C_6$) alkylthio, $C_1$-$C_6$ alkylsulfinyl, halo ($C_1$-$C_6$) alkylsulfinyl, $C_1$-$C_6$ alkylsulfonyl or halo ($C_1$-$C_6$) alkylsulfonyl.

[80] The condensed heterocyclic compound or its salt, or N-oxide thereof according to any one of the above [1] to [79], wherein $Z^2$ is a halogen atom, $C_1$-$C_6$ alkyl, halo ($C_1$-$C_6$) alkyl, $C_1$-$C_6$ alkoxy, halo ($C_1$-$C_6$) alkoxy, $C_1$-$C_6$ alkylthio, halo ($C_1$-$C_6$) alkylthio, $C_1$-$C_6$ alkylsulfinyl, halo ($C_1$-$C_6$) alkylsulfinyl, $C_1$-$C_6$ alkylsulfonyl, halo ($C_1$-$C_6$) alkylsulfonyl, cyano or nitro.

[81] The condensed heterocyclic compound or its salt, or N-oxide thereof according to any one of the above [1] to [79], wherein $Z^2$ is a halogen atom, $C_1$-$C_6$ alkyl, halo ($C_1$-$C_6$) alkyl, $C_1$-$C_6$ alkoxy, halo ($C_1$-$C_6$) alkoxy, cyano or nitro.

[82] The condensed heterocyclic compound or its salt, or N-oxide thereof according to any one of the above [1] to [79], wherein $Z^2$ is $C_1$-$C_6$ alkylthio, halo ($C_1$-$C_6$) alkylthio, $C_1$-$C_6$ alkylsulfinyl, halo ($C_1$-$C_6$) alkylsulfinyl, $C_1$-$C_6$ alkylsulfonyl or halo ($C_1$-$C_6$) alkylsulfonyl.

[83] The condensed heterocyclic compound or its salt, or N-oxide thereof according to any one of the above [1] to [79], wherein $Z^2$ is halo ($C_1$-$C_6$) alkyl.

[84] The condensed heterocyclic compound or its salt, or N-oxide thereof according to any one of the above [1] to [83], wherein $Y^a$ is cyano, —C(O)OH or —C(O)$NH_2$.

[85] The condensed heterocyclic compound or its salt, or N-oxide thereof according to any one of the above [1] to [83], wherein $Y^a$ is cyano.

[86] The condensed heterocyclic compound or its salt, or N-oxide thereof according to any one of the above [1] to [83], wherein $Y^a$ is —C(O)OH or —C(O)$NH_2$.

[87] A pesticide containing as active ingredient(s) one or more selected from the condensed heterocyclic compounds and their salts as defined in the above [1] to [86].

[88] An agricultural chemical containing as active ingredient(s) one or more selected from the condensed heterocyclic compounds and their salts as defined in the above [1] to [86].

[89] A parasiticide against internal or external parasites in or on a mammal or bird, containing as active ingredient(s) one or more selected from the condensed heterocyclic compounds and their salts as defined in the above [1] to [86].

[90] The parasiticide according to the above [89], wherein the external parasites are Siphonaptera or ticks.

[91] An insecticide or acaricide containing as active ingredient(s) one or more selected from the condensed heterocyclic compounds and their salts as defined in the above [1] to [86].

[92] A soil treatment agent containing as active ingredient(s) one or more selected from the condensed heterocyclic compounds as defined in the above [1] to [86].

[93] The soil treatment agent according to the above [92], which is used to treat soil by irrigation.

[94] A seed treatment agent containing as active ingredient(s) one or more selected from the condensed heterocyclic compounds and their salts as defined in the above [1] to [86].

[95] The seed treatment agent according to the above [94], which is used to treat seeds by dipping.

Advantageous Effects of Invention

The compounds of the present invention have excellent insecticidal and acaricidal activities on many agricultural pest insects, spider mites, internal or external parasites in or on a mammal, fish or bird and have sufficient controlling effect on pest insects which have acquired resistance to conventional insecticides. The compounds of the present invention have little harmful effect on mammals, fishes and beneficial insects, show low persistence and are environmentally friendly. Thus, the present invention can provide useful novel pesticides.

DESCRIPTION OF EMBODIMENTS

In this specification, definitions and meanings of the following terms are as follows.

The compounds of the present invention can have geometrical isomers such as E-isomers and Z-isomers, depending on the types of substituents in them, and the present invention covers both E-isomers and Z-isomers and mixtures containing them in any ratios.

The compounds of the present invention can have optically active isomers due to the presence of one or more asymmetric carbon atoms or asymmetric sulfur atoms, and the present invention covers any optically active isomers and any racemates.

Further, the compounds of the present invention can have tautomers depending on the type of substituents in them, and the present invention covers all tautomers and mixtures containing them in any ratios.

Some of the compounds of the present invention can be converted, by ordinary methods, to salts with hydrogen halides such as hydrofluoric acid, hydrochloric acid, hydrobromic acid and hydroiodic acid, with inorganic acids such as nitric acid, sulfuric acid, phosphoric acid, chloric acid and perchloric acid, with sulfonic acids such as methanesulfonic acid, ethanesulfonic acid, trifluoromethanesulfonic acid, benzenesulfonic acid and p-toluenesulfonic acid, with carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid, with amino acids such as glutamic acid and aspartic acid, with alkali metals such as lithium, sodium and potassium, with alkaline earth metals such as calcium, barium and magnesium, with aluminum, and with quaternary ammonium such as tetramethylammonium, tetrabutylammonium and benzyltrimethylammonium.

In the present invention, the N-oxide is a compound having a nitrogen atom constituting the ring in the heterocyclic group oxidized. A heterocyclic group which may constitute an N-oxide may, for example, be a condensed ring containing a pyridine ring.

"The compound of the present invention represented by the formula (1)" will sometimes be referred to as "the compound (1) of the present invention", and "a compound represented by the formula (1-a)" will sometimes be referred to as "a compound (1-a)". The same applies to other compounds.

Next, specific examples of each substituent used herein will be given below. n—denotes normal, i—iso, s—secondary, and tert—tertiary.

As a "halogen atom", a fluorine atom, a chlorine atom, a bromine atom or an iodine atom may be mentioned. Herein, the expression "halo" also means such a halogen atom.

The expression "$C_a$-$C_b$ alkyl" herein means a linear or branched hydrocarbon group containing from a to b carbon atoms such as methyl, ethyl, n-propyl, i-propyl, n-butyl, i-butyl, s-butyl, tert-butyl, n-pentyl, 1,1-dimethylpropyl or n-hexyl, and those within the designated carbon number range are selected.

The expression "halo ($C_a$-$C_b$) alkyl" herein means a linear or branched hydrocarbon group containing from a to b carbon atoms in which hydrogen atom(s) on carbon atom(s) are optionally substituted with halogen atom(s) which may be identical with or different from one another if two or more halogen atoms are present, such as fluoromethyl, chloromethyl, bromomethyl, iodomethyl, difluoromethyl, dichloromethyl, trifluoromethyl, chlorodifluoromethyl, trichloromethyl, bromodifluoromethyl, 1-fluoroethyl, 2-fluoroethyl, 2-chloroethyl, 2-bromoethyl, 2,2-difluoroethyl, 2,2,2-trifluoroethyl, 2-chloro-2,2-difluoroethyl, 2,2,2-trichloroethyl, 2-bromo-2,2-difluoroethyl, 1,1,2,2-tetrafluoroethyl, 2-chloro-1,1,2-trifluoroethyl, 2-chloro-1,1,2,2-tetrafluoroethyl, pentafluoroethyl, 2,2-difluoropropyl, 3,3,3-trifluoropropyl, 3-bromo-3,3-difluoropropyl, 2,2,3,3-tetrafluoropropyl, 2,2,3,3,3-pentafluoropropyl, 1,1,2,3,3,3-hexafluoropropyl, heptafluoropropyl, 2,2,2-trifluoro-1-(methyl)ethyl, 2,2,2-trifluoro-1-(trifluoromethyl)ethyl, 1,2,2,2-tetrafluoro-1-(trifluoromethyl)ethyl, 2,2,3,4,4,4-hexafluorobutyl, 2,2,3,3,4,4,4-heptafluorobutyl and nonafluorobutyl, and those within the designated carbon number range are selected.

The expression "$C_a$-$C_b$ cycloalkyl" herein means a cyclic hydrocarbon group containing from a to b carbon atoms in the form of a 3- to 6-membered monocyclic or polycyclic ring which may optionally be substituted with an alkyl group as long as the number of carbon atoms does not exceed the designated carbon number range, such as cyclopropyl, 1-methylcyclopropyl, 2-methylcyclopropyl, 2,2-dimethylcyclopropyl, cyclobutyl, cyclopentyl or cyclohexyl, and those within the designated carbon number range are selected.

The expression "$C_a$-$C_b$ alkoxy" herein means an alkyl-O— group in which the alkyl is a previously mentioned alkyl group containing from a to b carbon atoms, such as methoxy, ethoxy, n-propyloxy, i-propyloxy, n-butyloxy, i-butyloxy, s-butyloxy, tert-butyloxy or 2-ethylhexyloxy, and those within the designated carbon number range are selected.

The expression "halo ($C_a$-$C_b$) alkoxy" herein means a haloalkyl-O— group in which the haloalkyl is a previously mentioned haloalkyl group containing from a to b carbon atoms, such as difluoromethoxy, trifluoromethoxy, chlorodifluoromethoxy, bromodifluoromethoxy, 2-fluoroethoxy, 2-chloroethoxy, 2,2,2-trifluoroethoxy, 1,1,2,2,-tetrafluoroethoxy, 2-chloro-1,1,2-trifluoroethoxy or 1,1,2,3,3,3-hexafluoropropyloxy, and those within the designated carbon number range are selected.

The expression "$C_a$-$C_b$ alkylthio" herein means an alkyl-S— group in which the alkyl is a previously mentioned alkyl group containing from a to b carbon atoms, such as methylthio, ethylthio, n-propylthio, i-propylthio, n-butylthio, i-butylthio, s-butylthio or tert-butylthio, and those within the designated carbon number range are selected.

The expression "halo ($C_a$-$C_b$) alkylthio" herein means a haloalkyl-S— group in which the haloalkyl is a previously mentioned haloalkyl group containing from a to b carbon atoms, such as difluoromethylthio, trifluoromethylthio, chlorodifluoromethylthio, bromodifluoromethylthio, 2,2,2-trifluoroethylthio, 1,1,2,2-tetrafluoroethylthio, 2-chloro-1,1,2-trifluoroethylthio, pentafluoroethylthio, 1,1,2,3,3,3-hexafluoropropylthio, heptafluoropropylthio, 1,2,2,2-tetrafluoro-1-(trifluoromethyl)ethylthio or nonafluorobutylthio, and those within the designated carbon number range are selected.

The expression "$C_a$-$C_b$ alkylsulfinyl" herein means an alkyl-S(O)— group in which the alkyl is a previously mentioned alkyl group containing from a to b carbon atoms, such as methylsulfinyl, ethylsulfinyl, n-propylsulfinyl, i-propylsulfinyl, n-butylsulfinyl, i-butylsulfinyl, s-butylsulfinyl or tert-butylsulfinyl, and those within the designated carbon number range are selected.

The expression "halo ($C_a$-$C_b$) alkylsulfinyl" herein means a haloalkyl-S(O)— group in which the haloalkyl is a previously mentioned haloalkyl group containing from a to b carbon atoms, such as difluoromethylsulfinyl, trifluoromethylsulfinyl, chlorodifluoromethylsulfinyl, bromodifluoromethylsulfinyl, 2,2,2-trifluoroethylsulfinyl, 1,2,2,2-tetrafluoro-1-(trifluoromethyl)ethylsulfinyl or nonafluorobutylsulfinyl, and those within the designated carbon number range are selected.

The expression "$C_a$-$C_b$ alkylsulfonyl" herein means an alkyl-$SO_2$— group in which the alkyl is a previously mentioned alkyl group containing from a to b carbon atoms, such as methylsulfonyl, ethylsulfonyl, n-propylsulfonyl, i-propylsulfonyl, n-butylsulfonyl, i-butylsulfonyl, s-butylsulfonyl or tert-butylsulfonyl, and those within the designated carbon number range are selected.

The expression "halo ($C_a$-$C_b$) alkylsulfonyl" herein means a haloalkyl-$SO_2$— group in which the haloalkyl is a previously mentioned haloalkyl group containing from a to b carbon atoms, such as difluoromethylsulfonyl, trifluoromethylsulfonyl, chlorodifluoromethylsulfonyl, bromodifluoromethylsulfonyl, 2,2,2-trifluoroethylsulfonyl, 1,1,2,2-tetrafluoroethylsulfonyl or 2-chloro-1,1,2-trifluoroethylsulfonyl, and those within the designated carbon number range are selected.

The expression "$C_a$-$C_b$ alkylcarbonyl" herein means an alkyl-C(O)— group in which the alkyl means a previously mentioned alkyl group containing from a to b carbon atoms, such as acetyl, propionyl, butyryl, isobutyryl, valeryl, isovaleryl, 2-methylbutanoyl, pivaloyl, hexanoyl or heptanoyl, and those within the designated carbon number range are selected.

The expression "halo ($C_a$-$C_b$) alkylcarbonyl" herein means a haloalkyl-C(O)— group in which the haloalkyl means a previously mentioned haloalkyl group containing from a to b carbon atoms, such as fluoroacetyl, chloroacetyl, difluoroacetyl, dichloroacetyl, trifluoroacetyl, chlorodifluoroacetyl, bromodifluoroacetyl, trichloroacetyl, pentafluoropropionyl, heptafluorobutanoyl or 3-chloro-2,2-dimethylpropanoyl, and those within the designated carbon number range are selected.

The expression "$C_a$-$C_b$ alkoxycarbonyl" herein means an alkyl-O—C(O)— group in which the alkyl means a previously mentioned alkyl group containing from a to b carbon atoms, such as methoxycarbonyl, ethoxycarbonyl, n-propyloxycarbonyl, i-propyloxycarbonyl, n-butoxycarbonyl, i-butoxycarbonyl, s-butoxycarbonyl, tert-butoxycarbonyl or 2-ethylhexyloxycarbonyl, and those within the designated carbon number range are selected.

The expression "halo ($C_a$-$C_b$) alkoxycarbonyl" herein means a haloalkyl-O—C(O)— group in which the haloalkyl means a previously mentioned haloalkyl group containing from a to b carbon atoms, such as chloromethoxycarbonyl, 2-chloroethoxycarbonyl, 2,2-difluoroethoxycarbonyl, 2,2,2-trifluoroethoxycarbonyl or 2,2,2-trichloroethoxycarbonyl, and those within the designated carbon number range are selected.

The expression such as "($C_a$-$C_b$) cycloalkyl optionally substituted with $Y^a$" means a previously mentioned cycloalkyl group having from a to b carbon atoms in which hydrogen atom(s) on carbon atom(s) are optionally substituted with optional $Y^a$, and those within the designated carbon number range are selected. When there are two or more $Y^a$s on ($C_a$-$C_b$) cycloalkyl, each $Y^a$ may be identical with or different from one another.

Now, processes for producing the compounds of the present invention represented by the above formula (1) will be described below. The compounds of the present invention may be produced, for example, by the following Processes 1 to 9.

[Process 1]

Among the compounds of the present invention represented by the formula (1), a compound (1-a) wherein n is an integer of 1 or 2 may be produced, for example, by reacting a compound (1-b) of the present invention wherein n is an integer of 0 and an oxidizing agent.

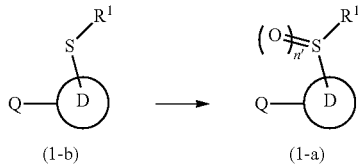

wherein D substituted with —S(O)$_n$R$^1$, Q and R$^1$ are as defined above, and n' is an integer of 1 or 2.

The compound (1-a) may be produced by reacting the compound (1-b) and an oxidizing agent in a solvent or without solvent and as the case requires, in the presence of a catalyst.

In a case where a solvent is used, the solvent may be any solvent which is inert to the reaction and may, for example, be water, a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N, N-dimethylacetamide, N-methylpyrrolidone or N,N'-dimethylimidazolidinone, a sulfoxide such as dimethylsulfoxide, a lower fatty acid such as acetic acid, or a mixture thereof. Hereinafter the above-exemplified solvents and mixtures thereof will generically be referred to as "solvent A".

The oxidizing agent may, for example, be a peracid such as m-chloroperbenzoic acid or peracetic acid, hydrogen peroxide or OXONE (tradename, manufactured by E. I. du Pont, potassium peroxymonosulfate content). The amount of the oxidizing agent used is from 0.1 to 100 equivalent amount, preferably from 1 to 20 equivalent amount per 1 equivalent amount of the compound (1-b).

The reaction may be carried out in the presence of a catalyst. The catalyst may, for example, be sodium tungstate. The amount of the catalyst used is from 0.005 to 20 equivalent amount, preferably from 0.1 to 5 equivalent amount per 1 equivalent amount of the compound (1-b).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

According to this Process, a compound (1-1-a) may be produced from a compound (1-1-b), and a compound (1-2-a) may be produced from a compound (1-2-b).

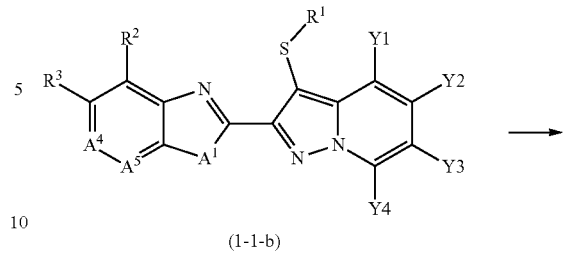

wherein R$^1$, R$^2$, R$^3$, A$^1$, A$^4$, A$^5$, Y1, Y2, Y3, Y4 and n' are as defined above.

[Process 2]

The compound (1-1-b) may be produced, for example, by reacting a compound (3-1) and a compound (10).

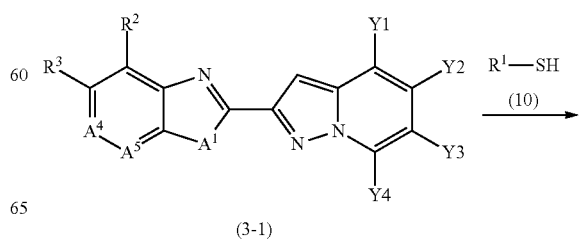

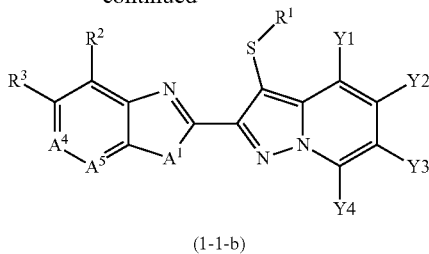

(1-1-b)

wherein $R^1$, $R^2$, $R^3$, $A^1$, $A^4$, $A^5$, Y1, Y2, Y3 and Y4 are as defined above.

The compound (1-1-b) may be produced by reacting the compound (3-1) and the compound (10) in the presence of a halogenating agent in a solvent or without solvent.

In a case where a solvent is used, the solvent may be any solvent which is inert to the reaction and may, for example, be the above-mentioned "solvent A".

The halogenating agent may, for example, be chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin or 1,3-diiodo-5,5-dimethylhydantoin. The amount of the halogenating agent is from 0.5 to 50 equivalent amount, preferably from 1 to 20 equivalent amount per 1 equivalent amount of the compound (3-1).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the amount of the substrate used, the amount of the compound (10) may be from 0.5 to 50 equivalent amount, preferably from 1 to 20 equivalent amount per 1 equivalent amount of the compound (3-1).

Some of the compounds (10) are known compounds, and some of them are commercially available.

[Process 3]

Among the compounds (1) of the present invention, the compound (1-b) may be produced, for example, by reacting a compound (2) and a compound (11).

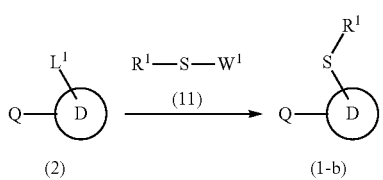

wherein D substituted with —S(O)$_n$R$^1$, Q and R$^1$ are as defined above, L$^1$ is a chlorine atom, a bromine atom or an iodine atom, and W$^1$ is a hydrogen atom, a sodium atom or a potassium atom.

The compound (1-b) may be produced by reacting the compound (2) and the compound (11) in a solvent or without solvent and as the case requires, in a presence of a base, a palladium catalyst and a ligand.

In a case where a solvent is used, the solvent may be any solvent which is inert to the reaction and may, for example, be the above-mentioned "solvent A".

The reaction may be carried out in the presence of a base. The base may, for example, be an organic base such as pyridine, 2,6-lutidine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The amount of the base used is from 0.1 to 100 equivalent amount, preferably from 1 to 20 equivalent amount per 1 equivalent amount of the compound (2).

The reaction may be carried out in the presence of a palladium catalyst. The palladium catalyst may, for example, be palladium-carbon, palladium(II) chloride, palladium(II) acetate, bis(triphenylphosphine)palladium(II) dichloride, tetrakis(triphenylphosphine)palladium(0), bis(dibenzylideneacetone)palladium(0) or tris(dibenzylideneacetone)dipalladium(0). The amount of the palladium catalyst used may be from 0.005 to 20 equivalent amount, preferably from 0.01 to 5 equivalent amount per 1 equivalent amount of the compound (2).

The reaction may be carried out in the presence of a ligand. The ligand may, for example, be 4,5'-bis(diphenylphosphino)-9,9'-dimethylxanthene or 1,10-phenanthroline. The amount of the ligand used may be from 0.005 to 20 equivalent amount, preferably from 0.01 to 5 equivalent amount per 1 equivalent amount of the compound (2).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the amount of the substrate, the amount of the compound (11) may be from 0.5 to 50 equivalent amount, preferably from 1 to 20 equivalent amount per 1 equivalent amount of the compound (2).

Some of the compounds (11) are known compounds, and some of them are commercially available.

According to this Process, for example, the compound (1-1-b) may be produced from a compound (2-1), and the compound (1-2-b) may be produced from a compound (2-2).

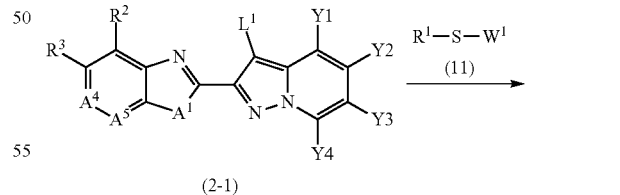

(2-1)

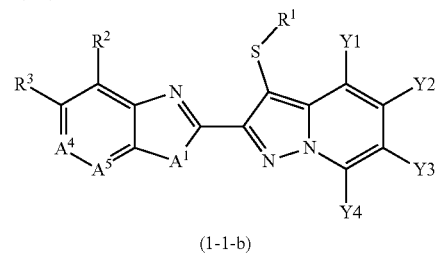

(1-1-b)

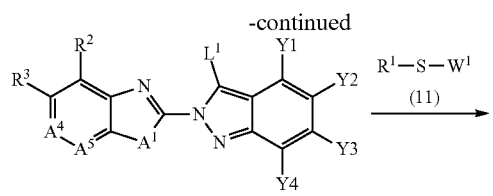

(2-2)

[structure (1-2-b)]

wherein $R^1$, $R^2$, $R^3$, $A^1$, $A^4$, $A^5$, Y1, Y2, Y3, Y4, $L^1$ and $W^1$ are as defined above.

[Process 4]

Among the compounds (1) of the present invention, a compound (1-d) and a compound (1-e) may be produced, for example, by reacting a compound (1-c) wherein one or more of Y1, Y2, Y3 and Y4 is a halogen atom among the compounds (1) of the present invention and a compound (12-1) or a compound (12-2).

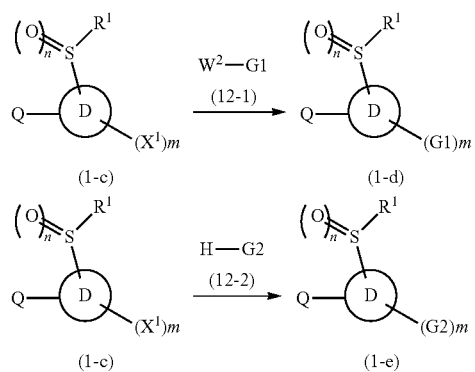

wherein D substituted with —S(O)$_n$R$^1$, Q, R$^1$, G1, G2 and n are as defined above, X$^1$ is a halogen atom, m is an integer of 1, 2, 3 or 4, W$^2$ is Sn(R$^a$)$_3$, B(OR$^b$)$_2$ or the like, R$^a$ is $C_1$-$C_6$ alkyl, and R$^b$ is a hydrogen atom or $C_1$-$C_6$ alkyl.

The compound (1-d) may be produced by reacting the compound (1-c) and the compound (12-1), and the compound (1-e) may be produced by reacting the compound (1-c) and the compound (12-2), respectively in a solvent or without solvent in the presence of a catalyst, a ligand and a base.

In a case where a solvent is used, the solvent may be any solvent which is inert to the reaction and may, for example, be the above-mentioned "solvent A".

The catalyst may, for example, be palladium-carbon, palladium(II) chloride, palladium(II) acetate, bis(triphenylphosphine)palladium(II) dichloride, tetrakis(triphenylphosphine)palladium(0), bis(dibenzylideneacetone)palladium (0), tris(dibenzylideneacetone)dipalladium(0), or cupper(I) iodide. The amount of the catalyst used may be from 0.005 to 20 equivalent amount, preferably from 0.01 to 5 equivalent amount per 1 equivalent amount of the compound (1-c).

The ligand may, for example, be 4,5'-bis(diphenylphosphino)-9,9'-dimethylxanthene, 1,10-phenanthroline, 1,2-diaminoethane, N,N'-dimethylethylenediamine or N,N'-dimethylcyclohexane-1,2-diamine. The amount of the ligand used may be from 0.005 to 20 equivalent amount, preferably from 0.01 to 5 equivalent amount per 1 equivalent amount of the compound (1-c).

The base may, for example, be an organic base such as pyridine, 2,6-lutidine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The amount of the base used is from 0.1 to 100 equivalent amount, preferably from 1 to 20 equivalent amount per 1 equivalent amount of the compound (1-c).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the amount of the substrate, the amount of the compound (12-1) and the compound (12-2) may be used from 0.5 to 50 equivalent amount, preferably from 1 to 20 equivalent amount per 1 equivalent amount of the compound (1-c).

Some of the compounds (12-1) and the compounds (12-2) are known compounds, and some of them are commercially available.

According to this Process, for example, a compound (1-1-e) may be produced from a compound (1-1-c).

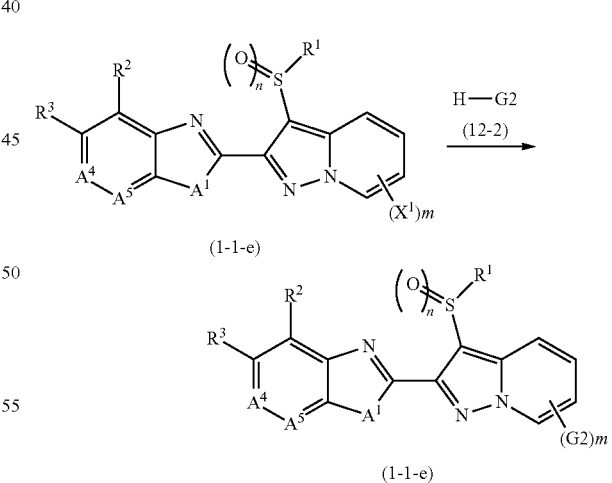

wherein R$^1$, R$^2$, R$^3$, A$^1$, A$^4$, A$^5$, G2, X$^1$, n and m are as defined above.

[Process 5]

Among the compounds (1) of the present invention, the compound (1-3) may be produced, for example, by reacting a compound (13) and a compound (5-1) in accordance with Synthetic Example 11 disclosed in WO2016/129684.

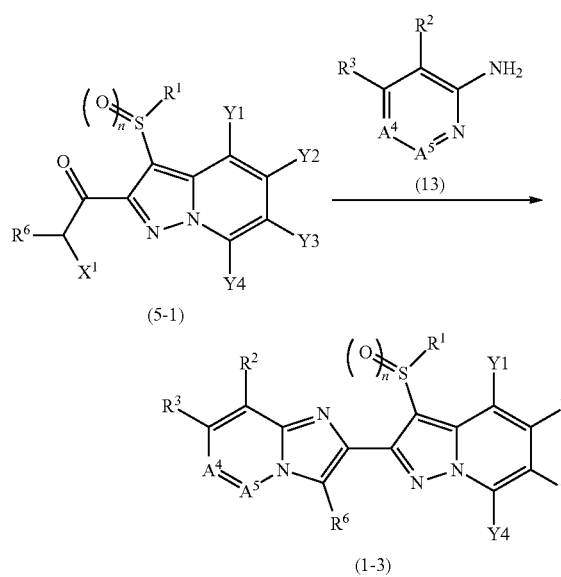

(5-1) + (13) → (1-3)

wherein $R^1$, $R^2$, $R^3$, $R^6$, $A^4$, $A^5$, Y1, Y2, Y3, Y4, $X^1$ and n are as defined above.

Some of the compounds (13) are known compounds, and some of them are commercially available. The rest of them may be prepared in accordance with known methods, for example, in accordance with the reaction conditions disclosed in WO2016/129684 or the like.

[Process 6]

Among the compounds (1) of the present invention, a compound (1-4) may be produced, for example, by reacting a compound (14) and a compound (5-1) in accordance with Synthetic Example 14 disclosed in WO2016/129684.

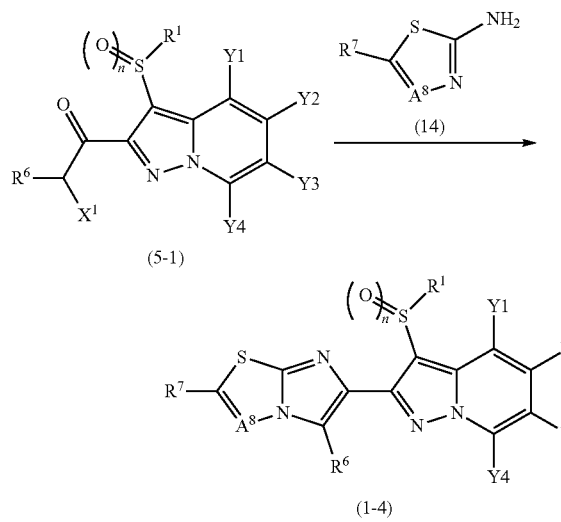

(5-1) + (14) → (1-4)

wherein $R^1$, $R^6$, $R^7$, $A^8$, Y1, Y2, Y3, Y4, $X^1$ and n are as defined above.

Some of the compounds (14) are known compounds, and some of them are commercially available. The rest of them may be prepared in accordance with known methods, for example, in accordance with the reaction conditions disclosed in Journal of Fluorine Chemistry, 2012, vol. 133, p. 115, or the like.

[Process 7]

Among the compounds (1) of the present invention, a compound (1-5) may be produced, for example, by reaction from a compound (5-2) in accordance with Synthetic Example 17 disclosed in WO2016/129684.

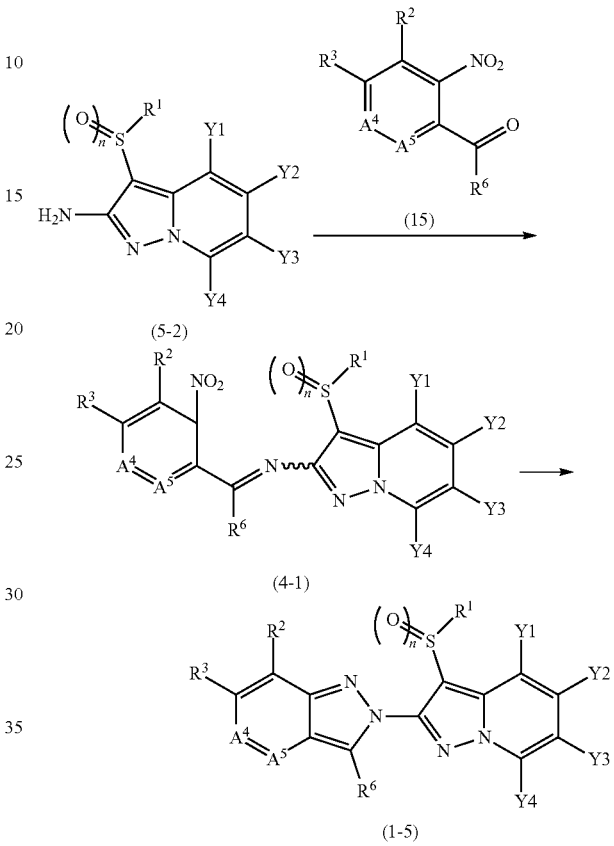

(5-2) + (15) → (4-1) → (1-5)

wherein $R^1$, $R^2$, $R^3$, $R^6$, $A^4$, $A^5$, Y1, Y2, Y3, Y4 and n are as defined above.

Some of the compounds (15) are known compounds, and some of them are commercially available. The rest of them may be prepared in accordance with known methods, for example, in accordance with Process disclosed in WO2016/129684 or the like.

[Process 8]

Among the compounds (1) of the present invention, a compound (1-6) may be produced, for example, by reacting a compound (5-3) and a compound (16).

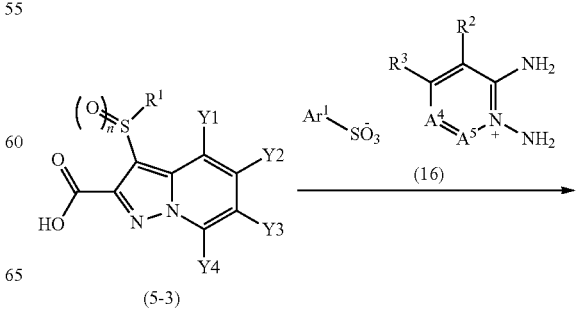

(5-3) + (16) →

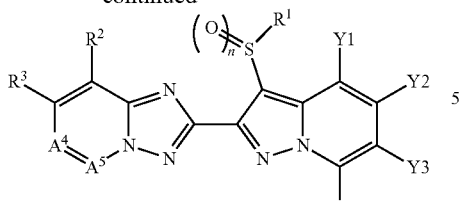

(1-6)

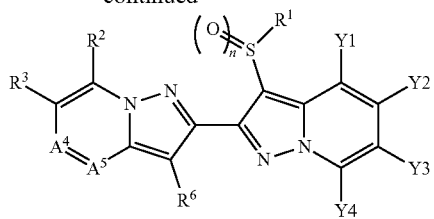

(1-7)

wherein $R^1$, $R^2$, $R^3$, $A^4$, $A^5$, Y1, Y2, Y3, Y4 and n are as defined above, and $A^1$ is a non-substituted or substituted benzene such as a phenyl group, a p-tolyl group or a 2,4,6-trimethylphenyl group.

The compound (1-6) may be produced by reacting the compound (5-3) and the compound (16) in a solvent or without solvent in the presence of a dehydration condensation agent, and as the case requires, in the presence of a base.

In a case where a solvent is used, the solvent may be any solvent which is inert to the reaction and may, for example, be the above-mentioned "solvent A".

The dehydration condensation agent may, for example, be 1H-benzotriazol-1-yloxytris(dimethylamino)phosphonium hexafluorophosphate, N,N'-dicyclohexylcarbodiimide or 1-ethyl-3-(3-dimethylaminopropyl)carbodiimide hydrochloride. The amount of the dehydration condensation agent used is from 0.1 to 100 equivalent amount, preferably from 1 to 20 equivalent amount per 1 equivalent amount of the compound (16).

The reaction may be carried out in the presence of a base. The base may, for example, be an organic base such as pyridine, triethylamine or 4-(dimethylamino)pyridine, or an inorganic base such as sodium hydroxide, potassium carbonate or cesium carbonate. The amount of the base used is from 0.1 to 100 equivalent amount, preferably from 1 to 20 equivalent amount per 1 equivalent amount of the compound (16).

The reaction time varies depending upon the concentration of the reaction substrate and the reaction temperature, and is optionally set usually within a range of from 5 minutes to 100 hours, and is preferably from 1 to 48 hours.

With respect to the amount of the substrate, the amount of the compound (5-3) may be from 0.5 to 50 equivalent amount, preferably from 1 to 20 equivalent amount per 1 equivalent amount of the compound (16).

Some of the compounds (16) are known compounds, and some of them are commercially available. The rest of them may be prepared, for example, in accordance with the method disclosed in WO2009/157423, WO2014/133046, WO2015/000715, or the like.

[Process 9]

Among the compounds (1) of the present invention, a compound (1-7) may be produced, for example, by reacting a compound (17) and a compound (5-4).

wherein $R^1$, $R^2$, $R^3$, $R^6$, $A^4$, Y1, Y2, Y3, Y4 and n are as defined above, and $X^2$ is a chlorine atom, $PF_6$ or $ClO_4$.

The compound (1-7) may be produced by reacting the compound (17) and the compound (5-4) in a solvent or without solvent and as the case requires, in the presence of a base.

In a case where a solvent is used, the solvent may be any solvent which is inert to the reaction and may, for example, be the above-mentioned "solvent A".

The reaction may be carried out in the presence of a base. The base may, for example, be an organic base such as pyridine, triethylamine or 4-(dimethylamino)pyridine, an inorganic base such as sodium hydroxide, sodium hydride, potassium carbonate or cesium carbonate, or an alkali metal alkoxide such as sodium methoxide or potassium tert-butoxide. The amount of the base used is from 0.1 to 100 equivalent amount, preferably from 1 to 20 equivalent amount per 1 equivalent amount of the compound (17).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the amount of the substrate, the amount of the compound (5-4) may be from 0.5 to 50 equivalent amount, preferably from 1 to 20 equivalent amount per 1 equivalent amount of the compound (17).

Some of the compounds (17) are known compounds, and some of them are commercially available.

The compound (3-1) used in Process 2 and the compound (2-1) used in Process 3 may be prepared, for example, in accordance with the following Reaction Schemes.

[Reaction Scheme 1]

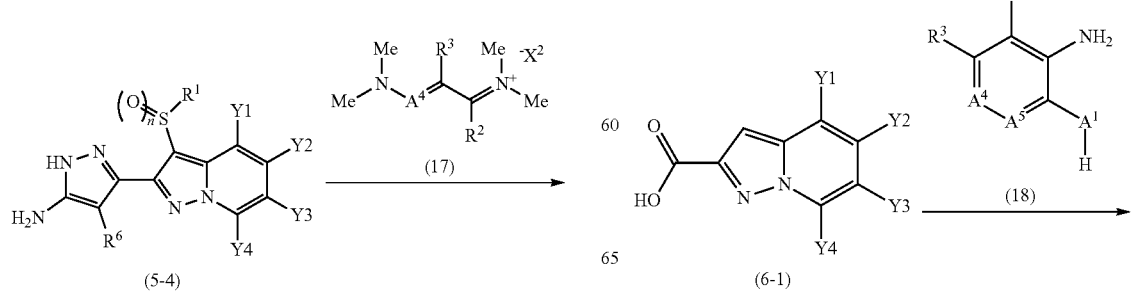

-continued

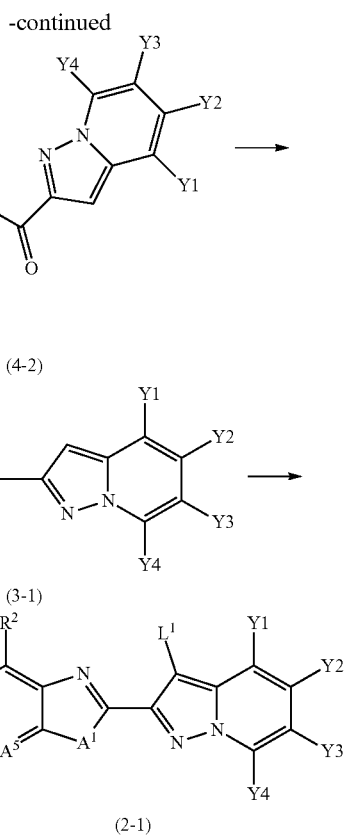

(4-2)

(3-1)

(2-1)

wherein $R^2$, $R^3$, $A^1$, $A^4$, $A^5$, Y1, Y2, Y3, Y4 and $L^1$ are as defined above.

Step 1: A compound (4-2) may be produced, for example, by reacting a compound (18) and a compound (6-1) in a solvent or without solvent in the presence of a dehydration condensation agent and as the case requires, in the presence of a base and as the case requires, in the presence of a catalyst.

In a case where a solvent is used, the solvent may be any solvent which is inert to the reaction and may, for example, be the above-mentioned "solvent A".

The dehydration condensation agent may, for example, be 1H-benzotriazol-1-yloxytris(dimethylamino)phosphonium hexafluorophosphate, N,N'-dicyclohexylcarbodiimide, 1-ethyl-3-(3-dimethylaminopropyl)carbodiimide hydrochloride, 2-chloro-1-methylpyridinium iodide or O-(7-azabenzotriazol-1-yl)-N,N,N',N'-tetramethyluronium hexafluorophosphate. The amount of the dehydration condensation agent used is from 0.1 to 100 equivalent amount, preferably from 1 to 20 equivalent amount per 1 equivalent amount of the compound (18).

The reaction may be carried out in the presence of a base. The base to be used may, for example, be an organic base such as pyridine, 2,6-lutidine, triethylamine, diisopropylethylamine, tributylamine, 4-(dimethylamino)pyridine, 1,4-diazabicyclo[2.2.2]octane (DABCO), 1,8-diazabicyclo[5.4.0]-7-undecene (DBU) or 1,5-diazabicyclo[4.3.0]-5-nonene (DBN), or an inorganic base such as sodium hydroxide, potassium hydroxide, sodium hydride, sodium hydrogen carbonate, potassium carbonate or cesium carbonate. The amount of the base used is from 0.1 to 100 equivalent amount, preferably from 1 to 20 equivalent amount per 1 equivalent amount of the compound (18).

The reaction may be carried out in the presence of a catalyst. The catalyst may, for example, be 1-hydroxybenzotriazole or 4-(dimethylamino)pyridine. The amount of the catalyst used is from 0.005 to 20 equivalent amount, preferably from 0.1 to 5 equivalent amount per 1 equivalent amount of the compound (18).

The reaction time varies depending upon the concentration of the reaction substrate and the reaction temperature, and is optionally set usually within a range of from 5 minutes to 100 hours, and is preferably from 1 to 48 hours.

With respect to the amount of the substrate, the amount of the compound (6-1) may be from 0.5 to 50 equivalent amount, preferably from 1 to 20 equivalent amount per 1 equivalent amount of the compound (18).

Some of the compounds (18) are known compounds, and some of them are commercially available.

Some of the compounds (6-1) are known compounds, and some of them are commercially available. The rest of them may be prepared, for example, in accordance with the reaction conditions disclosed in WO2009/095253, WO2011/015343, or the like.

Step 2: The compound (3-1) may be produced, for example, by subjecting the compound (4-2) to reaction in a solvent or without solvent and as the case requires, in the presence of an acid or a dehydration condensation agent.

In a case where a solvent is used, the solvent may be any solvent which is inert to the reaction and may, for example, be a lower alcohol such as methanol or ethanol, an ether such as diethyl ether, tetrahydrofuran, 1,4-dioxane or 1,2-dimethoxyethane, an aromatic hydrocarbon such as benzene, chlorobenzene, bromobenzene, xylene or toluene, an aliphatic hydrocarbon such as pentane, hexane or cyclohexane, a halogenated hydrocarbon such as dichloromethane, chloroform or 1,2-dichloroethane, a nitrile such as acetonitrile or propionitrile, an amide such as N,N-dimethylformamide, N,N-dimethylacetamide, N-methylpyrrolidone or N,N'-dimethylimidazolidinone, a sulfoxide such as dimethylsulfoxide, a nitrogen-containing aromatic compound such as pyridine, or a mixture thereof. Hereinafter the above-exemplified solvents and mixtures thereof will generically be referred to as "solvent B".

The reaction may be carried out in the presence of an acid. The acid may, for example, be p-toluenesulfonic acid, polyphosphoric acid, acetic acid or propionic acid. The amount of the acid used is from 0.1 to 1,000 equivalent amount, preferably from 1 to 500 equivalent amount per 1 equivalent amount of the compound (4-2).

The reaction may be carried out in the presence of a dehydration condensation agent. The dehydration condensation agent may, for example, be phosphorus oxychloride or acetic anhydride. The amount of the dehydration condensation agent used is from 0.5 to 50 equivalent amount, preferably from 1 to 20 equivalent amount per 1 equivalent amount of the compound (4-2).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

Step 3: The compound (2-1) may be produced, for example, by reacting the compound (3-1) and a halogenating agent in a solvent or without solvent.

In a case where a solvent is used, the solvent may be any solvent which is inert to the reaction and may, for example, be the above-mentioned "solvent A".

The halogenating agent may, for example, be chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin or 1,3-diiodo-5,5-dimethylhydantoin. The amount of the halogenating agent used is from 0.5 to 50 equivalent amount, preferably from 1 to 20 equivalent amount per 1 equivalent amount of the compound (3-1).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

A compound (2-a) including the compound (2-2) used in Process 3 may be produced, for example, in accordance with the following Reaction Scheme.

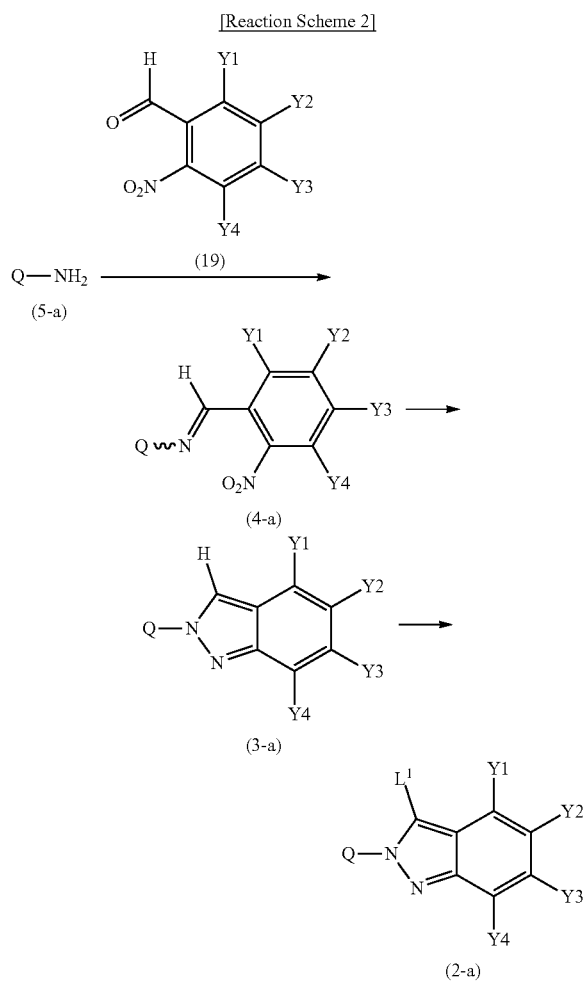

wherein Q, Y1, Y2, Y3, Y4 and L$^1$ are as defined above.

Step 1: A compound (4-a) may be produced, for example, by reacting a compound (5-a) and a compound (19) in a solvent or without solvent and as the case requires, in the presence of an acid.

In a case where a solvent is used, the solvent may be any solvent which is inert to the reaction and may, for example, be the above-mentioned "solvent B".

The reaction may be carried out in the presence of an acid. The acid may, for example, be p-toluenesulfonic acid, acetic acid or formic acid. The amount of the acid used is from 0.1 to 1,000 equivalent amount, preferably from 1 to 20 equivalent amount per 1 equivalent amount of the compound (5-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the amount of the substrate, the amount of the compound (19) may be from 0.5 to 50 equivalent amount, preferably from 1 to 20 equivalent amount per 1 equivalent amount of the compound (5-a).

Some of the compounds (5-a) are known compounds, and some of them are commercially available. The rest of them may be prepared, for example, in accordance with the method disclosed in WO2002/081478, WO2004/098494, WO2009/136663, European Journal of Medicinal Chemistry, 2014, vol. 87, p. 386, WO2011/075615, WO2011/090127, WO2015/114452, or the like.

Some of the compounds (19) are known compounds, and some of them are commercially available.

Step 2: A compound (3-a) may be produced, for example, by reacting the compound (4-a) and a reducing agent in a solvent or without solvent.

In a case where a solvent is used, the solvent may be any solvent which is inert to the reaction and may, for example, be the above-mentioned "solvent B".

The reducing agent may, for example, be trimethylphosphine, triethylphosphine, tributylphosphine or triethylphosphite. The amount of the reducing agent used is from 0.5 to 50 equivalent amount, preferably from 1 to 20 equivalent amount per 1 equivalent amount of the compound (4-a).

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

Step 3: The compound (2-a) may be produced, for example, by reacting the compound (3-a) and a halogenating agent in a solvent or without solvent.

In a case where a solvent is used, the solvent used may be any solvent which is inert to the reaction and may, for example, the above-mentioned "solvent A".

The halogenating agent may, for example, be chlorine, bromine, iodine, N-chlorosuccinimide, N-bromosuccinimide, N-iodosuccinimide, 1,3-dichloro-5,5-dimethylhydantoin, 1,3-dibromo-5,5-dimethylhydantoin or 1,3-diiodo-5,5-dimethylhydantoin. The amount of the halogenating agent used is from 0.5 to 50 equivalent amount, preferably from 1 to 20 equivalent amount per 1 equivalent amount of the compound (3-a).

The reaction temperature may be set at an optional temperature of from −80° C. to the refluxing temperature of the reaction mixture, and is preferably within a range of from 000° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

According to process represented by Reaction Scheme 2, for example, the compound (2-2) to be used for Process 3 may be produced.

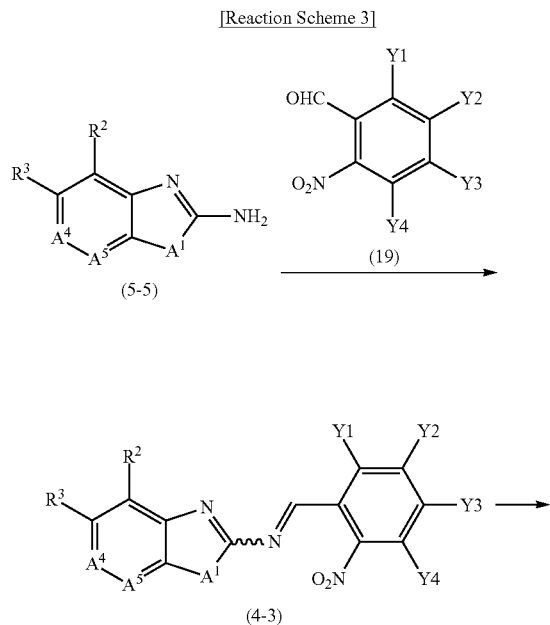

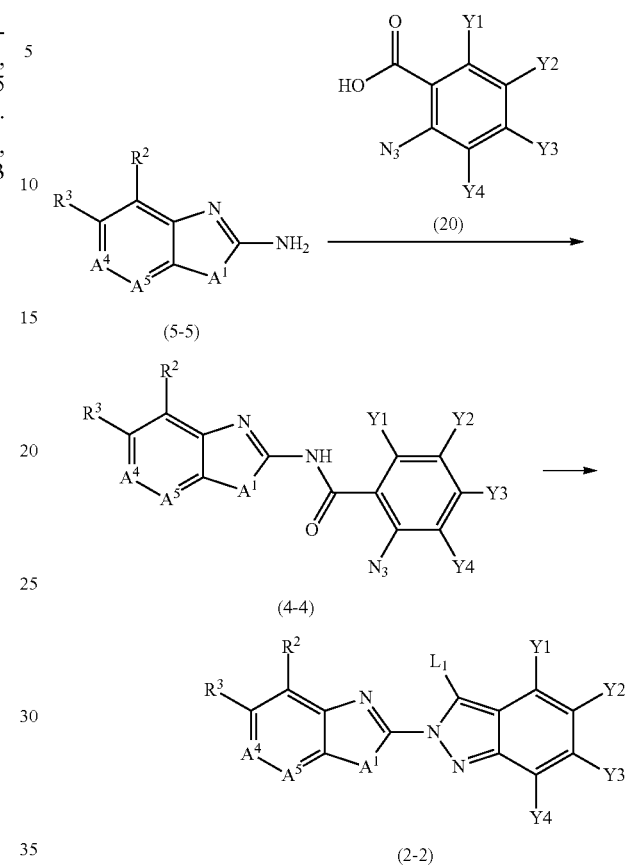

wherein $R^2$, $R^3$, $A^1$, $A^4$, $A^5$, Y1, Y2, Y3, Y4 and $L^1$ are as defined above.

Step 1: A compound (5-5) is subjected to a dehydration condensation reaction with a compound (20) in accordance with the method disclosed in step 1 of Reaction Scheme 1 to produce a compound (4-4). Some of the compounds (20) are known compounds, and some of them are commercially available.

Step 2: The compound (4-4) is reacted with a halogenating agent in accordance with a known method, for example, in accordance with the method disclosed in WO2011/153588 or the like, to produce the compound (2-2).

The compound (5-5) used in Reaction Schemes 3 and 4 may be produced, for example, in accordance with the following Reaction Scheme.

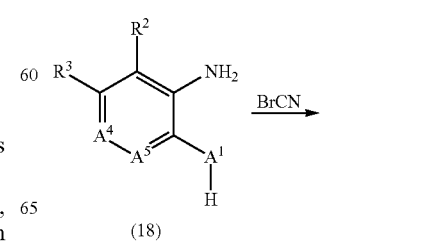

wherein $R^2$, $R^3$, $A^1$, $A^4$, $A^5$, Y1, Y2, Y3, Y4 and $L^1$ are as defined above.

The compound (2-2) used in Process 3 may be produced, for example, in accordance with the following Reaction Scheme.

-continued

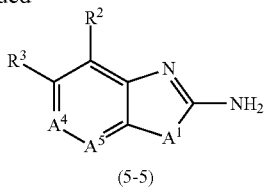

(5-5)

wherein $R^2$, $R^3$, $A^1$, $A^4$ and $A^5$ are as defined above.

The compound (5-5) may be produced, for example, by reacting the compound (18) and cyanogen bromide in a solvent or without solvent.

In a case where a solvent is used, the solvent used may be any solvent which is inert to the reaction and may, for example, the above-mentioned "solvent B".

The reaction temperature may be set at an optional temperature of from −80° C. to the refluxing temperature of the reaction mixture, and is preferably within a range of from 0° C. to the refluxing temperature of the reaction mixture.

The reaction time varies depending upon the concentration of the reaction substrate and the reaction temperature, and is optionally set usually within a range of from 5 minutes to 100 hours, and is preferably from 1 to 48 hours.

With respect to the amount of the substrate, the amount of cyanogen bromide may be from 0.5 to 50 equivalent amount, preferably from 1 to 20 equivalent amount per 1 equivalent amount of the compound (18).

The compound (5-1) to be used in Process 5 and Process 6 may be produced, for example, from a compound (5-3-b) as a starting material in accordance with Reaction Scheme 1 disclosed in WO2016/129684, in accordance with the following Reaction Scheme. A compound (5-1-a) is a compound (5-1) wherein n is an integer of 1 or 2, and a compound (5-1-b) is a compound (5-1) wherein n is an integer of 0.

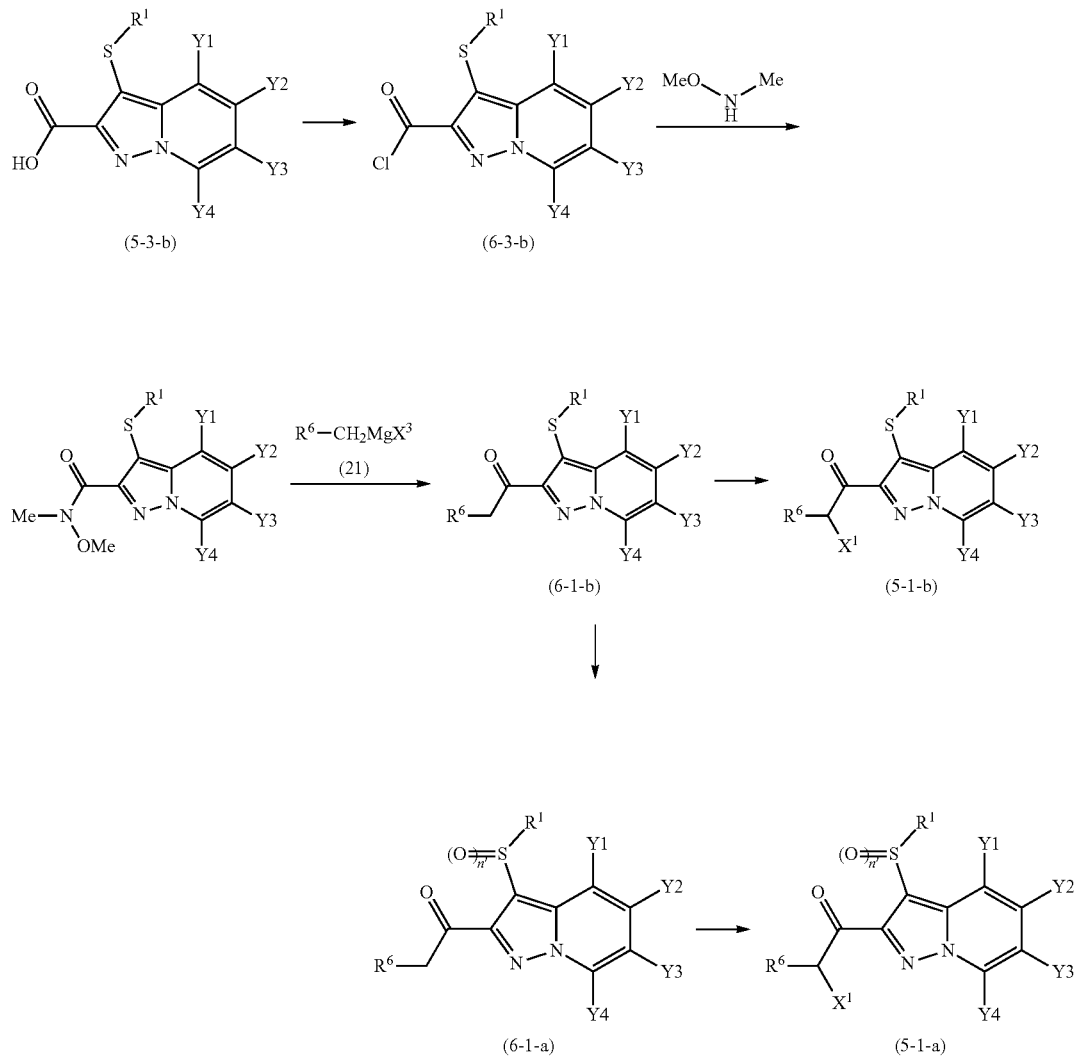

[Reaction Scheme 6]

wherein R¹, R⁶, Y1, Y2, Y3, Y4, X¹ and n' are as defined above, X³ is a chlorine atom, a bromine atom or an iodine atom, and n' is an integer of 1 or 2.

The compound (5-2) used in Process 7 may be produced, for example, in accordance with the following Reaction Scheme.

[Reaction Scheme 7]

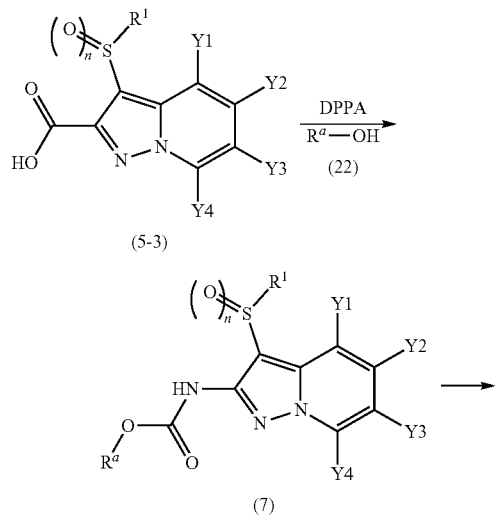

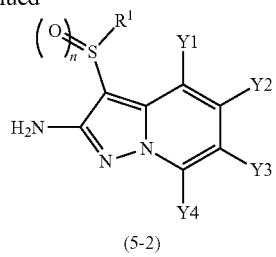

wherein R¹, Y1, Y2, Y3, Y4, n and $R^a$ are as defined above.

Step 1: The compound (5-3) is reacted with diphenyl-phosphoryl azide (DPPA) and a compound (22) in accordance with a known method disclosed in literature, for example, in accordance with the method disclosed in WO2012/174312, WO2003/018021 or the like, to produce a compound (7). Some of the compounds (22) are known compounds, and some of them are commercially available.

Step 2: The compound (7) is reacted with an acid in accordance with a known method, for example, in accordance with the method disclosed in WO2012/174312, WO2003/018021 or the like, to produce the compound (5-2).

The compound (5-3) used in Process 8 and Reaction Scheme 7 may be produced, for example, from a compound (8-3) as a starting material in accordance with Reaction Scheme 1 disclosed in WO2016/129684 in accordance with the following Reaction Scheme. A compound (5-3-a) is a compound (5-3) wherein n is an integer of 1 or 2, and the compound (5-3-b) is a compound (5-3) wherein n is an integer of 0.

[Reaction Scheme 8]

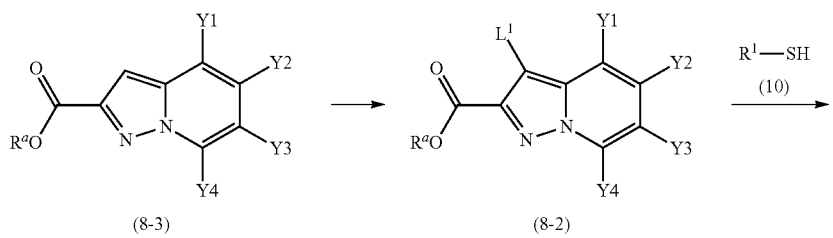

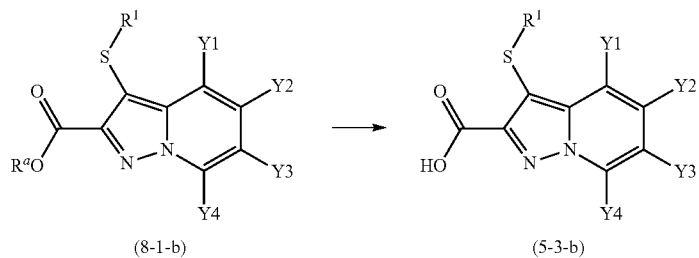

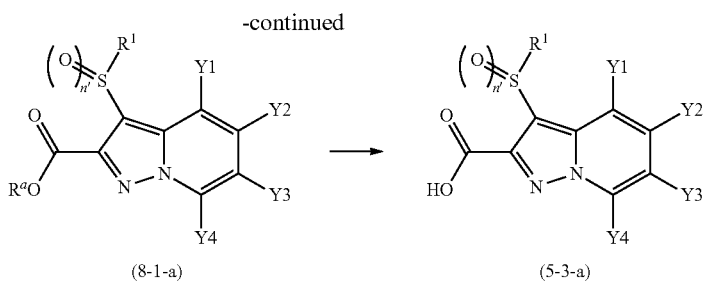

wherein $R^1$, Y1, Y2, Y3, Y4, $L^1$, $R^a$ and n' are as defined above.

Some of the compounds (8-3) are known compounds, and some of them are commercially available. The rest of them may be prepared, in accordance with a known method, for example, in accordance with the reaction conditions disclosed in WO2011/050284 or the like.

The compound (5-4) used in Process 9 may be produced, for example, in accordance with the following Reaction Scheme.

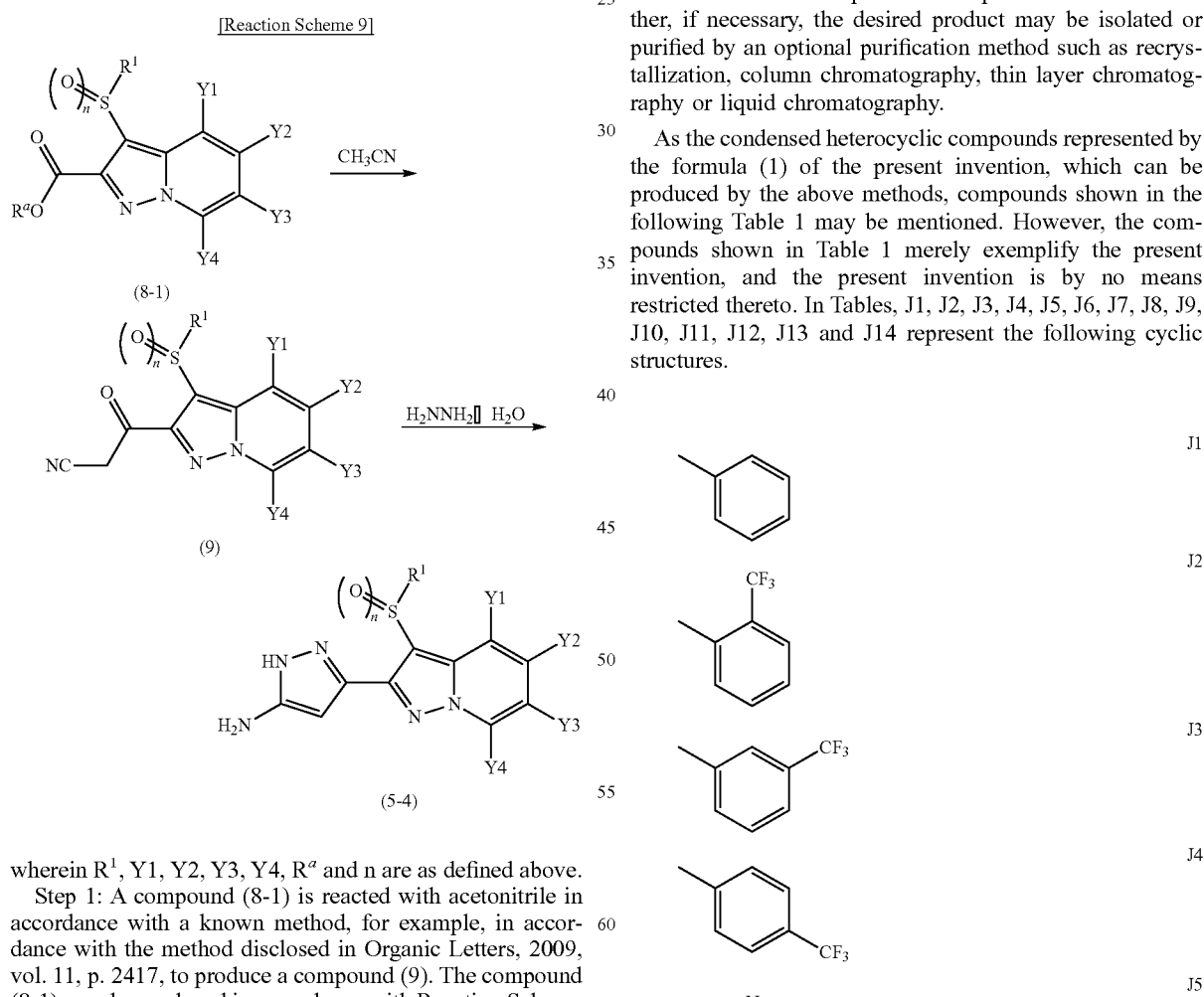

wherein $R^1$, Y1, Y2, Y3, Y4, $R^a$ and n are as defined above.

Step 1: A compound (8-1) is reacted with acetonitrile in accordance with a known method, for example, in accordance with the method disclosed in Organic Letters, 2009, vol. 11, p. 2417, to produce a compound (9). The compound (8-1) may be produced in accordance with Reaction Scheme 8.

Step 2: The compound (9) is reacted with hydrazine monohydrate in accordance with a known method, for example, in accordance with the method disclosed in WO2011/105628, Bioorganic & Medicinal Chemistry Letters, 2010, vol. 20, p. 922, or the like, to produce the compound (5-4).

In Processes 1 to 9 and Reaction Schemes 1 to 9, the reaction mixture after the reaction can be worked up by an ordinary procedure, for example, by direct concentration, by dissolving the reaction mixture in an organic solvent and washing the solution with water, followed by concentration, or by pouring the reaction mixture into ice water, followed by extraction with an organic solvent and concentration, to obtain the desired compound of the present invention. Further, if necessary, the desired product may be isolated or purified by an optional purification method such as recrystallization, column chromatography, thin layer chromatography or liquid chromatography.

As the condensed heterocyclic compounds represented by the formula (1) of the present invention, which can be produced by the above methods, compounds shown in the following Table 1 may be mentioned. However, the compounds shown in Table 1 merely exemplify the present invention, and the present invention is by no means restricted thereto. In Tables, J1, J2, J3, J4, J5, J6, J7, J8, J9, J10, J11, J12, J13 and J14 represent the following cyclic structures.

-continued
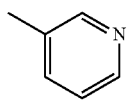 J6
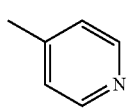 J7
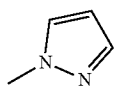 J8
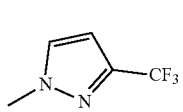 J9
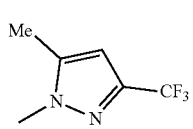 J10
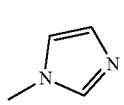 J11
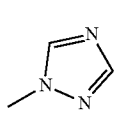 J12
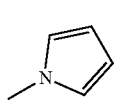 J13
 J14
In Table, Me represents a methyl group, and Et represents an ethyl group.
TABLE 1
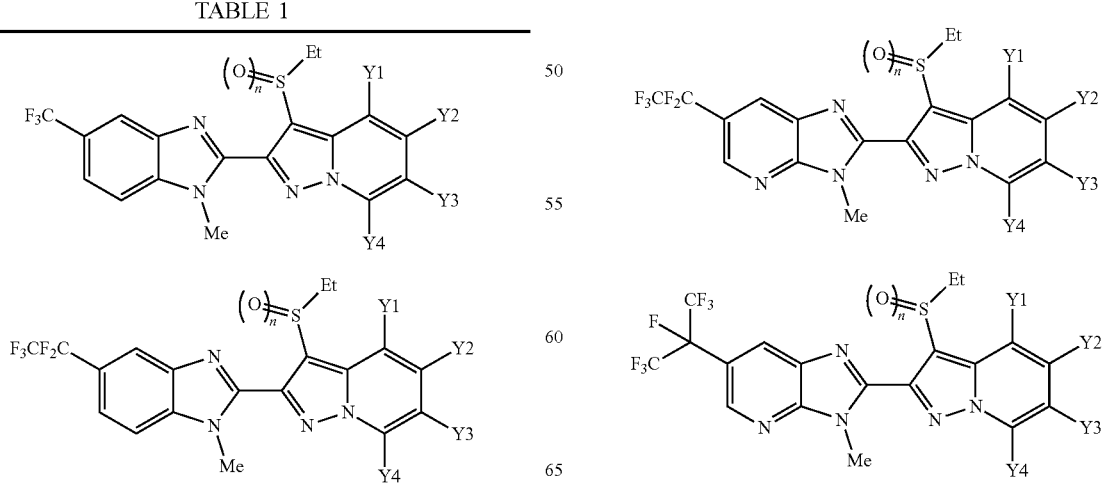
TABLE 1-continued
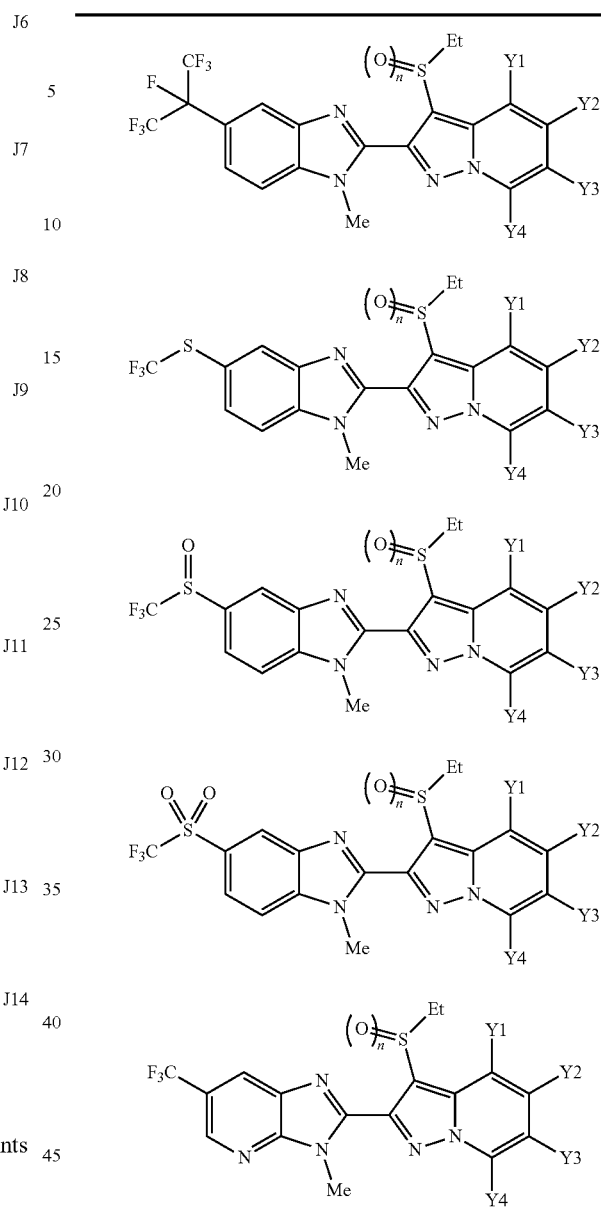

TABLE 1-continued
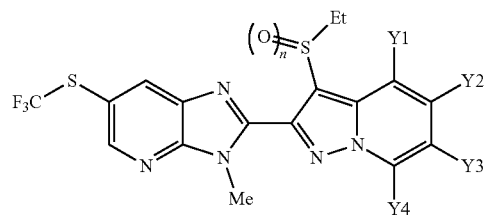
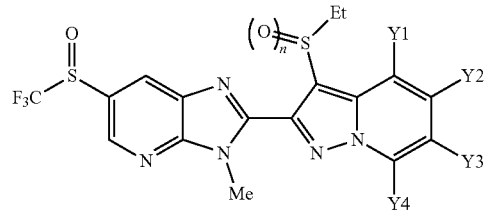
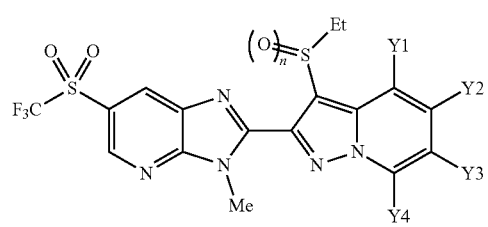
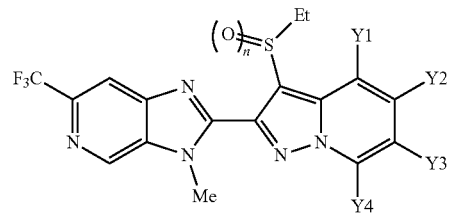
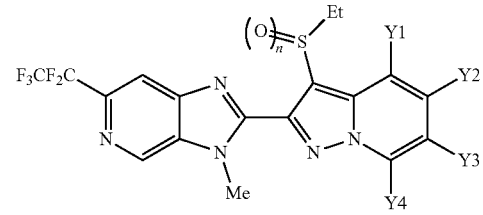
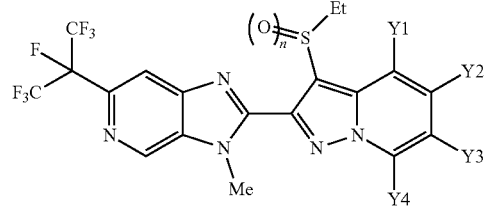
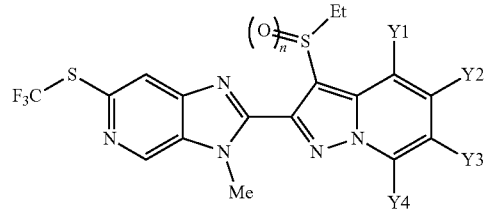
TABLE 1-continued
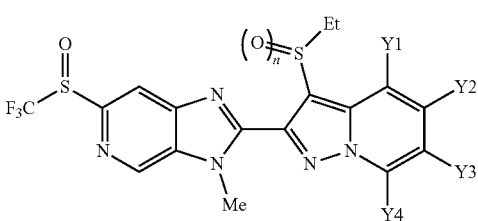
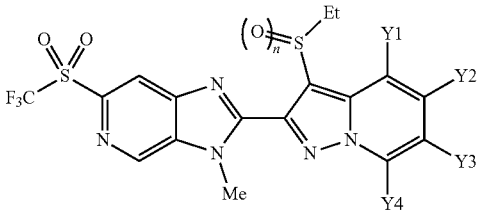
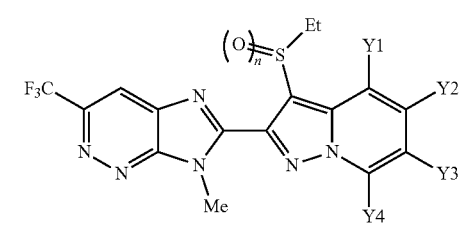
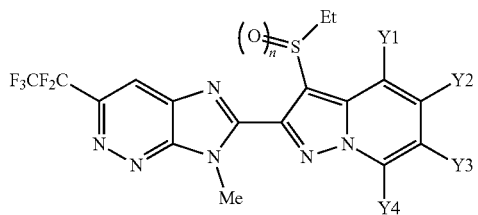
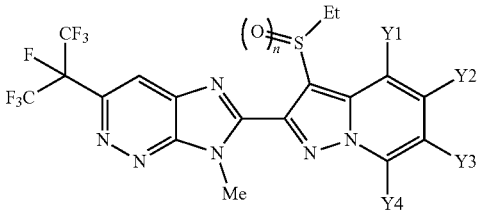
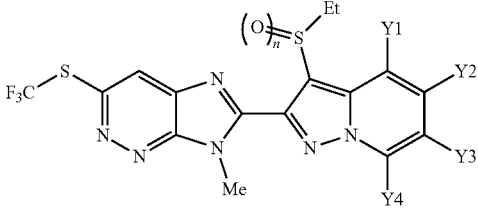
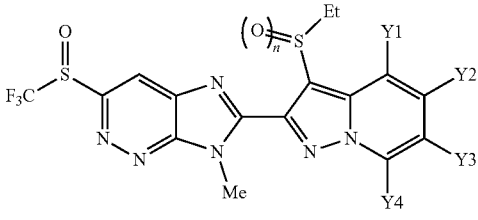

TABLE 1-continued
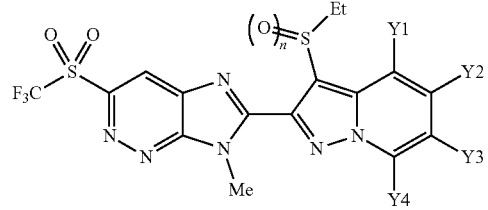
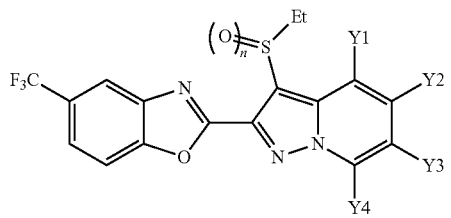
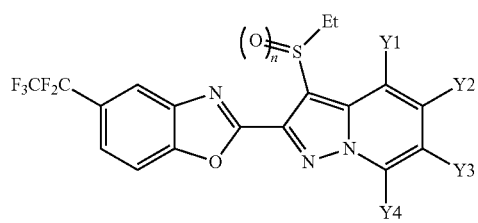
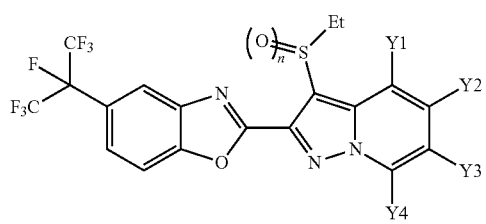
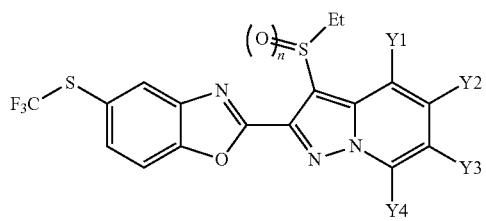
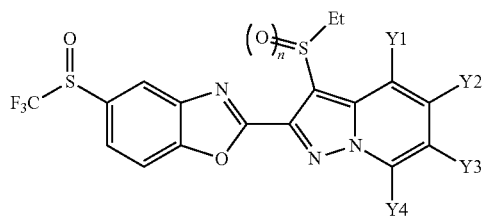
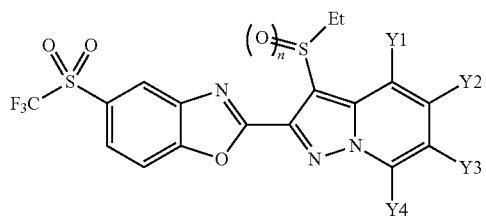
TABLE 1-continued
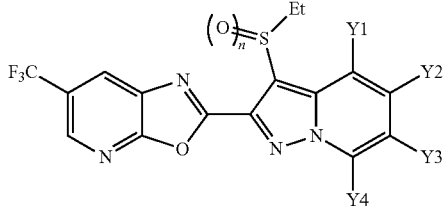
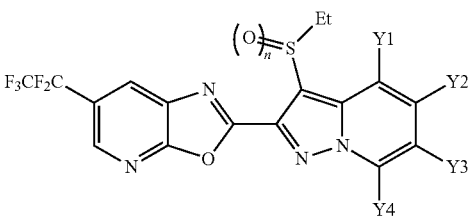
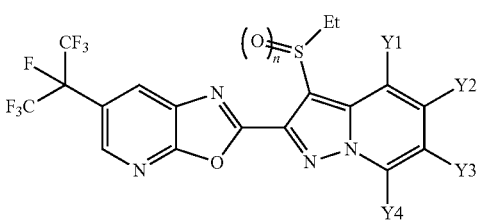
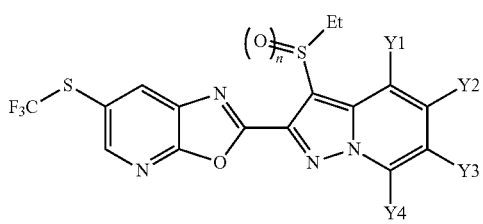
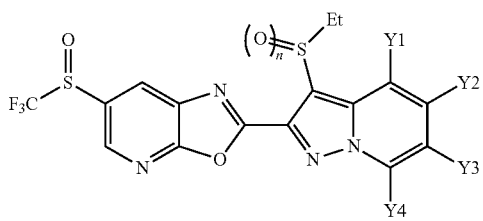
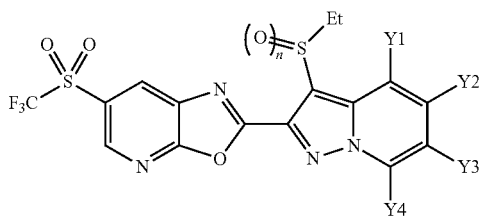
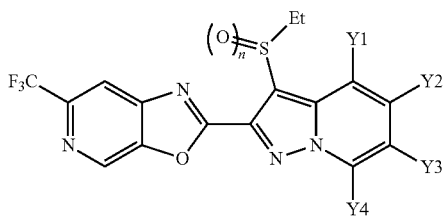

TABLE 1-continued
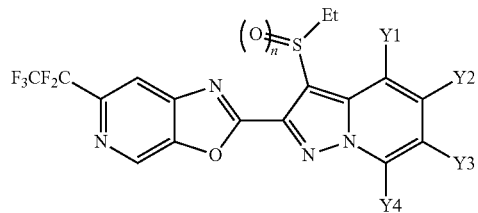
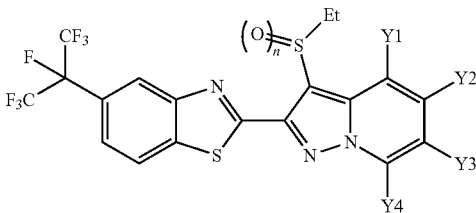
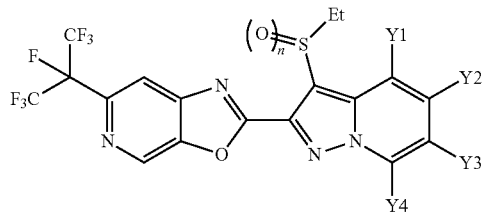
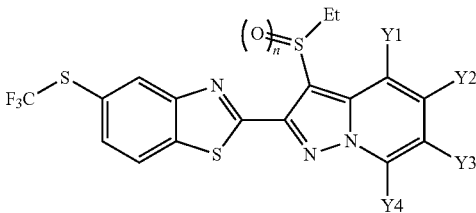
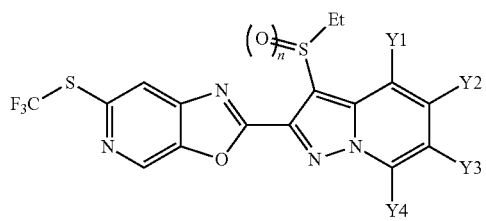
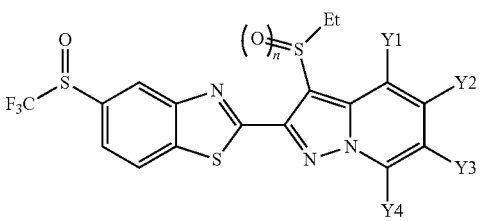
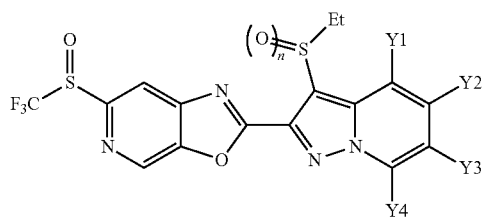
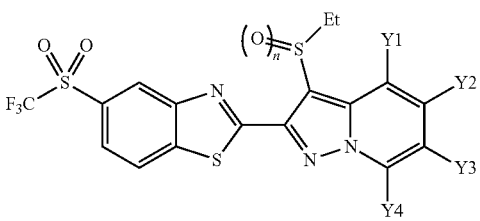
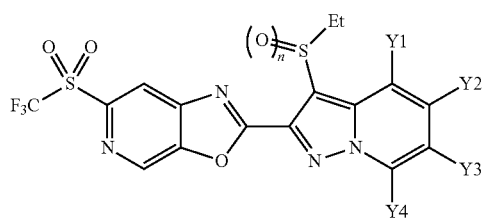
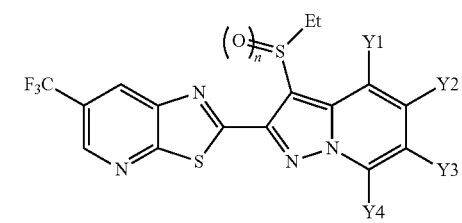
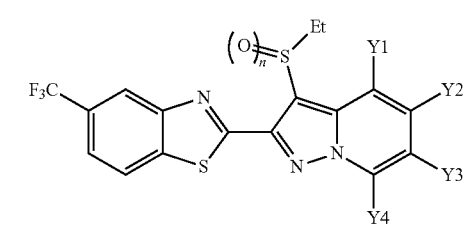
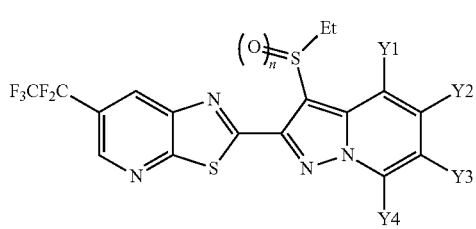
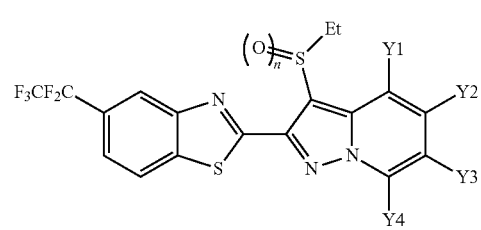
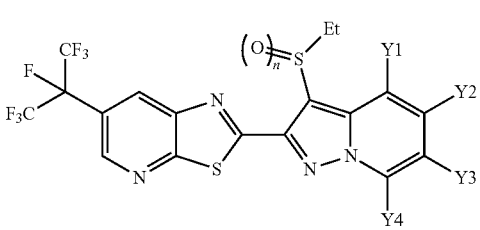

TABLE 1-continued
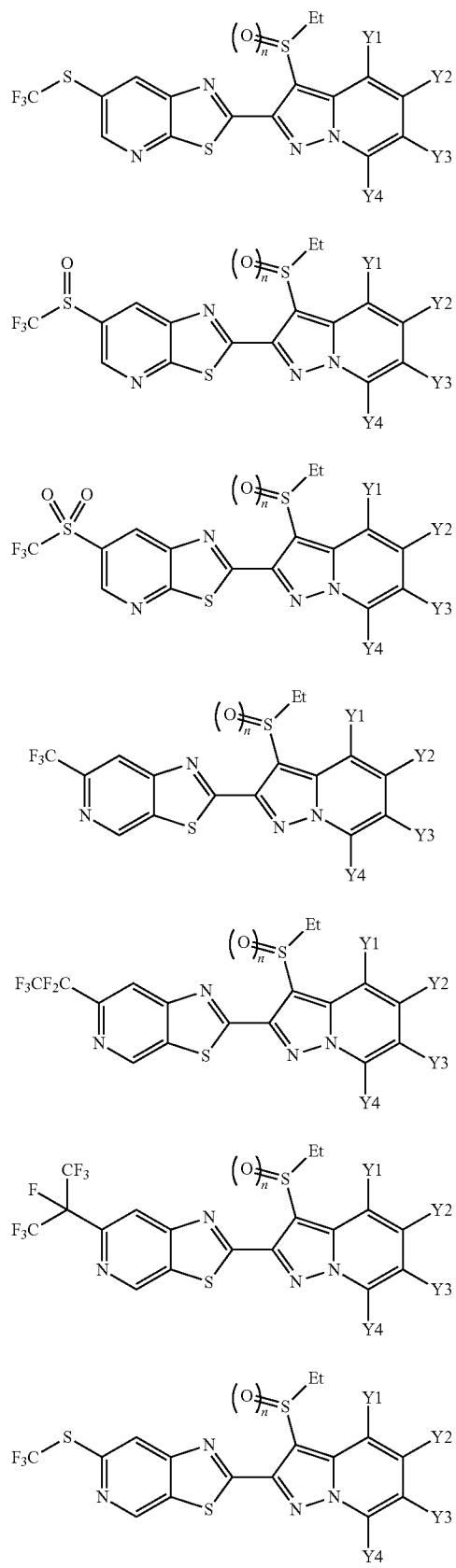
TABLE 1-continued
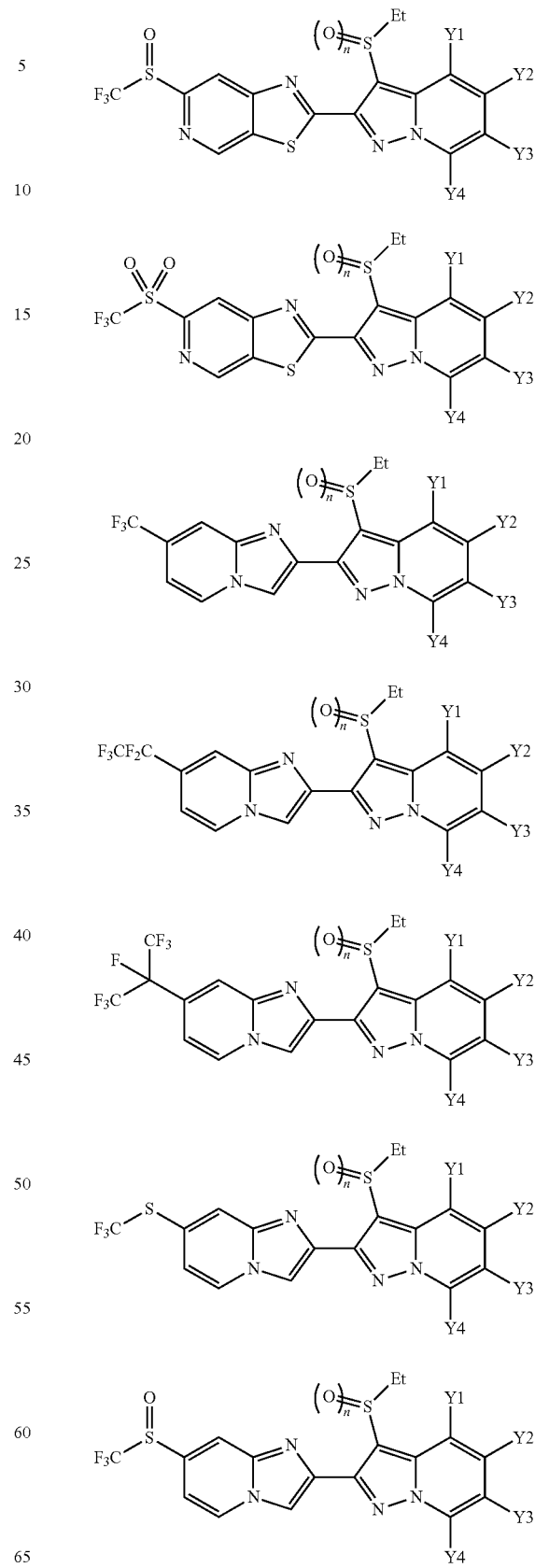

TABLE 1-continued
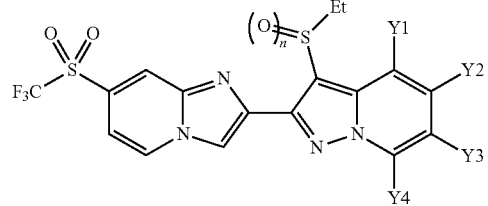
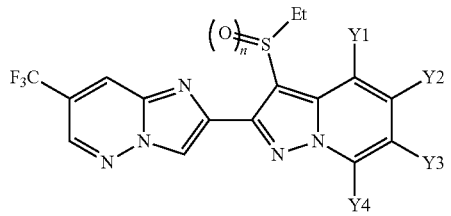
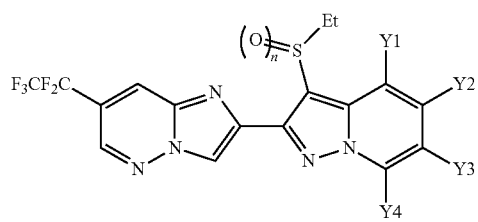
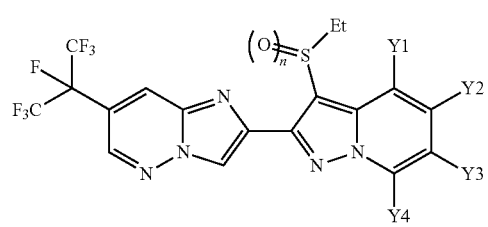
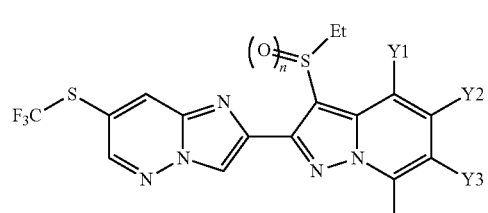
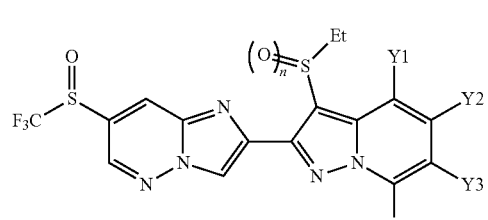
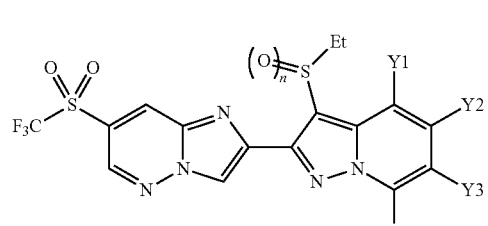
TABLE 1-continued
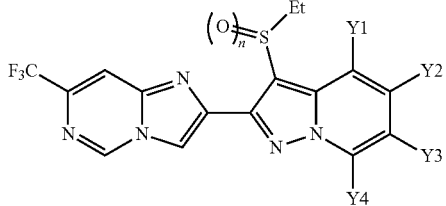
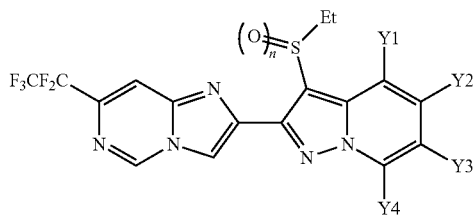
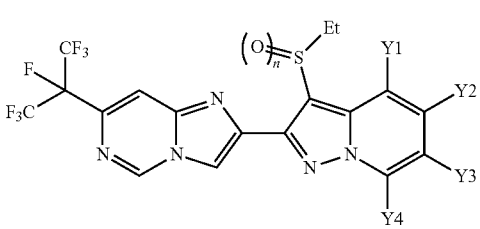
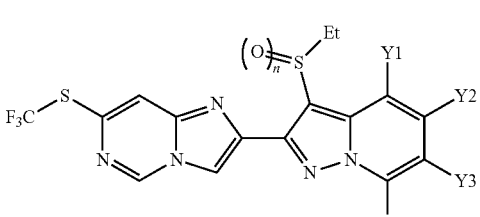
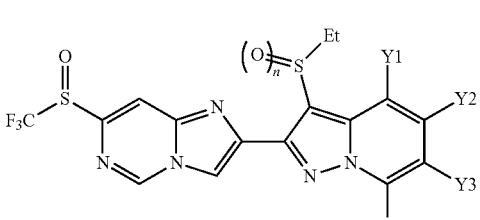
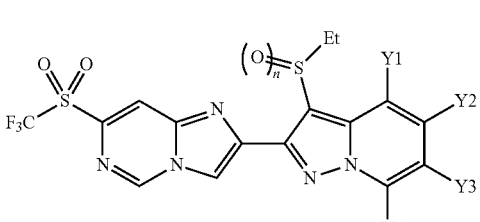
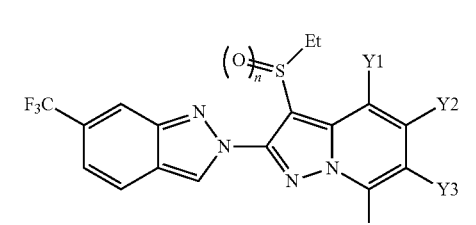

TABLE 1-continued
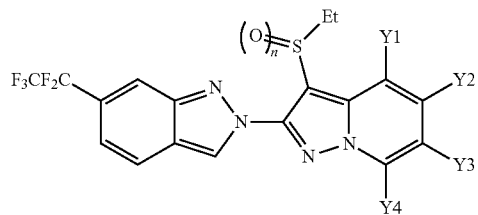
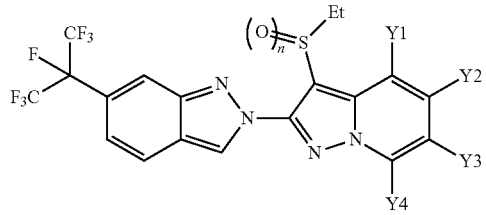
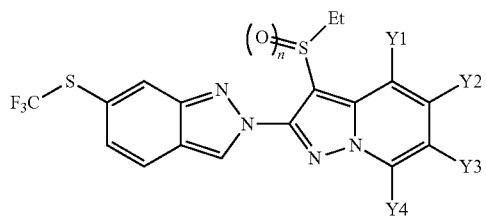
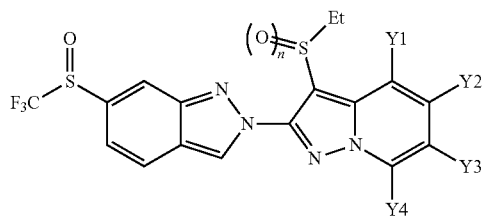
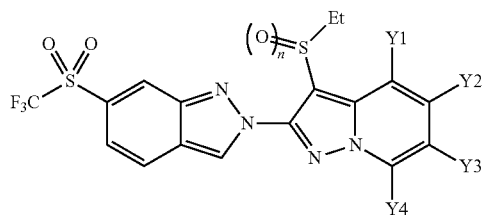
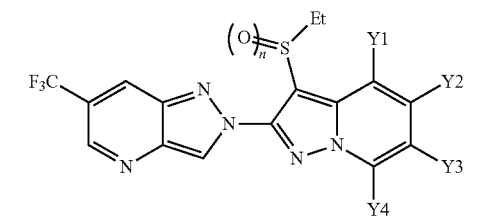
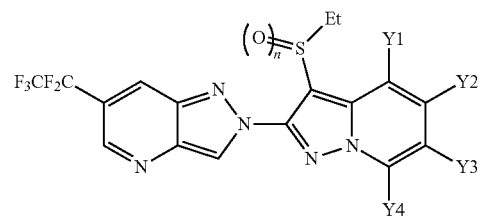
TABLE 1-continued
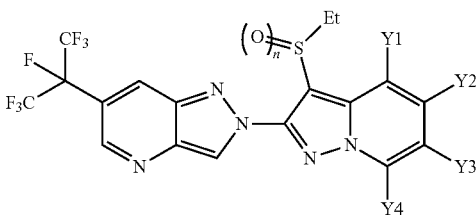
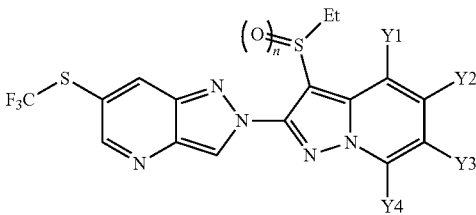
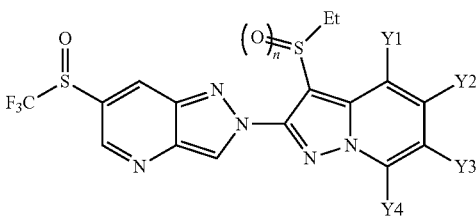
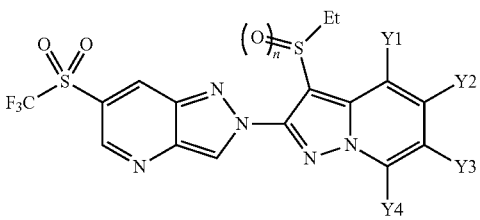
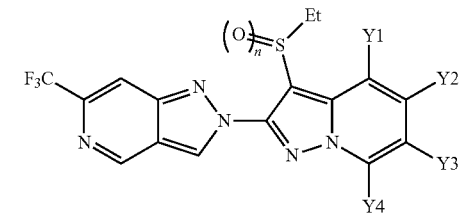
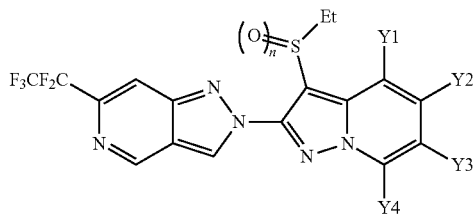
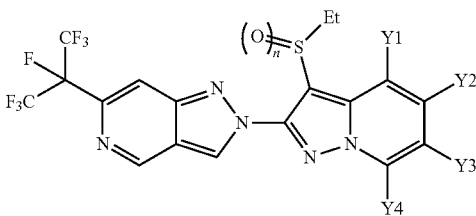

TABLE 1-continued
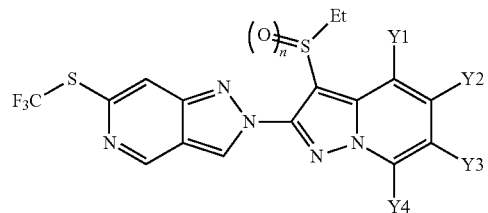
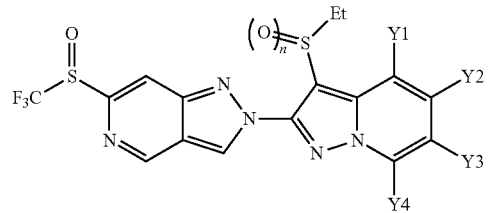
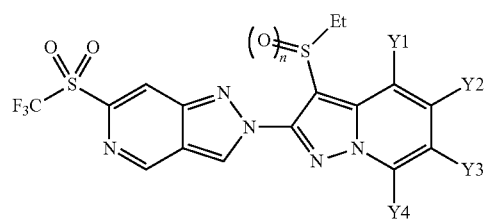
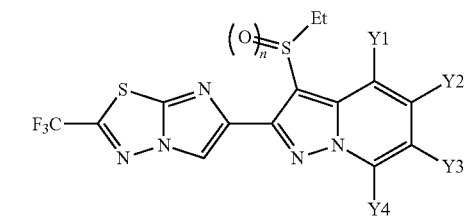
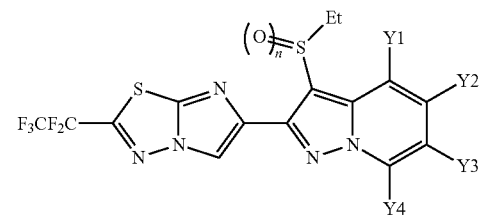
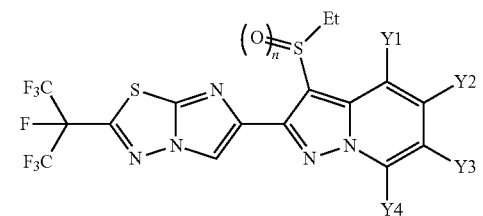
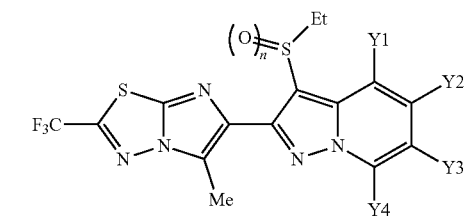
TABLE 1-continued
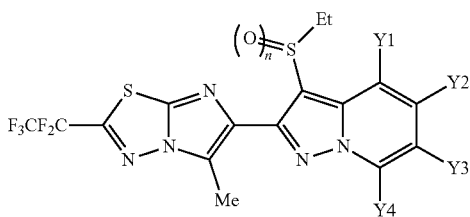
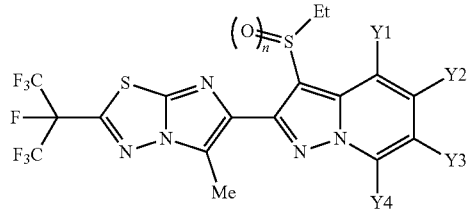
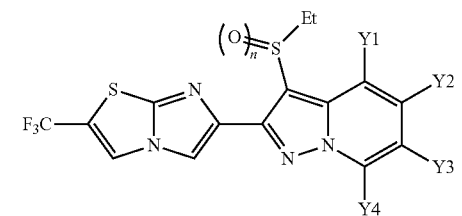
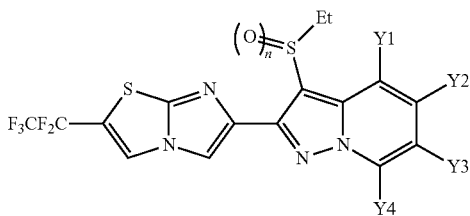
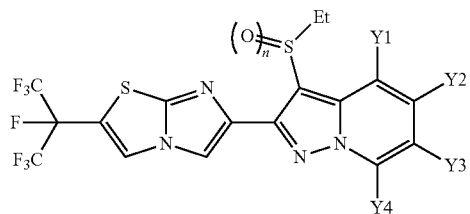
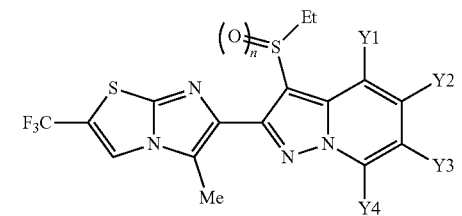
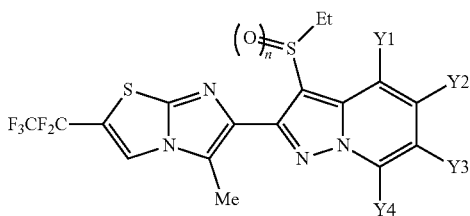

TABLE 1-continued
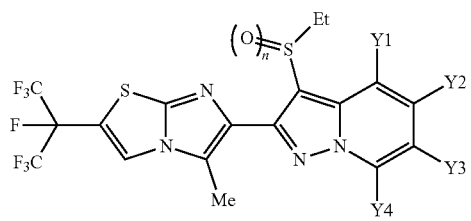
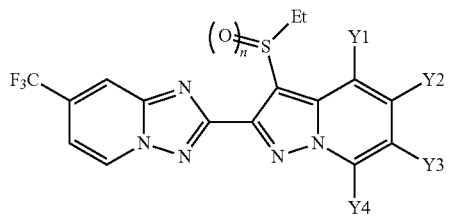
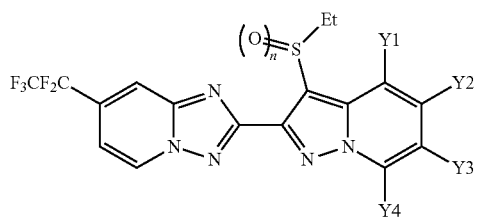
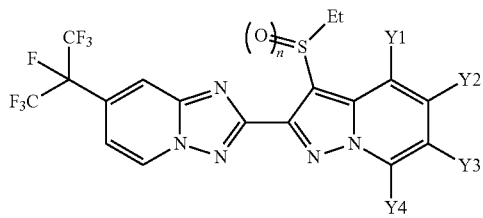
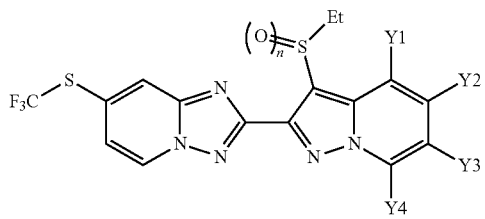
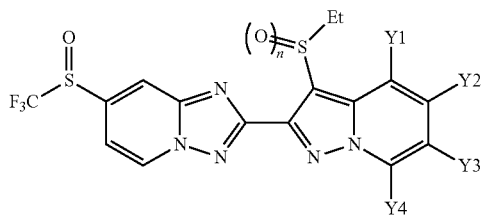
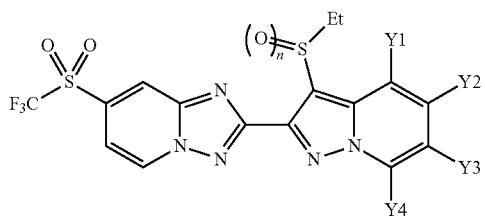
TABLE 1-continued
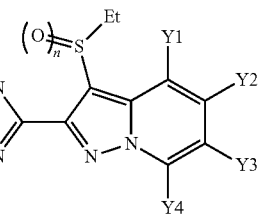
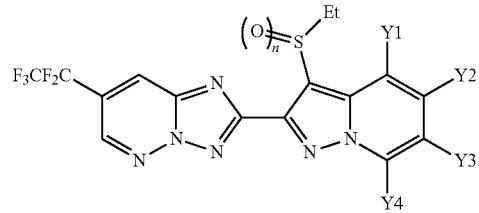
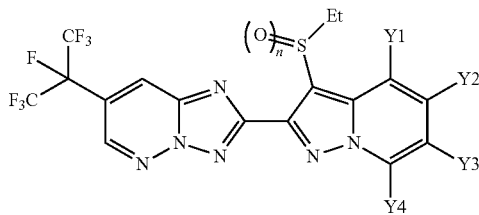
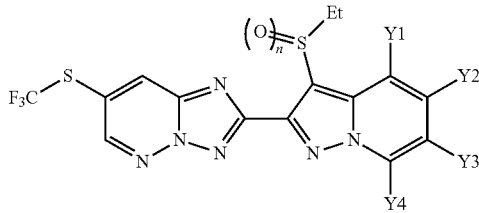
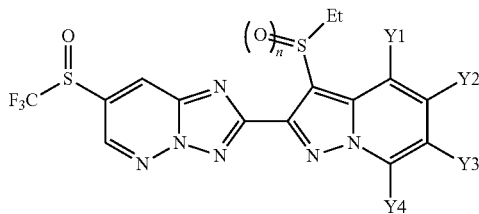
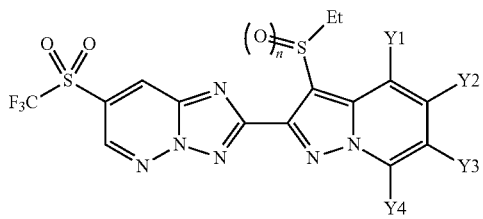
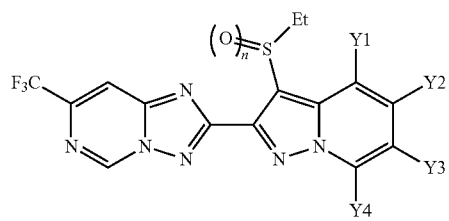

TABLE 1-continued
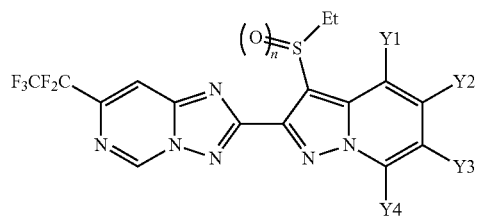
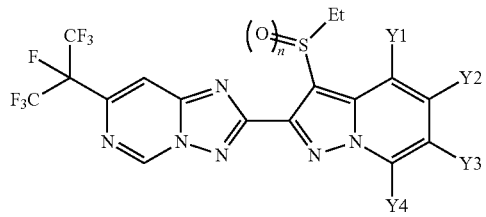
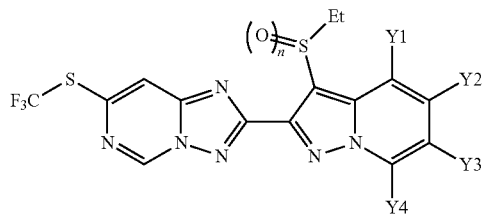
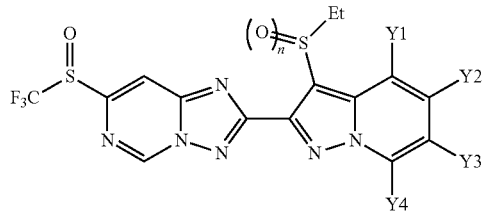
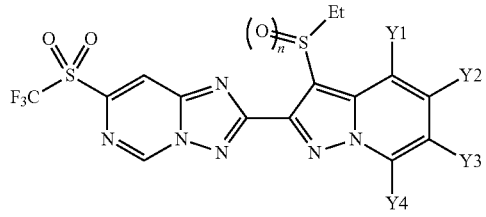
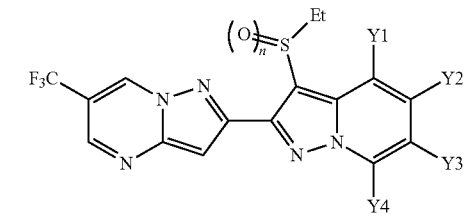
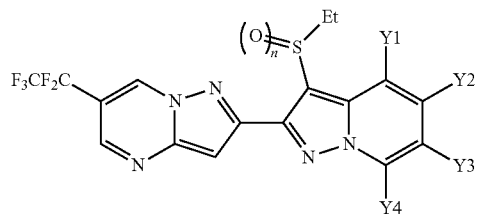
TABLE 1-continued
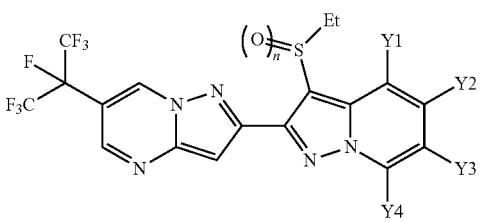
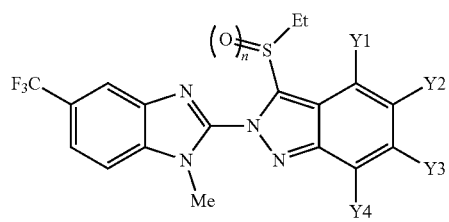
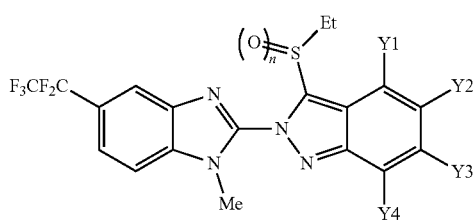
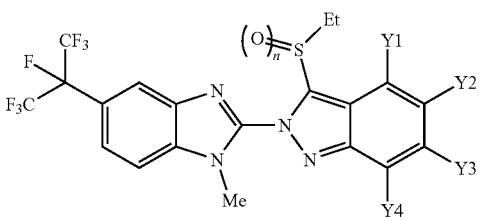
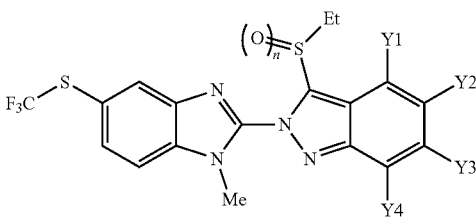
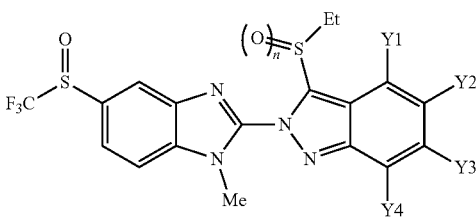
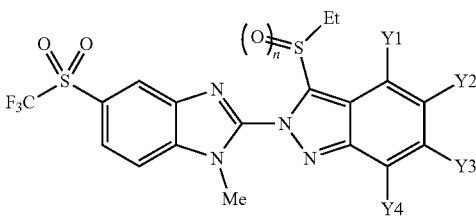

TABLE 1-continued
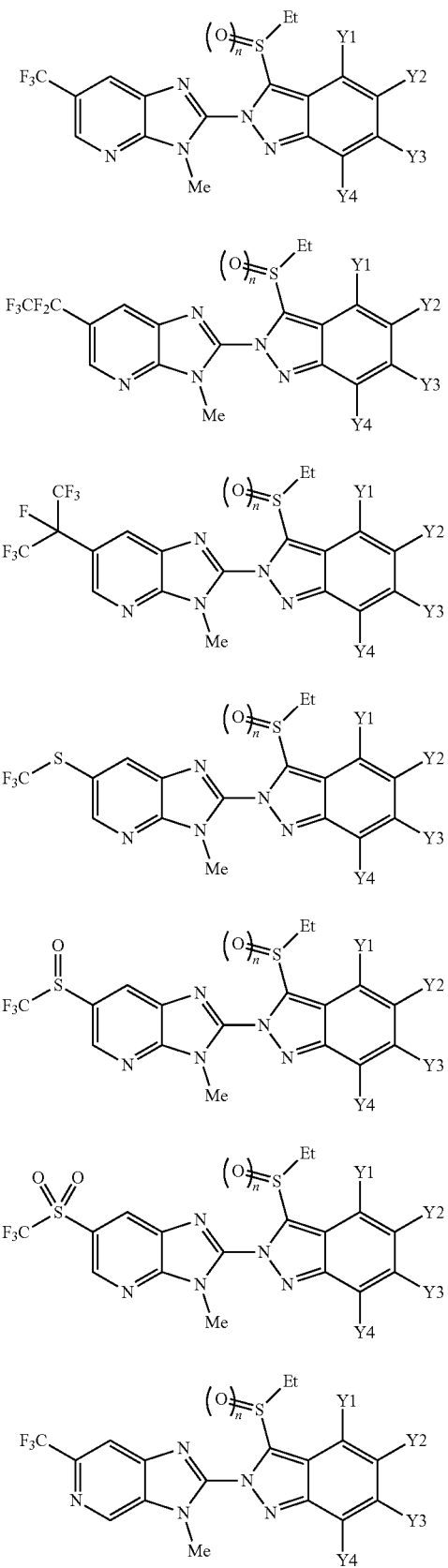
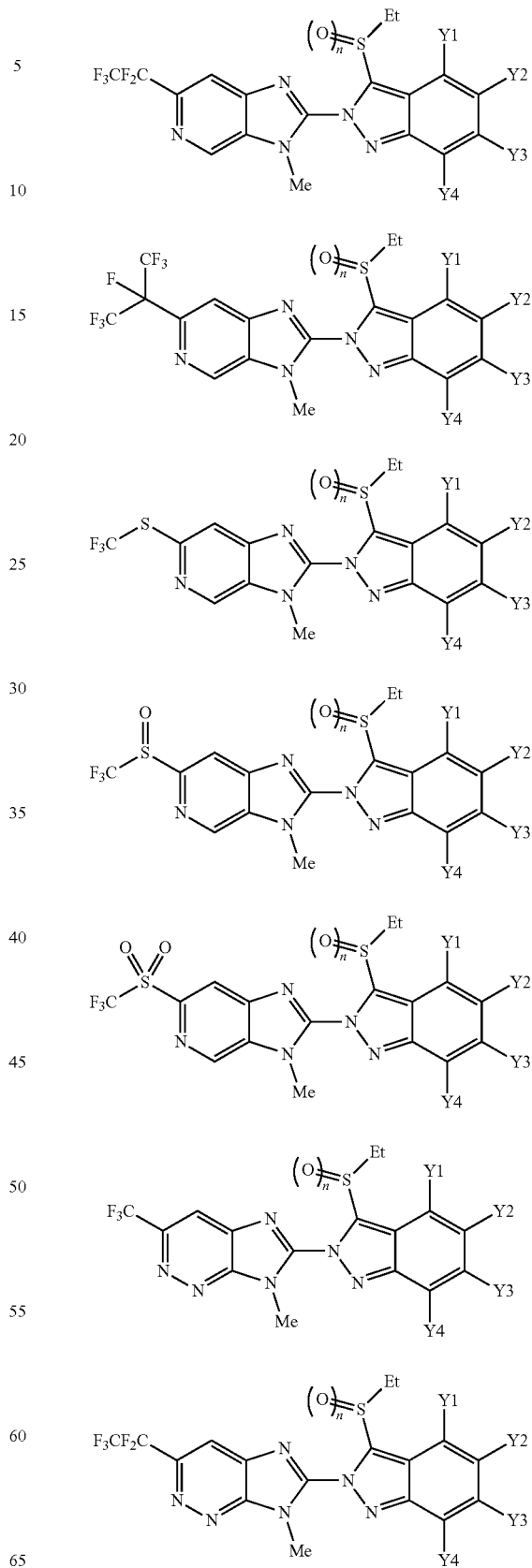

TABLE 1-continued
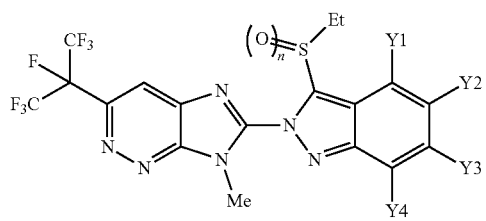
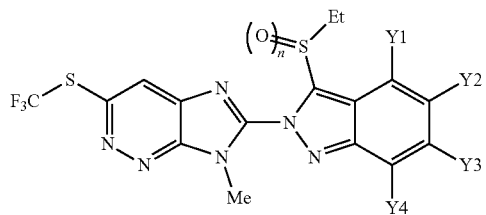
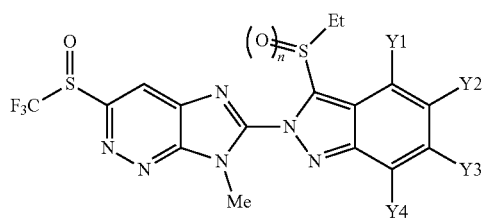
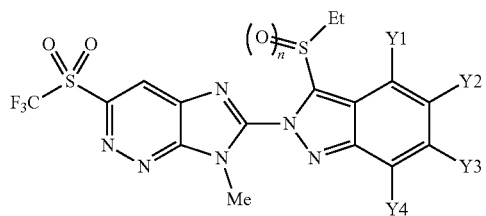
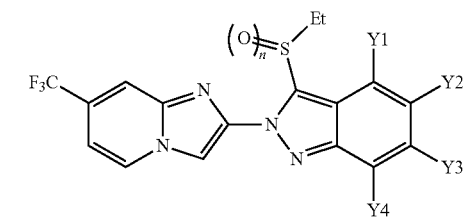
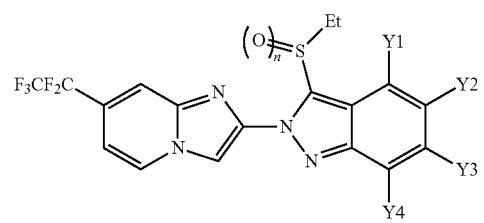
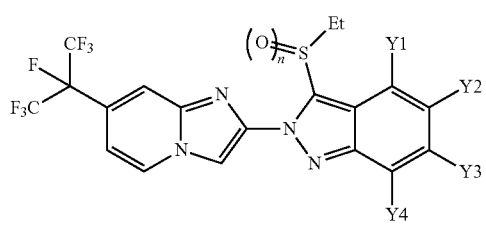
TABLE 1-continued
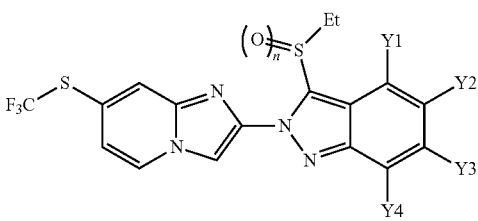
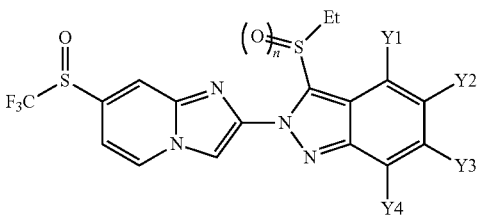
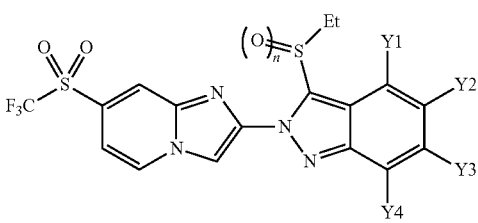
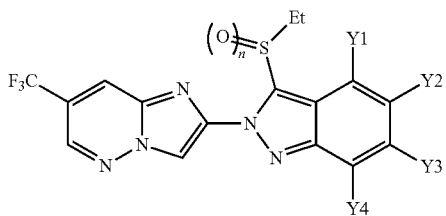
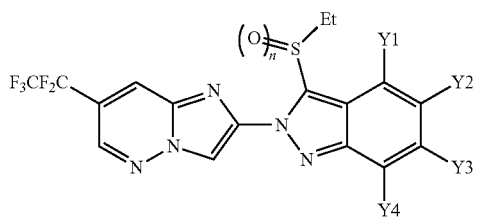
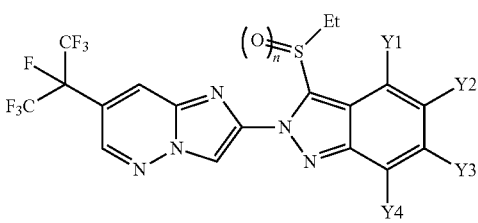
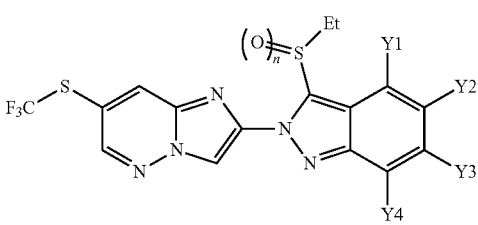

TABLE 1-continued
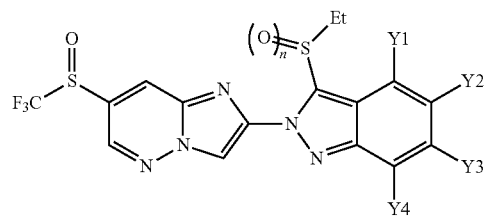
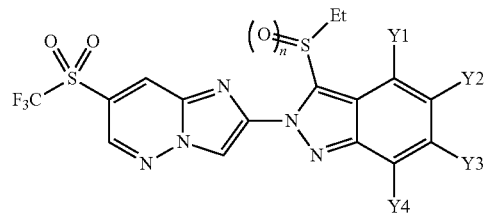
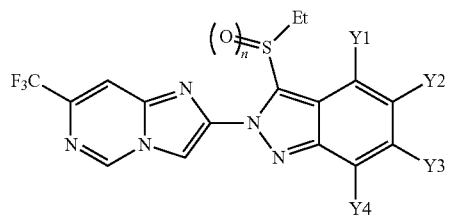
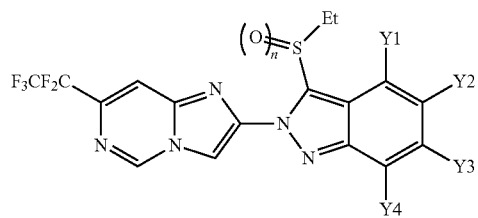
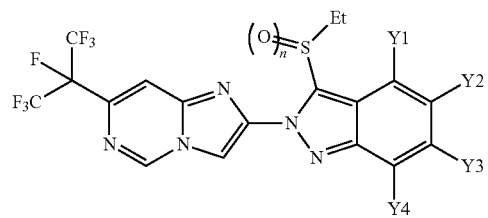
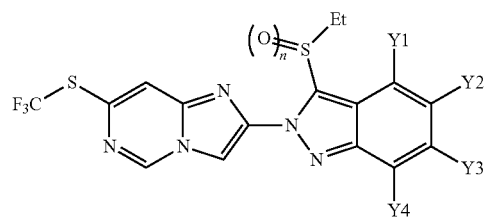
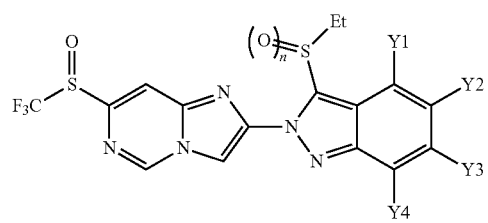
TABLE 1-continued
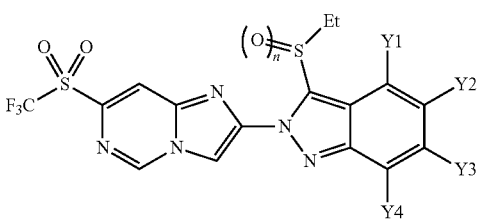
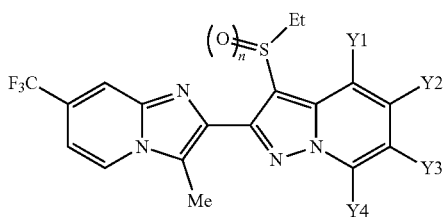
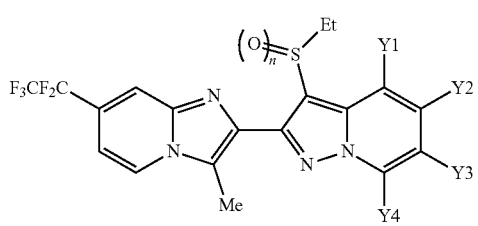
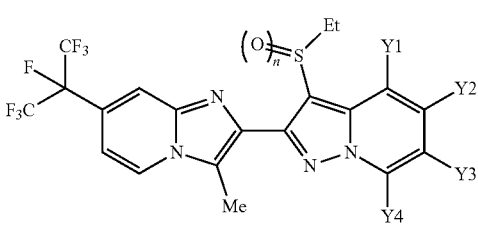
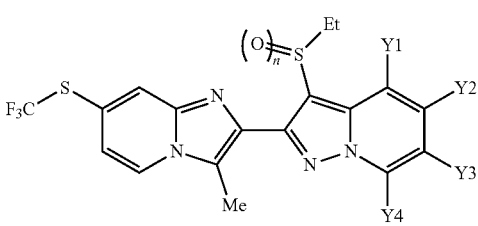
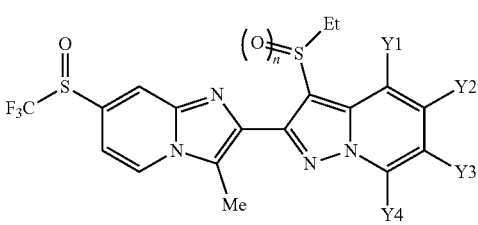
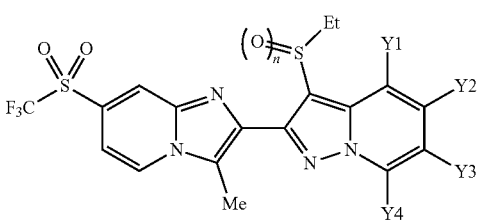

TABLE 1-continued
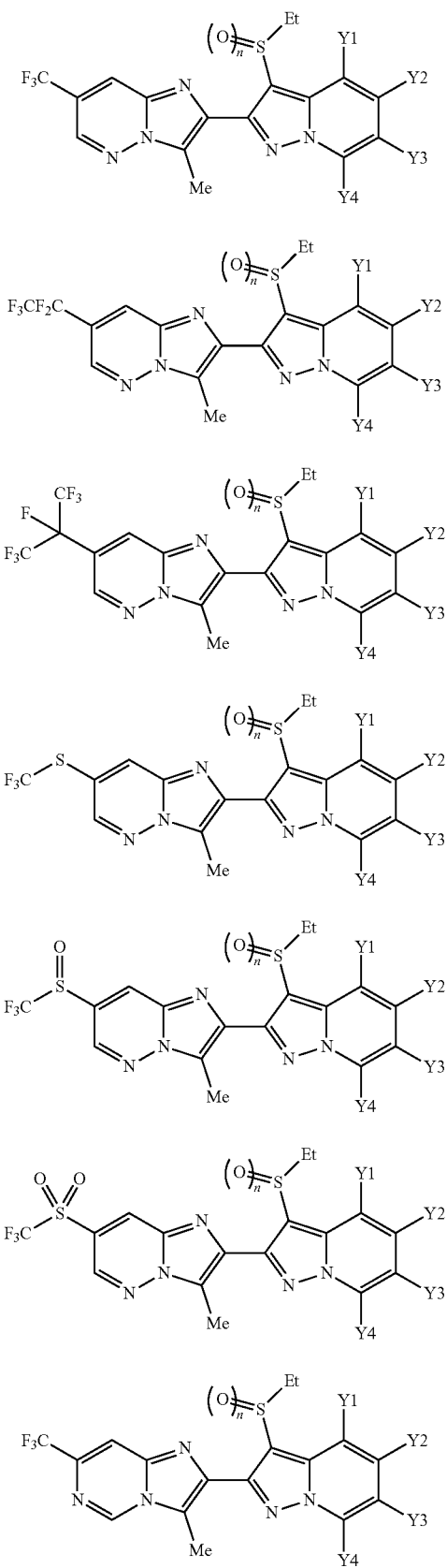
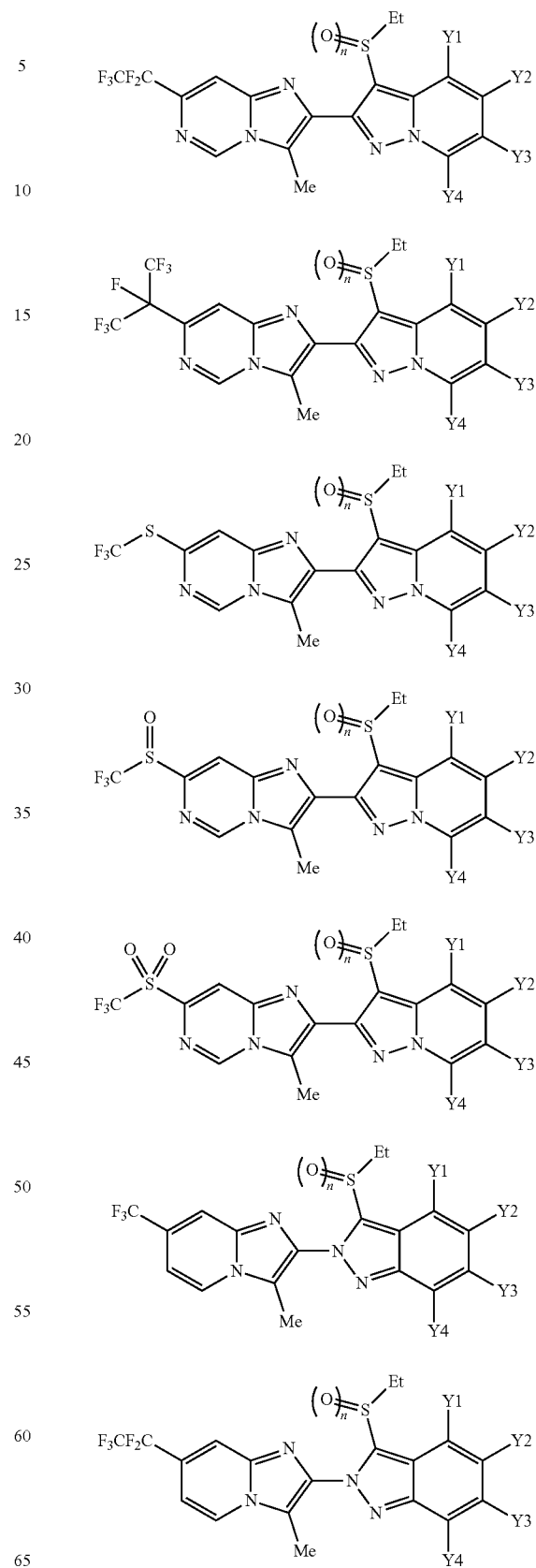

TABLE 1-continued
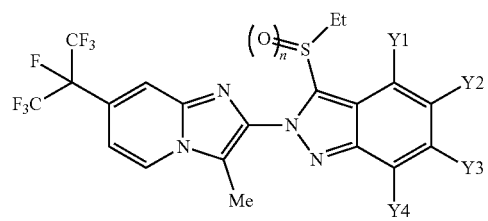
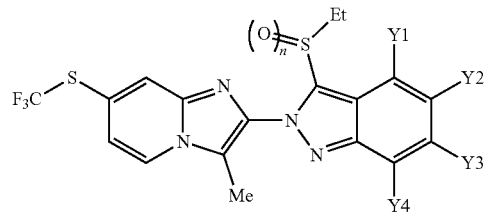
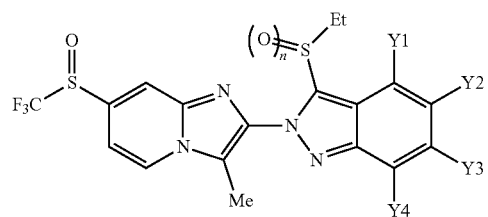
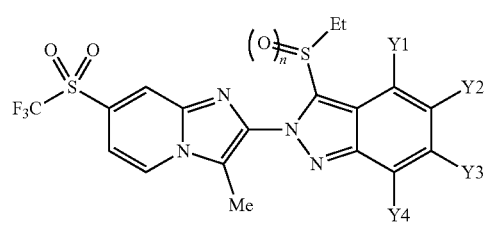
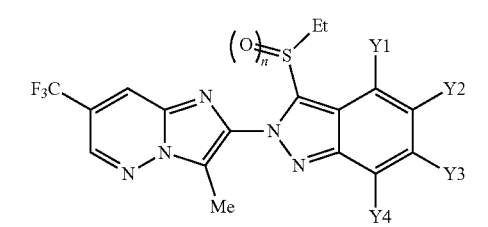
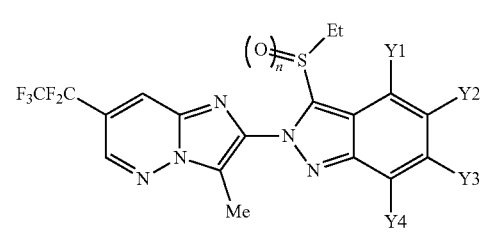
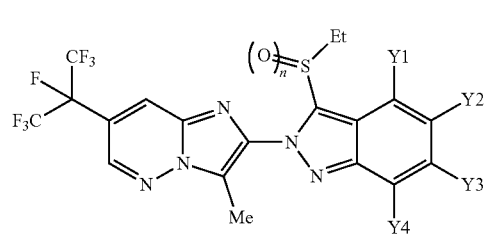
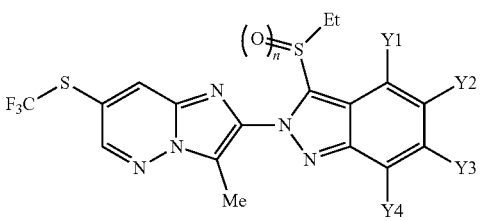
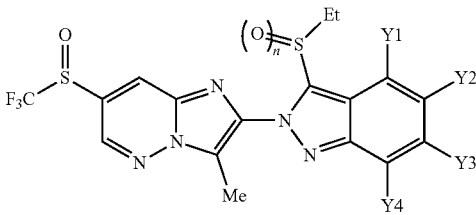
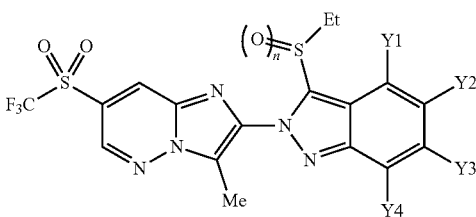
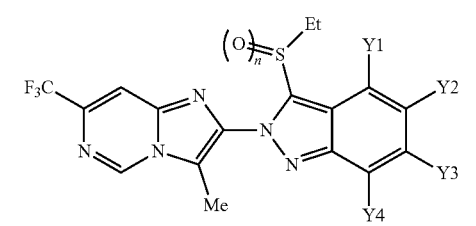
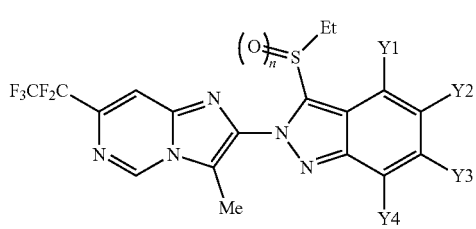
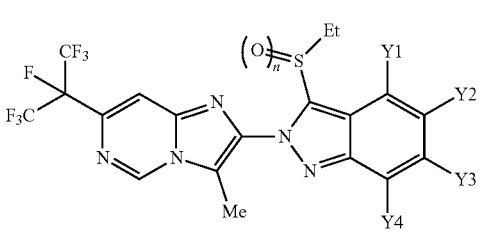
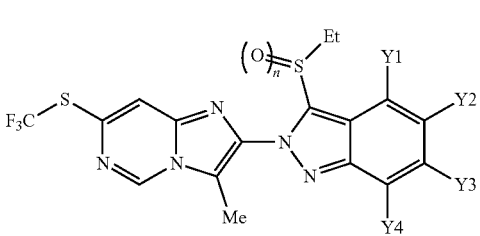

TABLE 1-continued

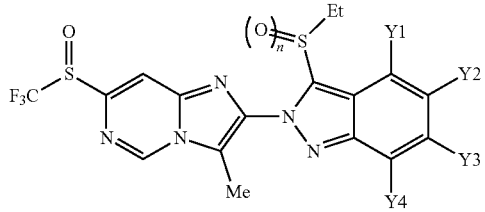

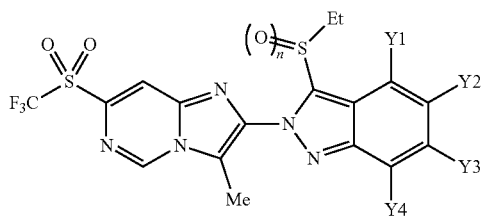

| Y1 | Y2 | Y3 | Y4 | n |
|---|---|---|---|---|
| H | H | H | H | 0 |
| H | H | H | H | 1 |
| H | H | H | H | 2 |
| F | H | H | H | 0 |
| F | H | H | H | 1 |
| F | H | H | H | 2 |
| Cl | H | H | H | 0 |
| Cl | H | H | H | 1 |
| Cl | H | H | H | 2 |
| Br | H | H | H | 0 |
| Br | H | H | H | 1 |
| Br | H | H | H | 2 |
| I | H | H | H | 0 |
| I | H | H | H | 1 |
| I | H | H | H | 2 |
| Me | H | H | H | 0 |
| Me | H | H | H | 1 |
| Me | H | H | H | 2 |
| CF$_3$ | H | H | H | 0 |
| CF$_3$ | H | H | H | 1 |
| CF$_3$ | H | H | H | 2 |
| H | F | H | H | 0 |
| H | F | H | H | 1 |
| H | F | H | H | 2 |
| H | Cl | H | H | 0 |
| H | Cl | H | H | 1 |
| H | Cl | H | H | 2 |
| H | Br | H | H | 0 |
| H | Br | H | H | 1 |
| H | Br | H | H | 2 |
| H | I | H | H | 0 |
| H | I | H | H | 1 |
| H | I | H | H | 2 |
| H | Me | H | H | 0 |
| H | Me | H | H | 1 |
| H | Me | H | H | 2 |
| H | SOCF$_3$ | H | H | 0 |
| H | SOCF$_3$ | H | H | 1 |
| H | SOCF$_3$ | H | H | 2 |
| H | SO$_2$CF$_3$ | H | H | 0 |
| H | SO$_2$CF$_3$ | H | H | 1 |
| H | SO$_2$CF$_3$ | H | H | 2 |
| H | H | F | H | 0 |
| H | H | F | H | 1 |
| H | H | F | H | 2 |
| H | H | Cl | H | 0 |
| H | H | Cl | H | 1 |
| H | H | Cl | H | 2 |
| H | H | Br | H | 0 |
| H | H | Br | H | 1 |
| H | H | Br | H | 2 |
| H | H | I | H | 0 |
| H | H | I | H | 1 |
| H | H | I | H | 2 |
| H | H | Me | H | 0 |
| H | H | Me | H | 1 |
| H | H | Me | H | 2 |
| H | H | CF$_3$ | H | 0 |
| H | H | CF$_3$ | H | 1 |
| H | H | CF$_3$ | H | 2 |
| H | H | CF$_2$CF$_3$ | H | 0 |
| H | H | CF$_2$CF$_3$ | H | 1 |
| H | H | CF$_2$CF$_3$ | H | 2 |
| H | H | CF(CF$_3$)$_2$ | H | 0 |
| H | H | CF(CF$_3$)$_2$ | H | 1 |
| H | H | CF(CF$_3$)$_2$ | H | 2 |
| H | H | SMe | H | 0 |
| H | H | SMe | H | 1 |
| H | H | SMe | H | 2 |
| H | H | SOMe | H | 0 |
| H | H | SOMe | H | 1 |
| H | H | SOMe | H | 2 |
| H | H | H | I | 0 |
| H | H | H | I | 1 |
| H | H | H | I | 2 |
| H | H | H | Me | 0 |
| H | H | H | Me | 1 |
| H | H | H | Me | 2 |
| H | H | H | CF$_3$ | 0 |
| H | H | H | CF$_3$ | 1 |
| H | H | H | CF$_3$ | 2 |
| H | J1 | H | H | 0 |
| H | J1 | H | H | 1 |
| H | J1 | H | H | 2 |
| H | J2 | H | H | 0 |
| H | J2 | H | H | 1 |
| H | J2 | H | H | 2 |
| H | J3 | H | H | 0 |
| H | J3 | H | H | 1 |
| H | J3 | H | H | 2 |
| H | J4 | H | H | 0 |
| H | J4 | H | H | 1 |
| H | J4 | H | H | 2 |
| H | J5 | H | H | 0 |
| H | J5 | H | H | 1 |
| H | J5 | H | H | 2 |
| H | J6 | H | H | 0 |
| H | J6 | H | H | 1 |
| H | J6 | H | H | 2 |
| H | J7 | H | H | 0 |
| H | J7 | H | H | 1 |
| H | J7 | H | H | 2 |
| H | J8 | H | H | 0 |
| H | J8 | H | H | 1 |
| H | J8 | H | H | 2 |
| H | J9 | H | H | 0 |
| H | J9 | H | H | 1 |
| H | J9 | H | H | 2 |
| H | H | J8 | H | 0 |
| H | H | J8 | H | 1 |
| H | H | J8 | H | 2 |
| H | H | J9 | H | 0 |
| H | H | J9 | H | 1 |
| H | H | J9 | H | 2 |
| H | H | J10 | H | 0 |
| H | H | J10 | H | 1 |
| H | H | J10 | H | 2 |
| H | H | J11 | H | 0 |
| H | H | J11 | H | 1 |
| H | H | J11 | H | 2 |
| H | H | J12 | H | 0 |
| H | H | J12 | H | 1 |
| H | H | J12 | H | 2 |
| H | H | J13 | H | 0 |
| H | H | J13 | H | 1 |
| H | H | J13 | H | 2 |
| H | H | J14 | H | 0 |
| H | H | J14 | H | 1 |
| H | H | J14 | H | 2 |
| H | H | H | J1 | 0 |
| H | H | H | J1 | 1 |
| H | H | H | J1 | 2 |
| H | H | H | J2 | 0 |
| H | H | H | J2 | 1 |
| H | H | H | J2 | 2 |
| H | H | H | J3 | 0 |

TABLE 1-continued

| | | | | |
|---|---|---|---|---|
| H | H | H | J3 | 1 |
| H | H | H | J3 | 2 |
| H | H | H | J4 | 0 |
| H | H | H | J4 | 1 |
| H | H | H | J4 | 2 |
| H | H | H | J5 | 0 |
| H | H | H | J5 | 1 |
| H | H | H | J5 | 2 |
| H | CF$_3$ | H | H | 0 |
| H | CF$_3$ | H | H | 1 |
| H | CF$_3$ | H | H | 2 |
| H | CF$_2$CF$_3$ | H | H | 0 |
| H | CF$_2$CF$_3$ | H | H | 1 |
| H | CF$_2$CF$_3$ | H | H | 2 |
| H | CF(CF$_3$)$_2$ | H | H | 0 |
| H | CF(CF$_3$)$_2$ | H | H | 1 |
| H | CF(CF$_3$)$_2$ | H | H | 2 |
| H | SMe | H | H | 0 |
| H | SMe | H | H | 1 |
| H | SMe | H | H | 2 |
| H | SOMe | H | H | 0 |
| H | SOMe | H | H | 1 |
| H | SOMe | H | H | 2 |
| H | SO$_2$Me | H | H | 0 |
| H | SO$_2$Me | H | H | 1 |
| H | SO$_2$Me | H | H | 2 |
| H | OMe | H | H | 0 |
| H | OMe | H | H | 1 |
| H | OMe | H | H | 2 |
| H | OCF$_3$ | H | H | 0 |
| H | OCF$_3$ | H | H | 1 |
| H | OCF$_3$ | H | H | 2 |
| H | NO$_2$ | H | H | 0 |
| H | NO$_2$ | H | H | 1 |
| H | NO$_2$ | H | H | 2 |
| H | NH$_2$ | H | H | 0 |
| H | NH$_2$ | H | H | 1 |
| H | NH$_2$ | H | H | 2 |
| H | CN | H | H | 0 |
| H | CN | H | H | 1 |
| H | CN | H | H | 2 |
| H | SCF$_3$ | H | H | 0 |
| H | SCF$_3$ | H | H | 1 |
| H | SCF$_3$ | H | H | 2 |
| H | H | SO$_2$Me | H | 0 |
| H | H | SO$_2$Me | H | 1 |
| H | H | SO$_2$Me | H | 2 |
| H | H | OMe | H | 0 |
| H | H | OMe | H | 1 |
| H | H | OMe | H | 2 |
| H | H | OCF$_3$ | H | 0 |
| H | H | OCF$_3$ | H | 1 |
| H | H | OCF$_3$ | H | 2 |
| H | H | NO$_2$ | H | 0 |
| H | H | NO$_2$ | H | 1 |
| H | H | NO$_2$ | H | 2 |
| H | H | NH$_2$ | H | 0 |
| H | H | NH$_2$ | H | 1 |
| H | H | NH$_2$ | H | 2 |
| H | H | CN | H | 0 |
| H | H | CN | H | 1 |
| H | H | CN | H | 2 |
| H | H | SCF$_3$ | H | 0 |
| H | H | SCF$_3$ | H | 1 |
| H | H | SCF$_3$ | H | 2 |
| H | H | SOCF$_3$ | H | 0 |
| H | H | SOCF$_3$ | H | 1 |
| H | H | SOCF$_3$ | H | 2 |
| H | H | SO$_2$CF$_3$ | H | 0 |
| H | H | SO$_2$CF$_3$ | H | 1 |
| H | H | SO$_2$CF$_3$ | H | 2 |
| H | H | H | F | 0 |
| H | H | H | F | 1 |
| H | H | H | F | 2 |
| H | H | H | Cl | 0 |
| H | H | H | Cl | 1 |
| H | H | H | Cl | 2 |
| H | H | H | Br | 0 |
| H | H | H | Br | 1 |
| H | H | H | Br | 2 |
| H | J10 | H | H | 0 |
| H | J10 | H | H | 1 |
| H | J10 | H | H | 2 |
| H | J11 | H | H | 0 |
| H | J11 | H | H | 1 |
| H | J11 | H | H | 2 |
| H | J12 | H | H | 0 |
| H | J12 | H | H | 1 |
| H | J12 | H | H | 2 |
| H | J13 | H | H | 0 |
| H | J13 | H | H | 1 |
| H | J13 | H | H | 2 |
| H | J14 | H | H | 0 |
| H | J14 | H | H | 1 |
| H | J14 | H | H | 2 |
| H | H | J1 | H | 0 |
| H | H | J1 | H | 1 |
| H | H | J1 | H | 2 |
| H | H | J2 | H | 0 |
| H | H | J2 | H | 1 |
| H | H | J2 | H | 2 |
| H | H | J3 | H | 0 |
| H | H | J3 | H | 1 |
| H | H | J3 | H | 2 |
| H | H | J4 | H | 0 |
| H | H | J4 | H | 1 |
| H | H | J4 | H | 2 |
| H | H | J5 | H | 0 |
| H | H | J5 | H | 1 |
| H | H | J5 | H | 2 |
| H | H | J6 | H | 0 |
| H | H | J6 | H | 1 |
| H | H | J6 | H | 2 |
| H | H | J7 | H | 0 |
| H | H | J7 | H | 1 |
| H | H | J7 | H | 2 |
| H | H | H | J6 | 0 |
| H | H | H | J6 | 1 |
| H | H | H | J6 | 2 |
| H | H | H | J7 | 0 |
| H | H | H | J7 | 1 |
| H | H | H | J7 | 2 |
| H | H | H | J8 | 0 |
| H | H | H | J8 | 1 |
| H | H | H | J8 | 2 |
| H | H | H | J9 | 0 |
| H | H | H | J9 | 1 |
| H | H | H | J9 | 2 |
| H | H | H | J10 | 0 |
| H | H | H | J10 | 1 |
| H | H | H | J10 | 2 |
| H | H | H | J11 | 0 |
| H | H | H | J11 | 1 |
| H | H | H | J11 | 2 |
| H | H | H | J12 | 0 |
| H | H | H | J12 | 1 |
| H | H | H | J12 | 2 |
| H | H | H | J13 | 0 |
| H | H | H | J13 | 1 |
| H | H | H | J13 | 2 |
| H | H | H | J14 | 0 |
| H | H | H | J14 | 1 |
| H | H | H | J14 | 2 |
| H | Br | H | CN | 0 |
| H | Br | H | CN | 1 |
| H | Br | H | CN | 2 |
| H | I | H | CN | 0 |
| H | I | H | CN | 1 |
| H | I | H | CN | 2 |
| H | Br | H | F | 0 |
| H | Br | H | F | 1 |
| H | Br | H | F | 2 |

The pesticides herein mean pesticides for controlling harmful arthropods in agricultural fields or in zootechnical/hygienic fields (internal/external parasites in or on mammals and birds as livestock and pets, and domestic or industrial hygienic insects/nuisance insects).

Further, the agricultural chemicals herein mean insecticides/acaricides, nematicides, herbicides and fungicides in agricultural fields.

The hygienic insects in this specification mean harmful invertebrates which cause allergic symptoms such as severe pain, swelling or itching by biting the object animals and in some cases, cause fatal anaphylactic shock, sometimes transmit severe diseases due to blood sucking and in some cases, cause death, invertebrates which contaminate food with pathogens such as viruses, bacteria or parasites by being in contact with the food, invertebrates which cause allergic diseases such as bronchitic asthma, rhinitis, conjunctivitis or atopic dermatitis, by their living bodies, dead bodies, exuviate, droppings, etc., as allergens, invertebrates which cause feeding damages on food, clothes and housing thereby to cause economic damages, invertebrates which do not cause direct damages but create discomfort by emergence/infestation in human living environment, etc. More specifically, the hygienic insects mean ants which bite by mandibles, hornets which have a poisonous sting, mosquitos and kissing bugs which suck blood through the skin, and omnivorous termites which harm buildings such as houses.

The nuisance insects in this specification mean insects which create discomfort due to their appearances and cause physiological damages to human although they do not cause direct damages to human in the human living environment.

The insects, mites, crustaceans, mollusks and nematodes that the compounds of the present invention can control specifically include the following organisms, but the present invention is not restricted thereto.

Insects of the order Lepidoptera such as Adoxophyes honmai, Adoxophyes orana faciata, Archips breviplicanus, Archips fuscocupreanus, Grapholita molesta, Homona magnanima, Lequminivora glycinivorella, Matsumuraeses phaseoli, Pandemis heparana, Bucculatrix pyrivorella, Bucculatrix thurberiella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Lyctus brunnus, Carposina sasakii, Sinoxylon laponicum, Rhizopertha dominica, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara uttata, Pieris brassicae, Pieris rapae crucivora, Ascotis selenaria, Pseudoplusia includens, Euproctis pseudoconspersa, Artaxa subflava, Sphrageidus similis, Euproctis Dierita, Lymantria dispar, Orgyia thyellina, Gastropachaorientalis, Dendrolimus spectabilis, Dendrolimus superans, Kunugia undans, Arctia caia phaeosoma, Chionarctia nivea, Hyphantria cunea, Lemyra imparilis, Monema flavescens, Phrixolepia sericea, Parsa sinica, Parsa lepida, Adris tyrannus, Aedia leucomelas, Agrotis isilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodoptera exiqua, Spodoptera frugiperda, Spodoptera littoralis, Spodoptera litura, Spodoptera depravata, Trichoplusia ni, Endopiza viteana, Manduca quinquemaculata, Manduca sexta, Clysia ambiguella, Eupoecilia ambiguella, Acronicta major, Amyelois transitella, Borbo cinnara, Bupalus piniarius, Capua reticulana, Cheimatobia brumata, Diatraea saccharalis, Ecdytolopha aurantiana, Elasmopalpus lignosellus, Eldana saccharina, Epiphyas postvittana, Galleria mellonella, Hofmannophila pseudospretella, Yponomeuta padella, Leucinodes orbonalis, Lithophane antennata, Loxagrotis albicosta, Malacosoma neustria, Maruca testulalis, Platynota stultana, Rachiplusia nu, Scotia segetum, Stomopteryx subsecivella, Tecia solanivora, Thermesia gemmatalis, Tinea pellionella, Tineola bisselliella and *Tuta absoluta.*

Insects of the order Thysanoptera such as *Frankliniella intonsa, Frankliniella occidentalis, Heliothrips haemorrhoidalis, Scirtothrips dorsalis, Thrips palmi, Thrips tabaci* and *Ponticulothrips diospyrosi.*

Insects of the order Heteroptera such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cinqulatus, Stephanitis pyrioides, Halticus insularis, Lygus lineolaris, Stenodema sibiricum, Stenotus rubrovittatus, Trigonotylus caelestialium, Anasa tristis, Campylomma livida, Creontiades dilutus, Dasynus piperis, Dichelops furcatus, Diconocoris hewett, Horcias nobilellus, Leptoglossus phyllopus, Macropes excavatus, Monalonion atratum, Piesma quadrata, Sahlbergella sinqularis, Scaptocoris castanea, Pseudacysta persea* and *Stephanitis nashi.*

Insects of the order Hemiptera such as *Arboridia apicalis, Balclutha saltuella, Epiacanthus stramineus, Empoasca fabae, Empoasca nipponica, Empoasca onukii, Empoasca sakaii, Macrosteles striifrons, Nephotettix cinctinceps, Bothrogonia ferruginea, Psuedatomoscelis seriatus, Laodelphax striatella, Nilaparvata lugens, Sogatella furcifera, Diaphorina citri, Psvlla Dyrisuga, Aleurocanthus spiniferus, Bemisia argentifolii, Bemisia tabaci, Dialeurodes citri, Trialeurodes vaporariorum, Viteus vitifolii, Aphis ossypii, Aphis spiraecola, Myzus persicae, Toxoptera aurantii, Drosicha corpulenta, Icerva purchasi, Phenacoccus solani, Planococcus citri, Planococcus kuraunhiae, Pseudococcus comstocki, Ceroplastes ceriferus, Ceroplastes rubens, Aonidiella aurantii, Comstockaspis perniciosa, Fiorinia theae, Pseudaonidia paeoniae, Pseudaulacaspis pentagona, Pseudaulacaspis prunicola, Unaspis euonymi, Unaspis yanonensis* and *Cimex lectularius.*

Insects of the order Coleoptera such as *Anomala cuprea, Anomala rufocuprea, Gametis lucunda, Heptophylla picea, Popillia japonica, Lepinotarsa decemlineata, Melanotus fortnumi, Melanotus tamsuyensis, Stegobium paniceum, Lasioderma serricorne, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus* and *Paederus fuscipes.*

Insects of the order Diptera such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Pegomya cunicularia, Rhagoletis pomonella, Mayetiola destructor, Musca domestica, Stomoxys calcitrans, Melophagus ovinus, Hypoderma* bovis, Hypoderma lineatum, Oestrus ovis, Glossina palpalis, Glossina morsitans, Prosimulium yezoensis, Tabanus trigonus, Telmatoscopus albipunctatus, Leptoconops nipponensis, Culex pipiens pallens, Aedes aepgyti, Aedes albopicutus, Anopheles hyracanus sinesis, Aedes akkeshiensis, Aedes albocinctus, Aedes alboscutellatus, Aedes atriisimilis, Aedes baisasi, Aedes bekkui, Aedes communis, Aedes daitensis, Aedes diantaeus, Aedes dorsalis, Aedes ezoensis, Aedes excrucians, Aedes flavopictus, Aedes alloisi, Aedes hakusanensis, Aedes hatorii, Aedes hokkaidensis, Aedes impiger daisetsuzanus, Aedes intrudens, Aedes iriomotensis, Aedes iaponicus, Aedes kobayashii, Aedes koreicoides, Aedes lineatopennis, Aedes nipponicus, Aedes nishikawai, Aedes nobukonis, Aedes okinawanus, Aedes oreophilus, Aedes punctor, Aedes reversi, Aedes sasai, Aedes savo ri, Aedes seoulensis, Aedes sticticus, Aedes tooi, Aedes vexans nipponii, Aedes vi ilax, Aedes wadai, Aedes watasei, Aedes yamadai, Anopheles bengalensis, Anopheles engarensis, Anopheles koreicus, Anopheles lesteri, Anopheles lindesayi japonicus, Anopheles minimus, Anopheles omorii, Anopheles saperoi, Anopheles sineroides, Anopheles tessellatus, Anopheles yatsushiroensis, Armigeres subalbatus, Culex bicornutus, Culex bitaeniorhynchus, Culex boninensis, Culex brevipalpis, Culex cinctellus, Culex fuscocephala, Culex hayashii, Culex infantulus, Culex iacksoni, Culex kyotoensis, Culex mimeticus, Culex modestus inatomii, Culex nigropunctatus, Culex okinawae, Culex orientalis, Culex pallidothorax, Culex iiens molestus, Culex pipiens quinquefasciatus, Culex pseudovishnui, Culex rubensis, Culex rubithoracis, Culex ryukyensis, Culex sasai, Culex sinensis, Culex sitiens, Culex tritaeniorhynchus, Culex tuberis, Culex vagans, Culex vishnui, Culex whitmorei, Chironomus plumosus and Chironomus riparius.

Insects of the order Hymenoptera such as Apethymus kuri, Athalia rosae, Arge pagana, Neodiprion sertifer, Dryocosmus kuriphilus, Eciton burchelli, Eciton schmitti, Camponotus laponicus, Vespa mandarina, Myrmecia spp., Solenopsis spp., Monomorium pharaonis, Tetramorium tsushimae, Lasius japonicus, Pachycondyla chinensis, Lasius fuliginosus, Formica fusca japonica, Ochetellus laber, Pristomyrmex pungens, Pheidole noda, Pheidole fervida, Linepithema humile and Cephalonomia gallicola.

Insects of the order Orthoptera such as Teleooryllus emma, Loxoblemmus campestris, Gryllotalpa orientalis, Locusta migratoria, Oxya yezoensis, Schistocerca gregaria and Diestrammena apicalis.

Insects of the order Collembola such as Onychiurus folsomi, Onychiurus sibiricus and Bourletiella hortensis.

Insects of the order Dictyoptera such as Periplaneta fuliginosa, Periplaneta japonica, Blattella germanica and Periplaneta australasiae.

Insects of the order Isoptera such as Coptotermes formosanus, Reticulitermes speratus, Odontotermes formosanus, Cornitermes cumulans and Microtermes obesi.

Insects of the order Siphonaptera such as Ctenocephalidae felis, Ctenocephalides canis, Echidnophaga gallinacea, Pulex irritans and Xenopsylla cheopis.

Insects of the order Mallophage such as Menacanthus stramineus and Bovicola bovis.

Insects of the order Anoplura such as Haematopinus eurysternus, Haematopinus suis, Linognathus vituli and Solenopotes capillatus.

Insects of the order Thysanura such as Lepisma saccharina.

Insects of the order Psocoptera such as Psococerastis tokyoensis and Lonovalvus nubilus.

Insects of the order Anisolabididae such as Gonolabis marginalis.

Insects of the order Araneae such as Pardosa astrigera, Chiracanthium iaponicum and Latrodectus hasseltii.

Tarsonemidae mites such as Phytonemus pallidus, Polyphagotarsonemus latus and Tarsonemus bilobatus.

Eupodidae mites such as Penthaleus erythrocephalus and Penthaleus major.

Tetranychidae mites such as Oligonychus shinkaiii, Panonychus citri, Panonychus mori, Panonychus ulmi, Tetranychus kanzawai and Tetranychus urticae.

Eriophyidae mites such as Acaphylla theavagrans, Aceria tulipae, Aculops lycopersici, Aculops pelekassi, Aculus schlechtendali, Eriophyes chibaensis and Phyllocoptruta oleivora.

Acaridae mites such as Rhizoglyphus robini, Tyrophagus putrescentiae and Tyrophagus similis.

Varroa mites such as Varroa iacobsoni.

Ticks such as Boophilus microplus, Rhipicephalus sanguineus, Haemaphysalis longicornis, Haemophysalis flava, Haemophysalis campanulata, Ixodes ovatus, Ixodes persulcatus, Amblyomma spp. and Dermacentor spp.

Mites of the suborder Mesostigmata such as red mite (Dermanyssus gallinae), tropical rat mite (Ornithonyssus bacoti) and northern fowl mite (Ornithonyssus sylviarum).

Cheyletidae mites such as Cheyletiella asuri and Cheyletiella blakei.

Demodicidae mites such as Demodex canis and Demodex cati.

Psoroptidae mites such as Psoroptes ovis.

Sarcoptidae mites such as Sarcoptes scabiei, Notoedres cati and Knemidocoptes spp.

Crustaceans of the order Isopoda such as Armadillidium vulgare, Oniscus asellus and Porcellio scaber.

Crustaceans of the order Arguloida such as Arqulus iaponicus and Arqulus coregoni.

Crustaceans of the order Shphonostomatoida such as Lepeophtheirus salmonis and Salmincola spp.

Crustaceans of the order Cyclopoida such as Lernaea cyprinacea.

Centipedes of the class Chilopoda, the order Scolopendromorpha such as Scolopendra subspinipes, Scolopendra iaponica and Scolopendra multidens, the order Lithobiomorpha such as Bothropolys asperatus, and the order Scutigeromorpha such as Thereuonema hilgendorfi.

Millipedes of the class Diplopoda such as Oxidus racilis, Prafontaria laminata armigera and Nedyopus tambanus.

Symphylans of the class Symphyla such as Scutigerella immaculate.

Gastropods such as Pomacea canaliculata, Achatina fulica, Meghimatium bilineatum, Limax Valentiana, Limax flavus, Acusta despecta sieboldiana and Euhadra peliomphala.

Nematodes such as Prathylenchus coffeae, Prathylenchus penetrans, Prathylenchus vulnus, Globodera rostochiensis, Heterodera glycines, Meloidogyne hapla, Meloidogyne incognita, Aphelenchoides besseyi and Bursaphelenchus xylophilus.

Adult flies such as horn fly (Haematobia irritans), horse fly (Tabanus spp.), Stomoxys calcitrans, blackfly (Simulium spp.), deer fly (Chrysops spp.), louse fly (Melophagus ovinus) and tsetse fly (Glossina spp.).

Parasitic worms such as sheep bot fly (Oestrus ovis, Cuterebra spp.), blowfly (Phaenicia spp.), screwworm (Cochliomyia hominivorax), warble fly (Hypoderma spp.), fleeceworm and Gastrophilus.

Mosquitos such as *Culex* spp., *Anopheles* spp. and *Aedes* spp.

The internal, livestock, poultry or pet parasites that the compounds of the present invention can control specifically include the following internal pests, but the present invention is not restricted thereto.

Nematodes of the genera *Haemonchus, Trichostrongylus, Ostertagia, Nematodirus, Cooperia, Ascaris, Bunostomum, Oesophagostomum, Chabertia, Trichuris, Storongylus, Trichonema, Dictyocaulus, Capillaria, Heterakis, Toxocara, Ascaridia, Oxyuris, Ancylostoma, Uncinaria, Toxascaris, Parascaris*, and the like.

Nematodes of the family Filariidae such as the genera *Wuchereria, Brugia, Onchoceca, Dirofilaria, Loa*, and the like.

Nematodes of the family Dracunculidae such as the genus *Dracunculus*.

Cestodes such as *Dipylidium caninum, Taenia taeniaeformis, Taenia solium, Taenia saginata, Hymenolepis diminuta, Moniezia benedeni, Diphyllobothrium latum, Diphyllobothrium erinacei, Echinococcus granulosus* and *Echinococcus multilocularis*.

Trematodes such as *Fasciola hepatica, F. gigantica, Paragonimus westermanii, Fasciolopsic bruski, Eurytrema pancreaticum, E. coelomaticum, Clonorchis sinensis, Schistosoma japonicum, Schistosoma haematobium* and *Schistosoma mansoni*.

*Eimeria* spp. such as *Eimeria tenella, Eimeria acervulina, Eimeria brunetti, Eimeria maxima, Eimeria necatrix, Eimeria bovis* and *Eimeria ovinoidalis*.

*Trypanosomsa cruzi, Leishmania* spp., *Plasmodium* spp., *Babesis* spp., *Trichomonadidae* spp., *Histomanas* spp., *Giardia* spp., *Toxoplasma* spp., *Entamoeba histolytica* and *Theileria* spp.

The compounds of the present invention are effective against pests that have acquired resistance to conventional insecticides such as organic phosphorus compounds, carbamate compounds or pyrethroid compounds.

That is, the compounds of the present invention can effectively control pests such as insects of the order Collembola, the order Dictyoptera, the order Orthoptera, the order Isoptera, the order Thysanoptera, the order Hemiptera, the order Lepidoptera, the order Coleoptera, the order Hymenoptera, the order Diptera, the order Aphaniptera, the order Anoplura, crustaceans of the order Arguloida, the order Shphonostomatoida, of the order Cyclopoida, Acari, gastropods and nematodes at low doses.

On the other hand, the compounds of the present invention have a quite advantageous feature that they are almost harmless to mammals, fishes, crustaceans and beneficial insects (useful insects such as honey bees and bumblebees and natural enemies such as aphelinid wasps, aphidiid wasps, tachina flies, minute pirates bug, phytoseiid mites etc.).

The compounds of the present invention may be used in any dosage form such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet or an emulsifiable gel usually after mixed with an appropriate solid carrier or liquid carrier, and if necessary, with a surfactant, a penetrant, a spreader, a thickener, an anti-freezing agent, a binder, an anti-caking agent, a disintegrant, an antifoaming agent, a preservative, a stabilizer or the like. A formulation in an arbitrary dosage form may be sealed in water-soluble packaging such as a water-soluble capsule or a water-soluble film, for labor saving or improved safety.

As solid carriers, natural minerals such as quartz, calcite, meerschaum, dolomite, chalk, kaolinite, pyrophyllite, sericite, halloysite, methahalloysite, kibushi clay, gairome clay, pottery stone, zeeklite, allophane, Shirasu, mica, talc, bentonite, activated clay, acid clay, pumice, attapulgite, zeolite and diatomaceous earth; calcined natural minerals such as calcined clay, pearlite, Shirasu-balloons, vermiculite, attapulgus clay and calcined diatomaceous earth; inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride, saccharides such as glucose, fructose, sucrose and lactose; polysaccharides such as starch, cellulose powder and dextrin; organic substances such as urea, urea derivatives, benzoic acid and benzoic acid salts; plants such as wood flour, powdered cork, corncob, walnut shell and tobacco stems, fly ash, white carbon (such as hydrated synthetic silica, anhydrous synthetic silica and hydrous synthetic silicate), fertilizers and the like may be mentioned.

As liquid carriers, aromatic hydrocarbons such as xylene, alkyl ($C_9$ or $C_{10}$ etc.) benzene, phenylxylylethane and alkyl ($C_1$ or $C_3$ etc.) naphthalene; aliphatic hydrocarbons such as machine oil, normal paraffin, isoparaffin and naphthene; mixtures of aromatic hydrocarbons and aliphatic hydrocarbons such as kerosene; alcohols such as ethanol, isopropanol, cyclohexanol, phenoxyethanol and benzyl alcohol; polyhydric alcohols such as ethylene glycol, propylene glycol, diethylene glycol, hexylene glycol, polyethylene glycol and polypropylene glycol; ethers such as propyl cellosolve, butyl cellosolve, phenyl cellosolve, propylene glycol monomethyl ether, propylene glycol monoethyl ether, propylene glycol monopropyl ether, propylene glycol monobutyl ether and propylene glycol monophenyl ether; ketones such as acetophenone, cyclohexanone and γ-butyrolactone; esters such as fatty acid methyl esters, dialkyl succinates, dialkyl glutamate, dialkyl adipates and dialkyl phthalates; acid amides such as N-alkyl ($C_1$, $C_8$ or $C_{12}$ etc.) pyrrolidone; fats and oils such as soybean oil, linseed oil, rapeseed oil, coconut oil, cottonseed oil and castor oil; dimethyl sulfoxide; water and the like may be mentioned.

These solid and liquid carriers may be used alone or in combinations of two or more.

As surfactants, nonionic surfactants such as polyoxyethylene alkyl ether, polyoxyethylene alkyl (mono or di) phenyl ether, polyoxyethylene(mono, di or tri)styrylphenyl ether, polyoxyethylenepolyoxypropylene block copolymers, polyoxyethylene fatty acid (mono or di) ester, sorbitan fatty acid ester, polyoxyethylene sorbitan fatty acid ester, ethylene oxide adducts of castor oil, acetylene glycol, acetylene alcohol, ethylene oxide adducts of acetylene glycol, ethylene oxide adducts of acetylene alcohol and alkyl glycosides; anionic surfactants such as alkyl sulfate salts, alkylbenzenesulfonic acid salts, lignin sulfonate, alkylsulfosuccinic acid salts, naphthalenesulfonic acid salts, alkylnaphthalenesulfonic acid salts, salts of naphthalenesulfonic acid-formalin condensates, salts of alkylnaphthalenesulfonic acid-formalin condensates, polyoxyethylene alkyl ether sulfate or phosphate salts, polyoxyethylene (mono or di) alkylphenyl ether sulfate or phosphate salts, polyoxyethylene (mono, di or tri) styrylphenyl ether sulfate or phosphate salts, polycarboxylic acid salts (such as polyacrylates, polymaleates and copolymers of maleic acid and an olefin) and polystyrenesulfonic acid salts; cationic surfactants such as alkylamine salts and alkyl quaternary ammonium salts; amphoteric surfactants such as amino acid types and betaine types, silicone surfactants; and fluorine surfactants may be mentioned.

The amount of these surfactants is usually preferably from 0.05 to 20 parts by weight per 100 parts by weight of the agent of the present invention, though there is no particular restrictions. These surfactants may be used alone or in combination of two or more.

The suitable application dose of the compounds of the present invention is generally about from 0.005 to 50 kg per hectare (ha) in terms of the active ingredient, though it varies depending on the application situation, the application season, the application method and the cultivated crop.

When the compounds of the present invention are used to control external or internal parasites in or on mammals and birds as farm animals/poultry and pet animals, the compounds of the present invention may be administered in an effective amount together with pharmaceutically acceptable additives orally, parenterally by injection (intramuscular, subcutaneously, intravenously or intraperitoneally); percutaneously by dipping, spraying, bathing, washing, pouring-on and spotting-on and dusting, or intranasally. The compounds of the present invention may be administered through molded articles such as chips, plates, bands, collars, ear marks, limb bands and ID tags.

The compounds of the present invention are administered in an arbitrary dosage form suitable for the administration route.

In a case where the compounds of the present invention are used to control external or internal parasites, the suitable application dose of the compound (1) of the present invention as an active ingredient is generally from 0.01 to 100 mg/kg body weight, preferably from 0.01 to 50 mg/kg body weight of a target animal, though it varies depending on e.g. the type of pests to be controlled, the type of the target animal, or the application method. Particularly with respect to application to a dog, the suitable application dose is generally from 1 to 5,000 mg/kg body weight, preferably from 1 to 100 mg/g body weight of a target dog, though it varies depending on the type or the age of the target dog, or the external parasites to be controlled.

In a case where the compounds of the present invention are used to control external or internal parasites, the application interval may be optionally set usually within a range of from daily to annually, though it varies depending on e.g. the type of pests to be controlled, the type of the target animal, or the application method. The application interval is preferably from once a week to every six months, more preferably daily (every 24 hours), monthly, once a month, every two months, every three months, or every six months.

In a case where the compounds of the present invention are used to control external paracites on a dog, with respect to the timing of application of the compound of the present invention to the dog, the compound of the present invention may be orally administered to the dog 30 minutes before start of feeding or 120 minutes after completion of feeding. "30 minutes before start of feeding or 120 minutes after completion of feeding" here is based on an action of the dog to take nutritious food. For example, in a case where the dog feeding time is 20 minutes, the time specified is 30 minutes before start of feeding to 120 minutes after completion of feeding, that is, 170 minutes in total. A case where feeding is suspended, the compound of the present invention is orally administered and feeding is restarted, is included. In this specification, feeding means an action of an animal to take food.

The number of feeding of a dug is usually three to four times a day in the case of a dog of less than six months old, twice to three times a day in the case of a dog of six months to less than one year old, twice a day in the case of an adult dog of about one to five years old, and twice to three times a day in the case of an old dog of 6 years old or older, though it varies depending on the type or the age of the dog or the habit. In the present invention, feeding means an action of an animal to take nutritious food, and does not include an action to give food and the like to a dog for training or breeding.

The dosage form may be a solid preparation such as dusts, granules, wettable powders, pellets, tablets, boluses, capsules and a molded article containing an active ingredient; a liquid preparation such as an injection fluid, an oral liquid, a liquid preparation applied to the skin or coelom; a solution preparation such as a pour-on preparation, a spot-on preparation, flowables and emulsions; and a semisolid preparation such as an ointment and gels.

In a case where the compounds of the present invention are orally administered, the dosage form may, for example, be a solid preparation such as tablets, chewables, capsules, pills, boluses, granules and powders; a semisolid preparation such as pastes and gels; and a liquid preparation such as drinks.

In the case of percutaneous administeration, the dosage form may, for example, be a solid preparation such as powders; a semisolid preparation such as a cream, a salve and ointment, pastes and gels; and a liquid preparation such as a spary, aerosols, solutions and emulsions, suspensions, and lotions.

Further, in the case of administration by injection, the dosage form may, for example, be a liquid preparation such as solutions and emulsions, and suspensions, and in the case of intranasal administration, the dosage form may, for example, be a liquid preparation such as aerosols. In the case of spraying over an environment where animals are bred, such as a stable, the dosage form may, for example, be a solid preparation such as wettable powders, dusts or granules; and a liquid preparation such as emulsions and suspension concentrates.

The formulation to be used for parasiticides of the present invention is not limited to such dosage forms.

The solid preparation may be orally administered as it is, or may be percutaneously administered or sprayed over an environment where animals are bred, such as a stable, after dilution with water.

The solid preparation to be orally administered, may be prepared by mixing the compound represented by the formula (1) or its salt and one or more vehicles or binders suitable for oral administration, and as the case requires, physiologically acceptable additives such as a lubricant, a disintegrant, a dye and a pigment, and forming the mixture into a desired shape.

The vehicle and the binder may, for example, be a saccharide or saccharide derivative such as lactose, sucrose, mannitol or sorbitol; a starch such as corn starch, wheat starch, rice starch or potato starch; a cellulose or cellulose derivative such as methyl cellulose, carboxymethyl cellulose, hydroxyethyl cellulose, hydroxypropyl cellulose or hydroxypropylmethyl cellulose; a protein or protein derivative such as zein or gelatin; honey, gum arabic glue, or a synthetic polymer compound such as polyvinyl alcohol or polyvinyl pyrrolidone.

The lubricant may, for example, be magnesium stearate, and the disintegrant may, for example, be cellulose, agar, alginic acid, crosslinked polyvinyl pyrrolidone or a carbonate.

Among solid preparations to be orally administered, in the case of a solid formulation such as chewables, additives which impart a taste, texture or flavor desired by animals to which the preparation is to be administered, may be used. The carriers and additives to be used for the solid preparation of the parasiticidal composition of the present invention are not limited thereto.

The liquid preparation may be administered percutaneously or by injection as it is, or may be administered orally by being mixed with food, orally or percutaneously administered after being diluted with water, or sprayed to an environment where animals are bred, such as a stable.

An injection fluid may be administered intravenously, intramuscularly or subcutaneously. An injection fluid can be prepared by dissolving an active ingredient in an appropriate solvent and, if necessary, adding additives such as a solubilizer, an acid, a base, a buffering salt, an antioxidant and a protectant.

As appropriate solvents, water, ethanol, butanol, benzyl alcohol, glycerin, propylene glycol, polyethylene glycol, N-methylpyrrolidone and mixtures thereof, physiologically acceptable vegetable oils, and synthetic oils suitable for injection may be mentioned.

As solubilizers, polyvinylpyrrolidone, polyoxyethylated castor oil, polyoxyethylated sorbitan ester and the like may be mentioned.

As protectants, benzyl alcohol, trichlorobutanol, p-hydroxybenzoic acid esters, n-butanol and the like may be mentioned.

An oral liquid may be administered directly or after dilution and can be prepared in the same manner as an injection fluid.

A flowable, an emulsion or the like may be administered directly or after dilution percutaneously or by environmental application.

A liquid preparation applied to the skin is administered by dripping, spreading, rubbing, spraying, sprinkling or dipping (soaking, bathing or washing) and can be prepared in the same manner as an injection fluid.

A pour-on preparation and a spot-on preparation are dripped or sprayed to a limited area of the skin so that they permeate through the skin and act systemically. A pour-on preparation and a spot-on preparation can be prepared by dissolving, suspending or emulsifying an active ingredient in an appropriate skin-friendly solvent or solvent mixture. If necessary, additives such as a surfactant, a colorant, an absorbefacient, an antioxidant, a light stabilizer and an adhesive may be added.

As appropriate solvents, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF (N,N-dimethylformamide), liquid paraffin, light liquid paraffin, silicone, dimethylacetamide, N-methylpyrrolidone or 2,2-dimethyl-4-oxy-methylene-1,3-dioxolane may be mentioned.

As absorbefacients, DMSO (dimethyl sulfoxide), isopropyl myristate, pelargonic acid dipropylene glycol, silicone oil, fatty acid esters, triglycerides and aliphatic alcohols may be mentioned.

As antioxidants, sulfites, metabisulfites, ascorbic acid, butylhydroxytoluene, butylhydroxyanisole and tocopherol may be mentioned.

An emulsion may be administered orally, percutaneously or by injection. An emulsion can be prepared by dissolving an active ingredient in a hydrophobic phase or a hydrophilic phase and homogenizing the resulting solution with another liquid phase together with an appropriate emulsifier, and further if necessary with additives such as a colorant, an absorbefacient, a protectant, an antioxidant, a light screen and a thickener.

As hydrophobic phases (oils), paraffin oil, silicone oil, sesame oil, almond oil, castor oil, synthetic triglycerides, ethyl stearate, di-n-butyryl adipate, hexyl laurate, pelargonic acid dipropylene glycol, esters of branched short-chain fatty acids with $C_{16}$-$C_{18}$ saturated fatty acids, isopropyl myristate, isopropyl palmitate, esters of $C_{12}$-$C_{18}$ saturated alcohols with caprylic/capric acid, isopropyl stearate, oleyl oleate, decyl oleate, ethyl oleate, ethyl lactate, fatty acid ester waxes, dibutyl phthalate, diisopropyl adipate, isotridecyl alcohol, 2-octyldodecanol, cetylstearyl alcohol and oleyl alcohol may be mentioned.

As hydrophilic phases, water, propylene glycol, glycerin and sorbitol may be mentioned.

As emulsifiers, nonionic surfactants such as polyoxyethylated castor oil, polyoxyethylated sorbitan monoolefinic acid, sorbitan monostearate, glycerin monostearate, polyoxyethyl stearate and alkyl phenol polyglycol ether; amphoteric surfactants such as disodium N-lauryl-β-iminodipropionate and lecithin; anionic surfactants such as sodium lauryl sulfate, aliphatic alcohol sulfate ether and mono/dialkylpolyglycol orthophosphate monoethanolamine salt; and cationic surfactants such as cetyltrimethylammonium chloride may, for example, be mentioned.

As other additives, carboxymethylcellulose, methylcellulose, polyacrylate, alginate, gelatin, gum arabic, polyvinylpyrrolidone, polyvinyl alcohol, methyl vinyl ether, maleic anhydride copolymers, polyethylene glycol, waxes and colloidal silica may be mentioned.

A semisolid preparation is administered by applying or spreading onto the skin or introducing into the coelom. A gel can be prepared by adding a thickener to a solution prepared in the same manner as an injection fluid sufficiently to give a transparent viscous substance like an ointment.

Next, Formulation Examples of preparations using the compounds of the present invention are given below. However, formulations of the present invention are by no means restricted thereto. In the following Formulation Examples, "parts" means parts by weight.

[Wettable Powder]

| | |
|---|---|
| Compound of the present invention | 0.1 to 80 parts |
| Solid carrier | 5 to 98.9 parts |
| Surfactant | 1 to 10 parts |
| Others | 0 to 5 parts |

As the others, an anti-caking agent, a stabilizer and the like may be mentioned.

[Emulsifiable Concentrate]

| | |
|---|---|
| Compound of the present invention | 0.1 to 30 parts |
| Liquid carrier | 45 to 95 parts |
| Surfactant | 4.9 to 15 parts |
| Others | 0 to 10 parts |

As the others, a spreader, a stabilizer and the like may be mentioned.

[Suspension Concentrate]

| | |
|---|---|
| Compound of the present invention | 0.1 to 70 parts |
| Liquid carrier | 15 to 98.89 parts |
| Surfactant | 1 to 12 parts |
| Others | 0.01 to 30 parts |

As the others, an anti-freezing agent, a thickener and the like may be mentioned.

[Water Dispersible Granule]

| | |
|---|---|
| Compound of the present invention | 0.1 to 90 parts |
| Solid carrier | 0 to 98.9 parts |
| Surfactant | 1 to 20 parts |
| Others | 0 to 10 parts |

As the others, a binder, a stabilizer and the like may be mentioned.

[Soluble Concentrate]

| | |
|---|---|
| Compound of the present invention | 0.01 to 70 parts |
| Liquid carrier | 20 to 99.99 parts |
| Others | 0 to 10 parts |

As the others, an anti-freezing agent, a spreader and the like may be mentioned.

[Granule]

| | |
|---|---|
| Compound of the present invention | 0.01 to 80 parts |
| Solid carrier | 10 to 99.99 parts |
| Others | 0 to 10 parts |

As the others, a binder, a stabilizer and the like may be mentioned.

[Dustable Powder]

| | |
|---|---|
| Compound of the present invention | 0.01 to 30 parts |
| Solid carrier | 65 to 99.99 parts |
| Others | 0 to 5 parts |

As the others, an anti-drift agent, a stabilizer and the like may be mentioned.

Next, more specific Formulation Examples of preparations containing the compounds of the present invention as an active ingredient are given below. However, the present invention is by no means restricted thereto.

[Formulation Example 1] Wettable Powder

| | |
|---|---|
| Compound No. 1-1-001a of the present invention | 20 parts |
| Pyrophyllite | 74 parts |
| Sorpol 5039 | 4 parts |
| (tradename for a mixture of a nonionic surfactant and an anionic surfactant: manufactured by TOHO Chemical Industry Co.; Ltd.) | |
| CARPLEX #80D | 2 parts |
| (tradename for hydrous synthetic silicic acid: manufactured by Shionogi & Co., Ltd.) | |

The above ingredients are mixed and pulverized homogenously to obtain a wettable powder.

[Formulation Example 2] Emulsifiable Concentrate

| | |
|---|---|
| Compound No. 1-1-001a of the present invention | 5 parts |
| Xylene | 75 parts |
| N-methylpyrrolidone | 15 parts |
| Sorpol 2680 | 5 parts |
| (tradename for a mixture of a nonionic surfactant and an anionic surfactant: manufactured by TOHO Chemical Industry Co., Ltd.) | |

The above ingredients are mixed homogenously to obtain an emulsifiable concentrate.

[Formulation Example 3] Suspension Concentrate

| | |
|---|---|
| Compound No. 1-1-001a | 25 parts |
| AGRISOL S-710 | 10 parts |
| (tradename for a nonionic surfactant: manufactured by Kao Corporation) | |
| Runox 1000C | 0.5 part |
| (tradename for an anionic surfactant: manufactured by TOHO Chemical Industry Co., Ltd.) | |
| Xanthan gum | 0.2 part |
| Water | 64.3 parts |

The above ingredients are mixed homogenously and wet-pulverized to obtain a suspension concentration.

[Formulation Example 4] Water Dispersible Granule

| | |
|---|---|
| Compound No. 1-1-001a of the present invention | 75 parts |
| HITENOL NE-15 | 5 parts |
| (tradename for an anionic surfactant: manufactured by DKS Co., Ltd.) | |
| VANILLEX N | 10 parts |
| (tradename for an anionic surfactant: manufactured by Nippon Paper Industries Co., Ltd.) | |
| CARPLEX #80D | 10 parts |
| (tradename for hydrous synthetic silicic acid: manufactured by Shionogi & Co., Ltd.) | |

The above ingredients are mixed and pulverized homogenously, then kneaded with a small amount of water, granulated through an extrusion granulator and dried to obtain a water dispersible granule.

[Formulation Example 5] Granule

| | |
|---|---|
| Compound No. 1-1-001a of the present invention | 5 parts |
| Bentonite | 50 parts |
| Talc | 45 parts |

The above ingredients are mixed and pulverized homogenously, then kneaded with a small amount of water, granulated through an extrusion granulator and dried to obtain a granule.

[Formulation Example 6] Dustable Powder

| | |
|---|---|
| Compound No. 1-1-001a of the present invention | 3 parts |
| CARPLEX #80D | 0.5 part |
| (tradename for a hydrous synthetic silicic acid: manufactured by Shionogi & Co., Ltd.) | |
| Kaolinite | 95 parts |
| Diisopropyl phosphate | 1.5 parts |

The above ingredients are mixed and pulverized homogeneously to obtain a dustable powder.

It is applied after diluted with water by a factor of from 1 to 10000 or directly without dilution.

[Formulation Example 7] Wettable Powder Preparation

| | |
|---|---|
| Compound No. 1-1-001a of the present invention | 25 parts |
| Sodium diisobutylnaphthalenesulfonate | 1 part |
| Calcium n-dodecylbenzenesulfonate | 10 parts |
| Alkyl aryl polyglycol ether | 12 parts |
| Naphthalenesulfonic acid-formalin condensate sodium salt | 3 parts |
| Silicone emulsion | 1 part |
| Silicon dioxide | 3 parts |
| Kaolin | 45 parts |

[Formulation Example 8] Water-Soluble Concentrate Preparation

| | |
|---|---|
| Compound No. 1-1-001a of the present invention | 20 parts |
| Polyoxyethylenelauryl ether | 3 parts |
| Sodium dioctylsulfosuccinate | 3.5 parts |
| Dimethyl sulfoxide | 37 parts |
| 2-Propanol | 36.5 parts |

[Formulation Example 9] Liquid Preparation for Spraying

| | |
|---|---|
| Compound No. 1-1-001a of the present invention | 2 parts |
| Dimethyl sulfoxide | 10 parts |
| 2-Propanol | 35 parts |
| Acetone | 53 parts |

[Formulation Example 10] Liquid Preparation for Percutaneous Administration

| | |
|---|---|
| Compound No. 1-1-001a of the present invention | 5 parts |
| Hexylene glycol | 50 parts |
| Isopropanol | 45 parts |

[Formulation Example 11] Liquid Preparation for Percutaneous Administration

| | |
|---|---|
| Compound No. 1-1-001a of the present invention | 5 parts |
| Propylene glycol monomethyl ether | 50 parts |
| Dipropylene glycol | 45 parts |

[Formulation Example 12] Liquid Preparation for Percutaneous Administration (by Dripping)

| | |
|---|---|
| Compound No. 1-1-001a of the present invention | 2 parts |
| Light liquid paraffin | 98 parts |

[Formulation Example 13] Liquid Preparation for Percutaneous Administration (by Dripping)

| | |
|---|---|
| Compound No. 1-1-001a of the present invention | 2 parts |
| Light liquid paraffin | 58 parts |
| Olive oil | 30 parts |
| ODO-H | 9 parts |
| Shin-etsu silicone | 1 part |

For use as agricultural chemicals, the compounds of the present invention may be mixed with other herbicides, insecticides, acaricides, nematicides, fungicides, plant growth regulators, synergists, fertilizers, soil conditioners and the like at the time of formulation or application.

Particularly, the combined use with other agricultural chemicals or plant hormone is expected to reduce the cost by enabling control at lower doses, to broaden the insecticidal spectrum by the synergistic effect of the other agrochemicals, and to achieve a higher pesticidal effect. In such cases, they may be combined with a plurality of known agricultural chemicals.

The agricultural chemicals to be used in combination with the compounds of the present invention include, for example, the compounds disclosed in e.g. The Pesticide Manual, 15th edition, 2009, having the generic names listed below, but are not necessarily restricted thereto.

Fungicides: acibenzolar-S-methyl, acylaminobenzamide, acypetacs, aldimorph, ametoctradin, amisulbrom, amobam, ampropyfos, anilazine, azaconazole, azithiram, azoxystrobin, barium polysulfide, benalaxyl, benalaxyl-M, benodanil, benomyl, benquinox, bentaluron, benthiavalicarb-isopropyl, benthiazole, benzamacril, benzamorf, benzovindiflupyr, bethoxazine, binapacryl, biphenyl, bitertanol, blasticidin-S, bixafen, bordeaux mixture, boscalid, bromuconazole, bupirimate, buthiobate, calcium polysulfide, calcium polysulfide, captafol, captan, carpropamid, carbamorph, carbendazim, carboxin, carvone, cheshunt mixture, chinomethionat, chlobenthiazone, chloraniformethane, chloranil, chlorfenazol, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper sulfate, copper sulfate, basic, copper zinc chromate, cufraneb, coumoxystrobin, cuprobam, cyazofamid, cyclafuramid, cycloheximide, cyflufenamid, cymoxanil, cypendazole, cyproconazol, cyprodinil, cyprofuram, dazomet, debacarb, decafentin, dehydroacetic acid, dichlofluanid, dichlone, dichlorophen, dichlozoline, diclobutrazol, diclocymet, diclomedine, dicloran, etc.

Fungicides (continued): diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipymetitrone, dipyrithione, ditalimfos, dithianon, dodemorph-acetate, dodine, drazoxolon, edifenphos, enestrobin, enoxastrobin, epoxiconazole, etaconazole, ethaboxam, etem, ethirimol, ethoxyquin, etridiazole, famoxadone, fenarimol, fenbuconazole, fenamidone, fenaminosulf, fenaminstrobin, fenapanil, fendazosulam, fenfuram, fenhexamid, fenitropan, fenoxanil, fenpiclonil, fenpropidin, fenpyrazamine, fenpropimorph, fentin, ferbam, ferimzone, fluazinam, fludioxonil, flufenoxystrobin, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, fosetyl-aluminium, fthalide, fuberidazole, furalaxyl, furametpyr, furcarbanil, furconazole, furconazole-cis, furmecyclox, furphanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine-albesilate, iminoctadine-triacetate, ipconazole, iprobenfos, iprodione, iprovalicarb, isofetamid, isoprothiolane, isopyrazam, isotianil, isovaledione, etc.

Fungicides (continued): kasugamycin, kresoxim-methyl, laminarin, mancopper, mancozeb, mandestrobin, mandipropamid, maneb, mebenil, mecarbinzid, mepanipyrim, meptyldinocap, mepronil, metalaxyl, metalaxyl-M, metam, metazoxolon, metconazole, methasulfocarb, methfuroxam, methyl isothiocyanate, metiram, metominostrobin, metrafenone, metsulfovax, milneb, myclobutanil, myclozolin, nabam, natamycin, nickel bis(dimethyldithiocarbamate), nitrostyrene, nitrothal-isopropyl, nuarimol, OCH, octhilinone, ofurace, orysastrobin, oxathiapiprolin, oxadixyl, oxine copper, oxycarboxin, oxpoconazole fumarate, pefurzoate, penconazole, penflufen, pencycuron, penthiopyrad, o-phenylphenol, phosdiphen, picarbutrazox, picoxystrobin, piperalin, polycarbamate, polyoxins, polyoxorim, potassium azide, potassium hydrogen carbonate, proquinazid, probenazole, prochloraz, procymidone, propamocarb hydrochloride, propiconazole, propineb, prothiocarb, prothioconazole, pydiflumetofen, pyracarbolid, pyraclostrobin, pyrametostrobin, pyraoxystrobin, pyraziflumid, pyrazophos, pyribencarb-methyl, pyridinitril, pyrifenox, pyrimethanil, pyriminostrobin, pyrimorph, pyriofenone, pyrisoxazole, pyroquilon, pyroxychlor, pyroxyfur, quinomethionate, quinoxyfen, quintozene, quinacetol-sulfate, quinazamid, quinconazole, rabenzazole, Bacillus subtilis (Strain: D747, FZB24, GBO3, HA10404, MBI600, QST713, Y1336, etc.), etc.

Fungicides (continued): sedaxane, sodium azide, sodium hydrogen carbonate, sodium hypochlorite, sulfur, spiroxamine, salycylanilide, silthiofam, simeconazole, tebuconazole, tebufloquin, tecnazene, tecoram, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolprocarb, tolylfluanid, triadimefon, toriadimenol, triamiphos, triarimol, triazoxide, triazbutil, tributyltin oxide, trichlamide, tricyclazole, tridemorph, trifloxystrobin, triflumizole, triforine, triclopyricarb, triticonazole, validamycin, valifenalate, vinclozolin, zarilamide, zinc sulfate, zineb, ziram, zoxamide, shiitake mushroom mycelium extracts, shiitake mushroom fruiting body extracts, NF-180 (test name), MIF-1002 (test name), S-2399 (test name), AKD-5195 (test name), etc.

Bactericides: benzalkonium chloride, bithionol, bronopol, cresol, formaldehyde, nitrapyrin, oxolinic acid, oxyterracycline, streptomycin, tecloftalam, etc.

Nematicides: aldoxycarb, benclothiaz, cadusafos, DBCP, dichlofenthion, DSP, ethoprophos, fenamiphos, fensulfothion, fluazaindolizine, fluensulfone, fosthiazate, fosthietan, imicyafos, isamidofos, isazofos, oxamyl, thiaxazafen, thionazin, tioxazafen, BYI-1921 (test name), MAI-08015 (test name), etc.

Acaricides: acequinocyl, acrinathrin, amidoflumet, amitraz, azocyclotin, BCI-033 (test name), benzoximate, bifenazate, bromopropylate, chinomethionat, chlorobezilate, clofentezine, cyenopyrafen, cyflumetofen, cyhexatine, dicofol, dienochlor, diflovidazin, DNOC, etoxazole, fenazaquin, fenbutatin oxide, fenothiocarb, fenpropathrin, fenpyroximate, fluacrypyrim, halfenprox, hexythiazox, milbemectin, propargite, pyflubumide, pyridaben, pyrimidifen, S-1870 (test name), spirodiclofen, spyromesifen, CL900167 (test name), tebufenpyrad, NA-89 (test name), etc.

Insecticides: abamectin, acephate, acetamipirid, afidopyropen, afoxolaner, alanycarb, aldicarb, allethrin, azamethiphos, azinphos-ethyl, azinphos-methyl, Bacillus thuringiensis, bendiocarb, benfluthrin, benfuracarb, bensultap, bifenthrin, bioallethrin, bioresmethrin, bistrifluron, broflanilide, buprofezin, butocarboxim, carbaryl, carbofuran, carbosulfan, cartap, chlorantraniliprole, chlorethxyfos, chlorfenapyr, chlorfenvinphos, chlorfluazuron, chlormephos, chloroprallethrin, chlorpyrifos, chlorpyrifos-methyl, chromafenozide, clothianidin, cyanophos, cyantraniliprole, cyclaniliprole, cycloprothrin, cyflumetofen, cyfluthrin, beta-cyfluthrin, cyhalodiamide, cyhalothrin, gamma-cyhalothrin, lambda-cyhalothrin, cypermethrin, alpha-cypermethrin, beta-cypermethrin, zeta-cypermethrin, cyphenothrin, cyromazine, deltamethrin, diacloden, diafenthiuron, diazinon, dicloromezotiaz, dichlorvos, diflubenzuron, dimefluthrin, dimethylvinphos, dinotefuran, diofenolan, disulfoton, dimethoate, emamectin-benzoate, empenthrin, endosulfan, alpha-endosulfan, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, fluazuron, flubendiamide, flucycloxuron, flucythrinate, flufenerim, flufenoxuron, flufenprox, flumethrin, fluralaner, fluvalinate, tau-fluvalinate, fonophos, formetanate, formothion, furathiocarb, flufiprole, fluhexafon, flupyradifurone, flometoquin, etc.

Insecticides (continued): halofenozide, heptafluthrin, hexaflumuron, hydramethylnon, imidacloprid, imiprothrin, isofenphos, indoxacarb, indoxacarb-MP, isoprocarb, isoxathion, kappa-bifenthrin, kappa-tefluthrin, lepimectin, lufenuron, malathion, meperfluthrin, metaflumizone, metaldehyde, methamidophos, methidathion, methacrifos, metalcarb, methomyl, methoprene, methoxychlor, methoxyfenozide, methyl bromide, metofluthrin, epsilon-metofluthrin, momfluorothrin, epsilon-momfluorothrin, monocrotophos, muscalure, nitenpyram, novaluron, noviflumuron, omethoate, oxydemeton-methyl, oxydeprofos, parathion, parathion-methyl, pentachlorophenol, permethrin, phenothrin, phenthoate, phoxim, phorate, phosalone, phosmet, phosphamidon, pirimicarb, pirimiphos-methyl, profenofos, profluthrin, prothiofos, propaphos, protrifenbute, pymetrozine, pyraclofos, pyrethrins, pyridalyl, pyrifluquinazon, pyriprole, pyrafluprole, pyriproxyfen, resmethrin, rotenone, SI-0405 (test name), sulprofos, silafluofen, spinetoram, spinosad, spiromesifen, spirotetramat, sulfoxaflor, sulfotep, SYJ-159 (test name), tebfenozide, teflubenzuron, tefluthorin, terbufos, tetrachlorvinphos, tetramethrin, d-tetramethrin, tetramethylfluthrin, tetraniliprole, thiacloprid, thiocyclam, thiodicarb, thiamethoxam, thiofanox, thiometon, tolfenpyrad, tralomethrin, transfluthrin, triazamate, trichlorfon, triazuron, triflumezopyrim, triflumuron, vamidothion, fluxametamide, MIE-1209 (test name), ME5382 (test name), Praziquantel, Febantel, etc.

EXAMPLES

Now, the present invention will be described in further detail with reference to Synthetic Examples and Test Examples of the compounds of the present invention. However, the present invention is by no means restricted thereto.

The preparative medium pressure liquid chromatography used was a preparative medium pressure chromatograph (YFLC-Wprep manufactured by Yamazen Science, Inc. flow rate: 18 ml/min, 40-μm silica gel column).

Chemical shift values of proton nuclear magnetic resonance (hereinafter referred to as $^1$H-NMR) in Synthetic Examples and Reference Examples were measured by using Me$_4$Si (tetramethylsilane) as a standard substance in deuterated chloroform solvent at 300 MHz (JNM-ECX300 or JNM-ECP300 manufactured by JEOL Ltd.).

Reference symbols in $^1$H-NMR chemical shift values have the following meanings.

s: singlet, d: doublet, dd: double doublet, t: triplet, q: quartet, and m: multiplet.

Synthetic Example 1: Synthesis of 2-[6-chloro-3-(ethylthio)pyrazolo[1,5-a]pyridin-2-yl]-3-methyl-6-(trifluoromethyl)-3H-imidazo[4,5-b]pyridine (Compound No. 1-1-001 b of the Present Invention)

Step 1: Synthesis of 6-chloro-N-[2-(methylamino)-5-(trifluoromethyl)pyridin-3-yl]pyrazolo[1,5-a]pyridine-2-carboxamide To a mixed solution of 584 mg of N$^2$-methyl-5-(trifluoromethyl)pyridine-2,3-diamine and 5 ml of pyridine, at room temperature, 500 mg of 6-chloropyrazolo[1,5-a]pyridine-2-carboxylic acid, 975 mg of 1-ethyl-3-(3-dimethylaminopropyl)carbodiimide hydrochloride and 31 mg of 4-dimethylaminopyridine were successively added. After the addition, the mixture was stirred at room temperature for 18 hours. After the completion of the reaction, 10 ml of water was added to the reaction mixture, and the precipitated solid was collected by filtration to obtain 500 mg of the desired product. The product was used in the next step 2 without further purification.

Step 2: Synthesis of 2-(6-chloropyrazolo[1,5-a]pyridin-2-yl)-3-methyl-6-(trifluoromethyl)-3H-imidazo[4,5-b]pyridine A mixed solution of 500 mg of the desired product obtained in step 1 and 5 ml of acetic acid was stirred under reflux with heating for 3 hours. After the completion of the reaction, 10 ml of water was added to the reaction mixture at room temperature. The precipitated solid was collected by filtration to obtain 306 mg of the desired product as a brown solid.

Melting point: 238 to 240° C.

1H-NMR (CDCl$_3$): δ8.75-8.65 (m, 1H), 8.65-8.55 (m, 1H), 8.35-8.25 (m, 1H), 7.65-7.55 (m, 1H), 7.40-7.35 (m, 1H), 7.20 (dd, J=9.6, 1.8 Hz, 1H), 4.38 (s, 3H).

Step 3: Synthesis of 2-[6-chloro-3-(ethylthio)pyrazolo[1,5-a]pyridin-2-yl]-3-methyl-6-(trifluoromethyl)-3H-imidazo[4,5-b]pyridine (Compound No. 1-1-001 b of the Present Invention)

To a mixed solution of 929 mg of N-chlorosuccinimide and 6 ml of 1,2-dichloroethane, at −30° C., 540 mg of ethanethiol was added. After the addition, the mixture was stirred at room temperature for one hour. After the stirring, the reaction mixture was subjected to filtration through Celite, and the Celite was washed with 2 ml of 1,2-dichloroethane. To the resulting filtrate and washing liquid, 306 mg of the product obtained in Step 2 was added at room temperature. After the addition, the mixture was stirred under reflux with heating for 6 hours. After the completion of the reaction, the reaction mixture was mixed with 10 ml of water and extracted with chloroform (10 ml×2). The resulting organic layer was washed with 10 ml of a saturated sodium hydrogen carbonate aqueous solution, dehydrated with saturated aqueous sodium chloride and dried over anhydrous sodium sulfate, and the solvent was evaporated under reduced pressure to obtain 200 mg of the desired product as a brown solid.

Synthetic Example 2: Synthesis of 2-[6-chloro-3-(ethylsulfonyl)pyrazolo[1,5-a]pyridin-2-yl]-3-methyl-6-(trifluoromethyl)-3H-imidazo[4,5-b]pyridine (Compound No. 1-1-001a of the Present Invention)

To a mixed solution of 200 mg of the compound No. 1-1-001b of the present invention obtained in Synthetic Example 1 and 5 ml of chloroform, 184 mg of 65 mass % m-chloroperbenzoic acid (containing about 30 mass % of water) was added under cooling with ice. After the addition, the mixture was stirred at room temperature for 18 hours. After the completion of the reaction, the reaction mixture was mixed with a saturated sodium thiosulfate aqueous solution and extracted with 10 ml of chloroform. The resulting organic layer was washed with 10 ml of a 1 mol/L (liter) sodium hydroxide aqueous solution and dried over anhydrous sodium sulfate, and the solvent was evaporated under reduced pressure. The resulting residue was purified by preparative medium pressure liquid chromatography [n-hexane:ethyl acetate with a gradient of from 100:0 to 0:100 (volume ratio, the same applies hereinafter)] to obtain 163 mg of the desired product as a white solid.

Melting point: 132 to 136° C.

1H-NMR (CDCl$_3$): δ8.76 (d, J=1.8 Hz, 1H), 8.70-8.65 (m, 1H), 8.40-8.30 (m, 2H), 7.60-7.50 (m, 1H), 4.12 (s, 3H), 3.93 (q, J=7.5 Hz, 2H), 1.39 (t, J=7.5 Hz, 3H).

Synthetic Example 3: Synthesis of 2-[3-(ethylsulfonyl)-6-(3-(trifluoromethyl)-1H-pyrazol-1-yl)pyrazolo[1,5-a]pyridin-2-yl]-3-methyl-6-(trifluoromethyl)-3H-imidazo[4,5-b]pyridine (Compound No. 1-1-003a of the Present Invention)

To a mixed solution of 70 mg of 2-[3-(ethylsulfonyl)-6-iodopyrazolo[1,5-a]pyridin-2-yl]-3-methyl-6-(trifluoromethyl)-3H-imidazo[4,5-b]pyridine and 3 ml of N,N-dimethylformamide, at room temperature, 213 mg of cesium carbonate, 17 mg of N,N'-dimethylcyclohexane-1,2-diamine, 89 mg of 3-(trifluoromethyl)-1H-pyrazole and 25 mg of copper(I) iodide were successively added. After the addition, the atmosphere in the reaction vessel was replaced with nitrogen gas, and the mixture was stirred at 90° C. for 4 hours.

After the completion of the reaction, the reaction mixture was mixed with 10 ml of water and extracted with chloroform (10 ml×2). The resulting organic layer was washed with 10 ml of a 1 mol/L sodium hydroxide aqueous solution and dried over anhydrous sodium sulfate, and the solvent was evaporated under reduced pressure. The resulting residue was purified by preparative medium pressure liquid chromatography (n-hexane:ethyl acetate with a gradient of from 100:0 to 80:20) to obtain 32 mg of the desired product as a yellow solid.

Melting point: 226 to 229° C.

1H-NMR (CDCl$_3$): δ9.17 (dd, J=2.0, 0.8 Hz, 1H), 8.80-8.76 (m, 1H), 8.52 (dd, J=9.8, 0.8 Hz, 1H), 8.41-8.36 (m, 1H), 8.09-8.04 (m, 1H), 7.93 (dd, J=9.8, 2.0 Hz, 1H), 6.86 (d, J=2.7 Hz, 1H), 4.17 (s, 3H), 4.01 (q, J=7.5 Hz, 2H), 1.42 (t, J=7.5 Hz, 3H).

Synthetic Example 4: Synthesis of 2-[3-(ethylthio)-6-(trifluoromethyl)pyrazolo[1,5-a]pyridin-2-yl]-3-methyl-6-(trifluoromethyl)-3H-imidazo[4,5-b]pyridine (Compound No. 1-1-004b of the Present Invention)

Step 1: Synthesis of 2-[3-iodo-6-(trifluoromethyl)pyrazolo[1,5-a]pyridin-2-yl]-3-methyl-6-(trifluoromethyl)-3H-imidazo[4,5-b]pyridine To a mixed solution of 210 mg of 3-methyl-6-(trifluoromethyl)-2-[6-(trifluoromethyl)pyrazolo[1,5-a]pyridin-2-yl]-3H-imidazo[4,5-b]pyridine and 5 ml of N,N-dimethylformamide, at room temperature, 209 mg of 1,3-diiodo-5,5-dimethylhydantoin was added. After the addition, the mixture was stirred at 80° C. for 3 hours. After the completion of the reaction, 10 ml of a saturated sodium thiosulfate aqueous solution was added to the reaction mixture. The precipitated solid was collected by filtration to obtain 205 mg of the desired product as a white solid.

$^1$H-NMR (CDCl$_3$): δ8.79-8.75 (m, 1H), 8.75-8.70 (m, 1H), 8.37-8.34 (m, 1H), 7.90 (d, J=9.6 Hz, 1H), 7.53 (dd, J=9.6, 1.5 Hz, 1H), 4.43 (s, 3H).

Step 2: Synthesis of 2-[3-(ethylthio)-6-(trifluoromethyl)pyrazolo[1,5-a]pyridin-2-yl]-3-methyl-6-(trifluoromethyl)-3H-imidazo[4,5-b]pyridine (Compound No. 1-1-004b of the Present Invention)

To a mixed solution of 210 mg of the white solid obtained in Step 1 and 5 ml of 1,4-dioxane, at room temperature, 158 mg of diisopropylethylamine, 14 mg of 4,5-bis(diphenylphosphino)-9,9-dimethylxanthene, 11 mg of tris(dibenzilideneacetone)dipalladium(0) and 30 mg of ethanethiol were successively added. After the addition, the mixture was stirred under reflux with heating in a nitrogen atmosphere for 2 hours. After the completion of the reaction, the reaction mixture was mixed with 10 ml of water and extracted with chloroform (10 ml×2). The resulting organic layer was dried over anhydrous sodium sulfate, and the solvent was evaporated under reduced pressure. The resulting residue was purified by preparative medium pressure liquid chromatography (n-hexane:ethyl acetate with a gradient of from 100:0 to 50:50) to obtain 120 mg of the desired product as a pale yellow solid.

$^1$H-NMR (CDCl$_3$) δ: 8.88 (d, J=1.5 Hz, 1H), 8.75 (d, J=1.2 Hz, 1H), 8.43 (d, J=1.8 Hz, 1H), 7.99 (d, J=9.0 Hz, 1H), 7.46 (d, J=9.0 Hz, 1H), 4.22 (s, 3H), 2.97 (q, J=7.5 Hz, 2H), 1.16 (t, J=7.5 Hz, 3H).

Synthetic Example 5: Synthesis of 2-[3-(ethylthio)-6-(trifluoromethyl)-2H-indazol-2-yl]-3-methyl-6-(trifluoromethyl)-3H-imidazo[4,5-b]pyridine (Compound No. 1-10-001 b of the Present Invention)

Step 1: Synthesis of 3-methyl-6-(trifluoromethyl)-3H-imidazo[4,5-b]pyridin-2-amine To a mixed solution of 8.31 g of cyanogen bromide, 174 ml of water and 174 ml of methanol, at room temperature, 5.0 g of N$^2$-methyl-5-(trifluoromethyl)pyridine-2,3-diamine was added. After the addition, the mixture was stirred at 50° C. for 1 hour. After the completion of the reaction, the reaction mixture was adjusted to have a pH of 8 with a 1 mol/L sodium hydroxide aqueous solution at room temperature, and the solvent was evaporated under reduced pressure. The resulting residue was mixed with 100 ml of water and extracted with 100 ml of ethyl acetate. The resulting organic layer was dehydrated with saturated aqueous sodium chloride and dried over anhydrous sodium sulfate, and the solvent was evaporated under reduced pressure to obtain 3.48 g of the desired product as a purple solid.

$^1$H-NMR (CDCl$_3$): δ8.40-8.30 (m, 1H), 7.85-7.75 (m, 1H), 5.20-4.90 (brs, 2H), 3.69 (s, 3H).

Step 2: Synthesis of 3-methyl-6-(trifluoromethyl)-2-[6-(trifluoromethyl)-2H-indazol-2-yl]-3H-imidazo[4,5-b]pyridine A mixed solution of 900 mg of the purple solid obtained in step 1, 829 mg of 2-nitro-4-(trifluoromethyl)benzaldehyde and 10 ml of 2-propanol was stirred under reflux with heating for 4 hours. After the stirring, to the mixture, 2.30 g of tributylphosphine was added at room temperature. After the addition, the reaction mixture was stirred under reflux with heating for 18 hours. After the completion of the reaction, the solvent was evaporated under reduced pressure. The resulting residue was mixed with 10 ml of water and extracted with 10 ml of chloroform. The resulting organic layer was dried over anhydrous sodium sulfate, and the solvent was evaporated under reduced pressure. The resulting residue was purified by preparative medium pressure liquid chromatography (chloroform:methanol with a gradient of from 100:0 to 85:15) to obtain 447 mg of the desired product as a pale yellow solid.

Melting point: 168 to 175° C.

$^1$H-NMR (CDCl$_3$): δ9.10 (s, 1H), 8.74 (s, 1H), 8.29 (s, 1H), 8.15 (s, 1H), 7.90 (d, J=9.0 Hz, 1H), 7.35 (d, J=9.0 Hz, 1H), 4.42 (s, 3H).

Step 3: Synthesis of 2-[3-chloro-6-(trifluoromethyl)-2H-indazol-2-yl]-3-methyl-6-(trifluoromethyl)-3H-imidazo[4,5-b]pyridine To a mixed solution of 397 mg of the pale yellow solid obtained in step 2 and 10 ml of 1,2-dichloroethane, at room temperature, 274 mg of N-chlorosuccinimide was added. After the addition, the mixture was stirred under reflux with heating for 1.5 hours. After the stirring, to the reaction mixture, 1,096 mg of N-chlorosuccinimide was added at room temperature. After the addition, the reaction mixture was stirred under reflux with heating for 1.5 hours. After the completion of the reaction, the solvent was evaporated under reduced pressure. The resulting residue was purified by preparative medium pressure liquid chromatography (chloroform:methanol with a gradient of from 100:0 to 85:15) to obtain 284 mg of the desired product as a pale yellow solid.

$^1$H-NMR (CDCl$_3$): δ8.85-8.80 (m, 1H), 8.45-8.40 (m, 1H), 8.09 (s, 1H), 7.82 (d, J=9.3 Hz, 1H), 7.39 (d, J=9.3 Hz, 1H), 4.04 (s, 3H).

Step 4: Synthesis of 2-[3-(ethylthio)-6-(trifluoromethyl)-2H-indazol-2-yl]-3-methyl-6-(trifluoromethyl)-3H-imidazo[4,5-b]pyridine (Compound No. 1-10-001 b of the Present Invention)

To a mixed solution of 284 mg of the pale yellow solid obtained in step 3 and 1.3 ml of N,N-dimethylformamide, at room temperature, 85 mg of sodium ethanethiolate was added. After the addition, the mixture was stirred at 70° C. for 4 hours. After the completion of the reaction, the reaction mixture was mixed with 5 ml of water and extracted with chloroform (5 ml×2). The resulting organic layer was dried over anhydrous sodium sulfate, and the solvent was evaporated under reduced pressure. The resulting residue was purified by preparative medium pressure liquid chromatography (chloroform:methanol with a gradient of from 95:5 to 90:10) to obtain 86 mg of the desired product as a pale yellow solid.

$^1$H-NMR (CDCl$_3$): δ8.84 (s, 1H), 8.39 (s, 1H), 8.31 (d, J=9.3 Hz, 1H), 8.25 (s, 1H), 7.61 (d, J=9.3 Hz, 1H), 3.91 (s, 3H), 3.85 (q, J=7.5 Hz, 2H), 1.46 (t, J=7.5 Hz, 3H).

Synthetic Example 6: Synthesis of 2-[3-(ethylsulfonyl)-6-(trifluoromethyl)-2H-indazol-2-yl]-3-methyl-6-(trifluoromethyl)-3H-imidazo[4,5-b]pyridine (Compound No. 1-10-001a of the Present Invention)

To a mixed solution of 86 mg of compound No. 1-10-001 b of the present invention obtained in Synthetic Example 5 and 1.3 ml of chloroform, 76 mg of 65 mass % m-chloroperbenzoic acid (containing about 30 mass % of water) was added at room temperature. After the addition, the mixture was stirred at room temperature for 18 hours. After the completion of the reaction, the reaction mixture was mixed with 3 ml of a saturated sodium thiosulfate aqueous solution and extracted with chloroform (5 ml×2). The resulting organic layer was dried over anhydrous sodium sulfate, and the solvent was evaporated under reduced pressure. The resulting residue was purified by preparative medium pressure liquid chromatography (chloroform:methanol with a gradient of from 100:0 to 90:10) to obtain 70 mg of the desired product as a pale yellow solid.

Melting point: 133 to 135° C.

$^1$H-NMR (CDCl$_3$): δ8.83 (d, J=1.8 Hz, 1H), 8.38 (d, J=1.5 Hz, 1H), 8.30 (d, J=9.0 Hz, 1H), 8.25 (d, J=0.9 Hz, 1H), 7.60 (dd, J=9.0, 1.2 Hz, 1H), 3.91 (s, 3H), 3.85 (q, J=7.2 Hz, 2H), 1.46 (t, J=7.2 Hz, 3H).

Synthetic Example 7: Synthesis of 2-[3-(ethylthio)-6-nitro-2H-indazol-2-yl]-3-methyl-6-(trifluoromethyl)-3H-imidazo[4,5-b]pyridine (Compound No. 1-10-002b of the Present Invention)

Step 1: Synthesis of 2-azido-N-[3-methyl-6-(trifluoromethyl)-3H-imidazo[4,5-b]pyridin-2-yl]-4-nitrobenzamide To a mixed solution of 248 mg of 3-methyl-6-(trifluoromethyl)-3H-imidazo[4,5-b]pyridin-2-amine, 159 mg of 2-azide-4-nitrobenzoic acid, 445 mg of diisopropylethylamine and 5 ml of N,N-dimethylformamide, 437 mg of O-(7-azabenzotriazol-1-yl-)-N,N,N',N'-tetramethyluronium hexafluorophosphate (HATU) was added at room temperature. After the addition, the mixture was stirred at room temperature for 48 hours. After the completion of the reaction, the reaction mixture was mixed with 10 ml of water and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography (n-hexane:ethyl acetate with a gradient of from 100:0 to 0:100) to obtain 175 mg of the desired product as an orange solid.

$^1$H-NMR (CDCl$_3$): δ8.65-8.55 (m, 1H), 8.22 (d, J=8.4 Hz, 1H), 8.08 (d, J=2.0 Hz, 1H), 8.03 (dd, J=8.4, 2.0 Hz, 1H), 7.85-7.75 (m, 1H), 3.83 (s, 3H) (No signal assigned to proton of NH was observed).

Step 2: Synthesis of 2-[3-chloro-6-nitro-2H-indazol-2-yl]-3-methyl-6-(trifluoromethyl)-3H-imidazo[4,5-b]pyridine To 175 mg of the orange solid obtained in step 1, at room temperature, 3 g of phosphorus oxychloride was added. After the addition, the mixture was stirred at 100° C. for 2 hours. After the completion of the reaction, the reaction mixture was cooled to room temperature. The reaction mixture was added dropwise to ice water, and the mixture was extracted with chloroform (20 ml×2). The resulting organic layer was dried over anhydrous sodium sulfate, and the solvent was evaporated under reduced pressure. The resulting residue was purified by preparative medium pressure liquid chromatography (n-hexane:ethyl acetate with a gradient of from 100:0 to 0:100) to obtain 102 mg of the desired product as a yellow solid.

$^1$H-NMR (CDCl$_3$): δ8.83 (d, J=1.5 Hz, 1H), 8.75 (d, J=1.8 Hz, 1H), 8.45 (d, J=1.5 Hz, 1H), 8.03 (dd, J=9.6, 1.8 Hz, 1H), 7.86 (d, J=9.6 Hz, 1H), 4.07 (s, 3H).

Step 3: Synthesis of 2-[3-(ethylthio)-6-nitro-2H-indazol-2-yl]-3-methyl-6-(trifluoromethyl)-3H-imidazo[4,5-b]pyridine (Compound No. 1-10-002b of the Present Invention)

To a mixed solution of 102 mg of the yellow solid obtained in step 2 and 2 ml of 1,4-dioxane, 80 mg of diisopropylethylamine, 30 mg of 4,5-bis(diphenylphosphino)-9,9-dimethylxanthene, 24 mg of tris(dibenzilideneacetone)dipalladium(0) and 19 mg of ethanethiol were successively added at room temperature. After the addition, the mixture was stirred under reflux with heating in a nitrogen atmosphere for 2 hours. After the completion of the reaction, the reaction mixture was mixed with 10 ml of water and extracted with chloroform (10 ml×2). The resulting organic layer was dried over anhydrous sodium sulfate, and the solvent was evaporated under reduced pressure. The resulting residue was purified by preparative medium pressure liquid chromatography (n-hexane:ethyl acetate with a gradient of from 100:0 to 70:30) to obtain 108 mg of the desired product as a yellow oil.

$^1$H-NMR (CDCl$_3$): δ8.85-8.75 (m, 2H), 8.44 (d, J=1.8 Hz, 1H), 8.06 (dd, J=9.2, 1.8 Hz, 1H), 7.98 (dd, J=9.2, 0.7 Hz, 1H), 3.91 (s, 3H), 3.10 (q, J=7.4 Hz, 2H), 1.24 (t, J=7.4 Hz, 3H).

Synthetic Example 8: Synthesis of 2-[3-(ethylsulfonyl)-5-(trifluoromethyl)pyrazolo[1,5-a]pyridin-2-yl]-7-(perfluoroethyl)imidazo[1,2-c]pyrimidine (Compound No. 1-3-001a of the Present Invention)

Step 1: Synthesis of ethyl 3-iodo-5-(trifluoromethyl)pyrazolo[1,5-a]pyridine-2-carboxylate To a mixed solution of 4.49 g of ethyl 5-(trifluoromethyl)pyrazolo[1,5-a]pyridine-2-carboxylate and 60 ml of N,N-dimethylformamide, 5.95 g of 1,3-diiodo-5,5-dimethylhydantoin was added at room temperature. After the addition, the mixture was stirred at 80° C. for 7 hours. After the completion of the reaction, the reaction mixture was mixed with water, and the precipitated solid was collected by filtration. The obtained solid was dissolved in 40 ml of chloroform, followed by washing with a saturated sodium thiosulfate aqueous solution and then with saturated sodium hydrogen carbonate. The resulting organic layer was dried over anhydrous sodium sulfate, and the solvent was evaporated under reduced pressure to obtain 6.11 g of the desired product as a pale brown solid.

Melting point: 147 to 150° C.

$^1$H-NMR (CDCl$_3$): δ8.62 (d, J=7.2 Hz, 1H), 7.93 (s, 1H), 7.11 (dd, J=7.2, 2.0 Hz, 1H), 4.54 (q, J=7.2 Hz, 2H), 1.49 (t, J=7.2 Hz, 3H).

Step 2: Synthesis of 3-(ethylthio)-5-(trifluoromethyl)pyrazolo[1,5-a]pyridine-2-carboxylic acid To a mixed solution of 6.11 g of the pale brown solid obtained in step 1 and 50 ml of 1,4-dioxane, 6.17 g of diisopropylethylamine, 920 mg of 4,5-bis(diphenylphosphino)-9,9-dimethylxanthene, 728 mg of tris(dibenzilideneacetone)dipalladium(0) and 1.48 g of ethanethiol were successively added. After the addition, the atmosphere in the reaction vessel was replaced with nitrogen gas, and the mixture was stirred under reflux with heating for 2 hours. After the completion of the reaction, the reaction mixture was subjected to filtration through Celite, and the Celite was washed with 50 ml of 1,4-dioxane. The resulting filtrate and washing liquid were put together, and the solvent was evaporated under reduced pressure to obtain crude ethyl 3-(ethylthio)-5-(trifluoromethyl)pyrazolo[1,5-a]pyridine-2-carboxylate. To a mixed solution of the obtained crude ethyl 3-(ethylthio)-5-(trifluoromethyl)pyrazolo[1,5-a]pyridine-2-carboxylate and 50 ml of ethanol, 20 ml of a 1.5 mol/L sodium hydroxide aqueous solution was added at room temperature. After the addition, the reaction mixture was stirred at room temperature for 3 hours. After the completion of the reaction, the solvent was evaporated under reduced pressure. The resulting residue was mixed with a 1 mol/L hydrochloric acid aqueous solution to adjust the aqueous layer to have a pH of 2, and extracted with chloroform (20 ml×2). The resulting organic layer was dried over anhydrous sodium sulfate, and the solvent was evaporated under reduced pressure to obtain 4.73 g of the desired product as a brown solid.

Melting point: 195 to 205° C.

$^1$H-NMR (DMSO-d6): δ9.02 (d, J=7.2 Hz, 1H), 8.11 (s, 1H), 7.39 (d, J=7.2 Hz, 1H), 2.85 (q, J=7.2 Hz, 2H), 1.06 (t, J=7.2 Hz, 3H) (No signal assigned to proton of CO$_2$H was observed).

Step 3: Synthesis of 3-(ethylthio)-N-methoxy-N-methyl-5-(trifluoromethyl)pyrazolo[1,5-a]pyridine-2-carboxamide To a mixed solution of 2.70 g of the brown solid obtained in step 2 and 60 ml of dichloromethane, 2.95 g of oxalyl chloride and 30 mg of N,N-dimethylformamide were successively added under cooling with ice. After the addition, the mixture was stirred at room temperature for 5 hours. After the stirring, the solvent was evaporated from the reaction mixture under reduced pressure to obtain crude 3-(ethylthio)-5-(trifluoromethyl)pyrazolo[1,5-a]pyridine-2-carboxylic acid chloride. A mixed solution of the obtained crude 3-(ethylthio)-5-(trifluoromethyl)pyrazolo[1,5-a]pyridine-2-carboxylic acid chloride and 20 ml of dichloromethane was added under cooling with ice to a mixed solution of 692 mg of N,O-dimethylhydroxylamine hydrochloride, 1.63 g of triethylamine and 20 ml of dichloromethane prepared in a separate container. After the addition, the mixture was stirred at room temperature for 16 hours. After the completion of the reaction, the reaction mixture was mixed with 10 ml of water and extracted with chloroform (10 ml×2). The resulting organic layer was washed with a 1 mol/L hydrochloric acid aqueous solution and then with a saturated sodium hydrogen carbonate aqueous solution and dried over anhydrous sodium sulfate, and the solvent was evaporated under reduced pressure to obtain 1.98 g of the desired product as a brown oil.

$^1$H-NMR (CDCl$_3$): δ8.53 (d, J=7.2 Hz, 1H), 8.06 (s, 1H), 7.04 (dd, J=7.2, 1.9 Hz, 1H), 3.71 (brs, 3H), 3.42 (s, 3H), 2.81 (q, J=7.2 Hz, 2H), 1.19 (t, J=7.2 Hz, 3H).

Step 4: Synthesis of 1-[3-(ethylthio)-5-(trifluoromethyl)pyrazolo[1,5-a]pyridin-2-yl]ethan-1-one In a nitrogen atmosphere, to a mixed solution of 1.98 g of the brown oil obtained in step 3 and 25 ml of tetrahydrofuran, 4.2 ml of a diethyl ether solution of about 3 mol/L methyl magnesium bromide (manufactured by Tokyo Chemical Industry Co., Ltd.) was added under cooling with ice. After the addition, the mixture was stirred under cooling with ice for 1 hour. After the completion of the reaction, the reaction mixture was added dropwise to 10 ml of a 4 mol/L hydrochloric acid aqueous solution under cooling with ice, and extracted with chloroform (20 ml×2). The resulting organic layer was washed with a saturated sodium hydrogen carbonate aqueous solution, dehydrated with saturated aqueous sodium chloride and dried over anhydrous sodium sulfate, and the solvent was evaporated under reduced pressure to obtain 1.81 g of the desired product as a brown solid.

Melting point: 88 to 90° C.

$^1$H-NMR (CDCl$_3$): δ8.53 (d, J=7.2 Hz, 1H), 8.12 (s, 1H), 7.09 (dd, J=7.2, 2.0 Hz, 1H), 2.93 (q, J=7.5 Hz, 2H), 2.76 (s, 3H), 1.16 (t, J=7.5 Hz, 3H).

Step 5: Synthesis of 1-[3-(ethylsulfonyl)-5-(trifluoromethyl)pyrazolo[1,5-a]pyridin-2-yl]ethan-1-one To a mixed solution of 1.75 g of the brown solid obtained in step 4 and 20 ml of chloroform, 3.48 g of 65 mass % m-chloroperbenzoic acid (containing about 30 mass % of water) was added under cooling with ice. After the addition, the mixture was stirred at room temperature for 2 hours. After the completion of the reaction, the reaction mixture was mixed with 10 ml of a saturated sodium thiosulfate aqueous solution and extracted with chloroform (20 ml×2). The resulting organic layer was washed with 20 ml of a 1 mol/L sodium hydroxide aqueous solution. The organic layer was dried over anhydrous sodium sulfate, and the solvent was evaporated under reduced pressure. The resulting residue was purified by preparative medium pressure liquid chromatography (n-hexane:ethyl acetate with a gradient of from 100:0 to 50:50) to obtain 1.18 g of the desired product as a white solid.

Melting point: 123 to 125° C.

1H-NMR (CDCl$_3$): δ8.72-8.68 (m, 1H), 8.64 (d, J=7.2 Hz, 1H), 7.28 (dd, J=7.2, 2.0 Hz, 1H), 3.71 (q, J=7.3 Hz, 2H), 2.77 (s, 3H), 1.33 (t, J=7.3 Hz, 3H).

Step 6: Synthesis of 2-bromo-1-[3-(ethylsulfonyl)-5-(trifluoromethyl)pyrazolo[1,5-a]pyridin-2-yl] ethan-1-one To a mixed solution of 1.15 g of the white solid obtained in step 5 and 15 ml of toluene, 6.0 g of an acetic acid solution of about 5.1 mol/L hydrogen bromide (manufactured by Tokyo Chemical Industry Co., Ltd.) and 631 mg of bromine were successively added at room temperature. After the addition, the mixture was stirred at room temperature for 16 hours. After the completion of the reaction, the reaction mixture was mixed with 10 ml of water and extracted with ethyl acetate (20 ml×2). The resulting organic layer was washed with a 5 mass % sodium hydrogen sulfite aqueous solution. The organic layer was dried over anhydrous sodium sulfate, and the solvent was evaporated under reduced pressure to obtain 890 mg of the desired product as a white solid.

Melting point: 204 to 206° C.

1H-NMR (CDCl$_3$): δ8.72 (s, 1H), 8.65 (d, J=6.8 Hz, 1H), 7.33 (dd, J=6.8, 2.0 Hz, 1H), 4.72 (s, 2H), 3.69 (q, J=7.3 Hz, 2H), 1.35 (t, J=7.3 Hz, 3H).

Step 7: Synthesis of 2-[3-(ethylsulfonyl)-5-(trifluoromethyl)pyrazolo[1,5-a]pyridin-2-yl]-7-(perfluoroethyl)imidazo[1,2-c]pyrimidine (Compound No. 1-3-001a of the Present Invention)

To a mixed solution of 117 mg of 6-(perfluoroethyl)pyrimidin-4-amine and 5 ml of chlorobenzene, 200 mg of the white solid obtained in step 6 was added at room temperature. After the addition, the mixture was stirred under reflux with heating for 6 hours. After the completion of the reaction, the reaction mixture was mixed with 10 ml of a 1 mol/L sodium hydroxide aqueous solution and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography (n-hexane:ethyl acetate with a gradient of from 100:0 to 50:50) to obtain 44 mg of the desired product as a white solid.

Melting point: 290 to 296° C.

$^1$H-NMR (CDCl$_3$): δ9.21 (s, 1H), 8.81 (s, 1H), 8.76 (d, J=7.2 Hz, 1H), 8.65 (s, 1H), 8.05 (s, 1H), 7.30-7.28 (m, 1H), 3.48 (q, J=7.5 Hz, 2H), 1.31 (t, J=7.5 Hz, 3H).

Synthetic Example 9: Synthesis of 6-[3-(ethylsulfonyl)-5-(trifluoromethyl)pyrazolo[1,5-a]pyridin-2-yl]-2-(perfluoroethyl)imidazo[2,1-b][1,3,4]thiadiazole (Compound No. 1-5-001a of the Present Invention)

To a mixed solution of 120 mg of 5-(perfluoroethyl)-1,3,4-thiadiazol-2-amine and 5 ml of chlorobenzene, 200 mg of the white solid obtained in step 6 in Synthetic Example 8 was added at room temperature. After the addition, the mixture was stirred under reflux with heating for 6 hours. After the completion of the reaction, the reaction mixture was mixed with 10 ml of a 1 mol/L sodium hydroxide aqueous solution and extracted with ethyl acetate (10 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography (n-hexane:ethyl acetate with a gradient of from 100:0 to 50:50) to obtain 134 mg of the desired product as a white solid.

Melting point: 249 to 250° C.

$^1$H-NMR (CDCl$_3$): δ8.93 (s, 1H), 8.71 (d, J=7.2 Hz, 1H), 8.62 (s, 1H), 7.24 (dd, J=7.2, 2.0 Hz, 1H), 3.46 (q, J=7.3 Hz, 2H), 1.31 (t, J=7.3 Hz, 3H).

Synthetic Example 10: Synthesis of 2-[3-(ethylthio)-5-(trifluoromethyl)pyrazolo[1,5-a]pyridin-2-yl]-7-(trifluoromethyl)-[1,2,4]triazolo[1,5-a]pyridine (Compound No. 1-4-001 b of the Present Invention)

Step 1: Synthesis of 1,2-diamino-4-(trifluoromethyl)pyridin-1-ium 2,4,6-trimethylbenzenesulfonate To 8.8 g of trifluoroacetic acid, 2.0 g of tert-butyl [(mesitylsulfonyl)oxy]carbamate was added under cooling with ice. After the addition, the mixture was stirred under cooling with ice for 2 hours. After the stirring, ice water was added to the reaction mixture. After the addition, the precipitated solid was collected by filtration. The obtained solid was dissolved in 20 ml of dichloromethane and dried over anhydrous sodium sulfate, and the anhydrous sodium sulfate was removed by filtration. To the obtained filtrate, 740 mg of 4-(trifluoromethyl)pyridin-2-amine was added under cooling with ice. After the addition, the mixture was stirred at room temperature for 16 hours. After the stirring, the solid precipitated in the reaction mixture was collected by filtration. The obtained solid was washed with diethyl ether to obtain 1.1 g of the desired product as a white solid.

Melting point: 202 to 205° C.

Step 2: Synthesis of 2-[3-(ethylthio)-5-(trifluoromethyl)pyrazolo[1,5-a]pyridin-2-yl]-7-(trifluoromethyl)-[1,2,4]triazolo[1,5-a]pyridine (Compound No. 1-4-001 b of the Present Invention)

To a mixed solution of 90 mg of the white solid obtained in step 1 and 2 ml of pyridine, 87 mg of 3-(ethylthio)-5-(trifluoromethyl)pyrazolo[1,5-a]pyridine-2-carboxylic acid and 73 mg of 1-ethyl-3-(3-dimethylaminopropyl)carbodiimide hydrochloride were successively added at room temperature. After the addition, the mixture was stirred under reflux with heating for 5 hours. After the completion of the reaction, the solvent was evaporated under reduced pressure. The resulting residue was mixed with 20 ml of water and extracted with ethyl acetate (20 ml×2). The resulting organic layer was dehydrated with saturated aqueous sodium chloride and dried over anhydrous sodium sulfate, and the solvent was evaporated under reduced pressure. The resulting residue was purified by preparative medium pressure liquid chromatography (n-hexane:ethyl acetate with a gradient of from 100:0 to 50:50) to obtain 40 mg of the desired product as a pale yellow solid.

$^1$H-NMR (CDCl$_3$): δ8.85 (d, J=7.2 Hz, 1H), 8.67 (d, J=7.2 Hz, 1H), 8.21-8.13 (m, 2H), 7.29 (dd, J=7.2, 1.5 Hz, 1H), 7.08 (dd, J=7.2, 1.5 Hz, 1H), 3.01 (q, J=7.5 Hz, 2H), 1.20 (t, J=7.5 Hz, 3H).

The compounds of the present invention may be synthesized in accordance with the above Processes and Synthetic Examples. Examples of condensed heterocyclic compounds produced in the same manner as in Synthetic Examples 1 to 10 are shown in Tables 2 to 8, however, the condensed heterocyclic compounds of the present invention are not limited thereto.

In Tables, "Me" represents a methyl group, "Et" an ethyl group, and "Ph" a phenyl group. Further, in Tables, "*1" represents that the compound is a solid, "*2" represents that the compound is an oil or in a resin state, and "m.p." represents the melting point (unit: ° C.).

In Table, G2-2 represents the following cyclic structure, and the symbol in the bracket represents the number, the type and the substitution position of the substituent ($Z^2$).

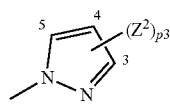

G2-2

TABLE 2

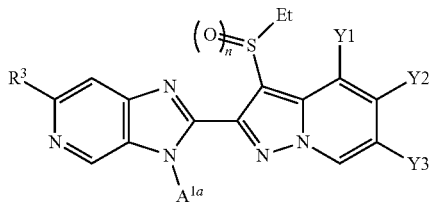

| No. | $R^3$ | $A^{1a}$ | Y1 | Y2 | Y3 | n | m.p. |
|---|---|---|---|---|---|---|---|
| 1-1-001a | $CF_3$ | Me | H | H | Cl | 2 | 132-136 |
| 1-1-001b | $CF_3$ | Me | H | H | Cl | 0 | *1 |
| 1-1-002a | $CF_3$ | Me | H | H | I | 2 | 203-205 |
| 1-1-002b | $CF_3$ | Me | H | H | I | 0 | 144-146 |
| 1-1-003a | $CF_3$ | Me | H | H | G2-2[3-$CF_3$] | 2 | 226-229 |
| 1-1-004a | $CF_3$ | Me | H | H | $CF_3$ | 2 | *2 |
| 1-1-004b | $CF_3$ | Me | H | H | $CF_3$ | 0 | *1 |
| 1-1-005a | $CF_3$ | Me | H | H | Br | 2 | 190-192 |
| 1-1-005b | $CF_3$ | Me | H | H | Br | 0 | *1 |
| 1-1-006a | $CF_3$ | Me | H | Cl | H | 2 | 216-217 |
| 1-1-006b | $CF_3$ | Me | H | Cl | H | 0 | *1 |
| 1-1-007a | $CF_3$ | Me | H | Br | H | 2 | 226-229 |
| 1-1-007b | $CF_3$ | Me | H | Br | H | 0 | *1 |
| 1-1-008a | $CF_3$ | Me | H | I | H | 2 | 236-238 |
| 1-1-009a | $CF_3$ | Me | H | Ph | H | 2 | 235-237 |
| 1-1-010a | $CF_3$ | Me | H | H | H | 2 | *2 |
| 1-1-011a | $CF_3$ | Me | I | H | H | 2 | 240-249 |
| 1-1-011b | $CF_3$ | Me | I | H | H | 0 | *1 |
| 1-1-012a | $CF_3$ | Me | H | $CF_3$ | H | 2 | 227-229 |
| 1-1-012b | $CF_3$ | Me | H | $CF_3$ | H | 0 | 131-132 |
| 1-1-013a | $CF_3$ | Me | H | SMe | H | 2 | 164-166 |
| 1-1-014a | $CF_3$ | Me | H | SOMe | H | 2 | 206-208 |
| 1-1-015a | $CF_3$ | Me | H | $SO_2Me$ | H | 2 | 231-233 |
| 1-1-016a | $SCF_3$ | Me | H | $CF_3$ | H | 2 | 210-212 |
| 1-1-016b | $SCF_3$ | Me | H | $CF_3$ | H | 0 | 127-129 |
| 1-1-017a | $SOCF_3$ | Me | H | $CF_3$ | H | 2 | 215-216 |

TABLE 3

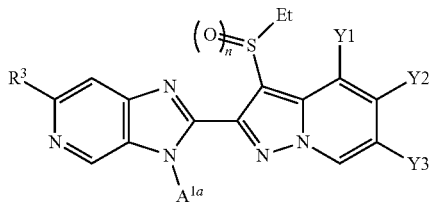

| No. | $R^3$ | $A^{1a}$ | Y1 | Y2 | Y3 | n | m.p. |
|---|---|---|---|---|---|---|---|
| 1-2-001a | $CF_3$ | Me | H | H | I | 2 | *1 |
| 1-2-001b | $CF_3$ | Me | H | H | I | 0 | *1 |
| 1-2-002a | $CF_3$ | Me | I | H | H | 2 | *2 |
| 1-2-002b | $CF_3$ | Me | I | H | H | 0 | *1 |

TABLE 4

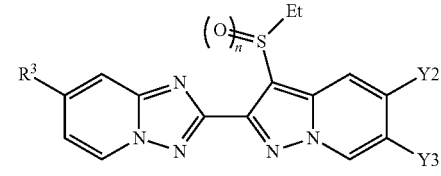

| No. | $R^3$ | $R^6$ | Y2 | Y3 | n | m.p. |
|---|---|---|---|---|---|---|
| 1-3-001a | $CF_2CF_3$ | H | $CF_3$ | H | 2 | 290-296 |

TABLE 5

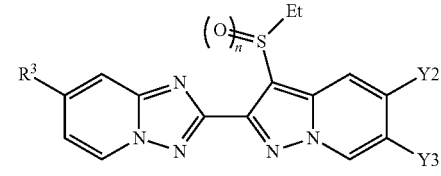

| No. | $R^3$ | Y2 | Y3 | n | m.p. |
|---|---|---|---|---|---|
| 1-4-001a | $CF_3$ | $CF_3$ | H | 2 | *1 |
| 1-4-001b | $CF_3$ | $CF_3$ | H | 0 | *1 |

TABLE 6

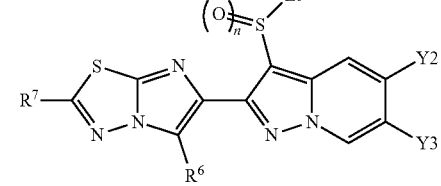

| No. | $R^7$ | $R^6$ | Y2 | Y3 | n | m.p. |
|---|---|---|---|---|---|---|
| 1-5-001a | $CF_2CF_3$ | H | $CF_3$ | H | 2 | 249-250 |

TABLE 7

| No. | R³ | A^{1a} | Y2 | Y3 | n | m.p. |
|---|---|---|---|---|---|---|
| 1-10-001a | CF₃ | Me | H | CF₃ | 2 | 133-135 |
| 1-10-001b | CF₃ | Me | H | CF₃ | 0 | *1 |
| 1-10-002a | CF₃ | Me | H | NO₂ | 2 | *2 |
| 1-10-002b | CF₃ | Me | H | NO₂ | 0 | *2 |
| 1-10-003a | CF₃ | Me | H | I | 2 | *1 |
| 1-10-004a | CF₃ | Me | H | NH₂ | 2 | *2 |

TABLE 8

| No. | R³ | A^{1a} | Y2 | Y3 | n | m.p. |
|---|---|---|---|---|---|---|
| 1-11-001a | CF₃ | Me | H | CF₃ | 2 | 238-240 |
| 1-11-001b | CF₃ | Me | H | CF₃ | 0 | 144-146 |

Examples of production intermediates for production of the compounds of the present invention shown in Tables 1 to 8 are shown in Tables 9 to 11, however, the production intermediates are not limited thereto.

In Tables, "Me" represents a methyl group.

TABLE 9

| No. | R³ | A^{1a} | Y1 | Y2 | Y3 | J₁ | m.p. |
|---|---|---|---|---|---|---|---|
| 1-1-001 | CF₃ | Me | H | H | Cl | H | 238-240 |
| 1-1-002 | CF₃ | Me | H | H | I | H | *1 |
| 1-1-003 | CF₃ | Me | H | H | Br | H | *1 |
| 1-1-004 | CF₃ | Me | H | H | CF₃ | H | *1 |
| 1-1-005 | CF₃ | Me | H | H | CF₃ | I | *1 |
| 1-1-006 | CF₃ | Me | H | Cl | H | H | 207-210 |
| 1-1-007 | CF₃ | Me | H | Br | H | H | 221-223 |
| 1-1-008 | CF₃ | Me | H | Cl | H | Cl | 252-253 |

TABLE 10

| No. | R³ | A^{1a} | A⁴ | A⁵ | Y2 | Y3 | J₁ | m.p. |
|---|---|---|---|---|---|---|---|---|
| 1-10-001 | CF₃ | Me | CH | N | H | CF₃ | H | 168-175 |
| 1-10-002 | CF₃ | Me | CH | N | H | CF₃ | Cl | *1 |
| 1-10-003 | CF₃ | Me | CH | N | H | NO₂ | Cl | *1 |
| 1-10-004 | CF₃ | Me | N | CH | H | CF₃ | H | *1 |
| 1-10-005 | CF₃ | Me | N | CH | H | CF₃ | Cl | 131-134 |

TABLE 11

| No. | R³ | A^{1a} | A⁴ | A⁵ | m.p. |
|---|---|---|---|---|---|
| 1-11-001 | CF₃ | Me | CH | N | *1 |
| 1-11-002 | CF₃ | Me | N | CH | 152-154 |

¹H-NMR data of the compounds of the present invention and production intermediates of which the melting point is not described, are shown in Table 12. The proton nuclear magnetic resonance chemical shift values were measured by using Me₄Si (tetramethylsilane) as a standard substance in deuterated chloroform solvent at 300 MHz (ECX300 or ECP300, manufactured by JEOL Ltd.).

Reference symbols in the proton nuclear magnetic resonance chemical shift values have the following meanings.

s: singlet, brs: broad singlet, d: doublet, dd: double doublet, t: triplet, q: quartet, m: multiplet

TABLE 12

| No. | ¹H NMR (CDCl₃, Me₄Si, 300 MHz). |
|---|---|
| 1-1-002a | δ 8.92-8.88 (m, 1H), 8.77-8.73 (m, 1H), 8.36 (d, J = 1.8 Hz, 1H), 8.15 (dd, J = 9.6, 0.6 Hz, 1H), 7.71 (dd, J = 9.6, 1.5 Hz, 1H), 4.11 (s, 3H), 3.93 (q, J = 7.5 Hz, 2H), 1.39 (t, J = 7.5 Hz, 3H). |
| 1-1-002b | δ 8.83-8.80 (m, 1H), 8.75-8.71 (m, 1H), 8.42-8.39 (m, 1H), 7.66 (dd, J = 9.3, 1.2 Hz, 1H), 7.50 (dd, J = 9.3, 1.2 Hz, 1H), 4.18 (s, 3H), 2.92 (q, J = 7.2 Hz, 2H), 1.13 (t, J = 7.2 Hz, 3H). |
| 1-1-004a | δ 8.98 (s, 1H), 8.80-8.76 (m, 1H), 8.52 (d, J = 9.6 Hz, 1H), 8.39 (d, J = 1.8 Hz, 1H), 7.70 (d, J = 9.6 Hz, 1H), 4.16 (s, 3H), 3.99 (q, J = 7.5 Hz, 2H), 1.42 (t, J = 7.5 Hz, 3H). |
| 1-1-005a | δ 8.79-8.73 (m, 2H), 8.38-8.34 (m, 1H), 8.28 (dd, J = 10.5, 0.9 Hz, 1H), 7.62 (dd, J = 9.3, 1.5 Hz, 1H), 4.12 (s, 3H), 3.94 (q, J = 7.5 Hz, 2H), 1.39 (t, J = 7.5 Hz, 3H). |

TABLE 12-continued

| No. | ¹H NMR (CDCl₃, Me₄Si, 300 MHz). |
|---|---|
| 1-1-005b | δ 8.74-8.71 (m, 1H), 8.69-8.67 (m, 1H), 8.40 (d, J = 2.1 Hz, 1H), 7.76 (dd, J = 9.0, 0.6 Hz, 1H), 7.39 (dd, J = 9.6, 1.8 Hz, 1H), 4.18 (s, 3H), 2.92 (q, J = 7.5 Hz, 2H), 1.13 (t, J = 7.5 Hz, 3H). |
| 1-1-006a | δ 8.79-8.70 (m, 1H), 8.53 (dd, J = 7.4, 0.6 Hz, 1H), 8.40-8.27 (m, 2H), 7.13 (dd, J = 7.4, 2.1 Hz, 1H), 4.12 (s, 3H), 3.93 (q, J = 7.5 Hz, 2H), 1.41 (t, J = 7.5 Hz, 3H). |
| 1-1-006b | δ 8.74 (s, 1H), 8.49-8.36 (m, 2H), 7.85 (d, J = 2.0 Hz, 1H), 6.94 (dd, J = 7.5, 2.0 Hz, 1H), 4.18 (s, 3H), 2.91 (q, J = 7.5 Hz, 2H), 1.15 (t, J = 7.5 Hz, 3H). |
| 1-1-007a | δ 8.79-8.74 (m, 1H), 8.57 (dd, J = 2.2, 0.9 Hz, 1H), 8.48-8.43 (m, 1H), 8.40-8.34 (m, 1H), 7.27-7.24 (m, 1H), 4.12 (s, 3H), 3.92 (q, J = 7.2 Hz, 2H), 1.41 (t, J = 7.2 Hz, 3H). |
| 1-1-007b | δ 8.74 (s, 1H), 8.50-8.35 (m, 2H), 8.10-8.00 (m, 1H), 7.13-7.00 (m, 1H), 4.18 (s, 3H), 2.92 (q, J = 7.5 Hz, 2H), 1.14 (t, J = 7.5 Hz, 3H). |
| 1-1-008a | δ 8.81-8.73 (m, 2H), 8.40-8.27 (m, 2H), 7.44-7.37 (m, 1H), 4.11 (s, 3H), 3.91 (q, J = 7.5 Hz, 2H), 1.41 (t, J = 7.5 Hz, 3H). |
| 1-1-009a | δ 8.76 (d, J = 1.7 Hz, 1H), 8.65 (d, J = 7.2 Hz, 1H), 8.54-8.48 (m, 1H), 8.37 (d, J = 1.7 Hz, 1H), 8.28-8.23 (m, 1H), 7.77-7.73 (m, 1H), 7.63-7.40 (m, 4H), 4.13 (s, 3H), 3.89 (q, J = 7.5 Hz, 2H), 1.42 (t, J = 7.5 Hz, 3H). |
| 1-1-010a | δ 8.80-8.75 (m, 1H) 8.67-8.59 (m, 1H), 8.42-8.33 (m, 2H), 7.62-7.53 (m, 1H), 7.22-7.14 (m, 1H), 4.12 (s, 3H), 3.88 (q, J = 7.5 Hz, 2H), 1.39 (t, J = 7.5 Hz, 3H). |
| 1-1-011a | δ 8.77-8.73 (m, 1H), 8.70 (dd, J = 7.2, 1.2 Hz, 1H), 8.35-8.32 (m, 1H), 8.26 (dd, J = 7.8, 1.5 Hz, 1H), 6.93 (dd, J = 6.9, 6.9 Hz, 1H), 3.90 (s, 3H), 3.72 (q, J = 7.5 Hz, 2H), 1.44 (t, J = 7.5 Hz, 3H). |
| 1-1-011b | δ 8.76-8.72 (m, 1H), 8.57 (d, J = 6.3 Hz, 1H), 8.40 (d, J = 2.1 Hz, 1H), 7.91 (d, J = 6.9 Hz, 1H), 6.71 (dd, J = 7.2, 7.2 Hz, 1H), 4.05 (s, 3H), 2.84 (q, J = 7.5 Hz, 2H), 1.13 (t, J = 7.5 Hz, 3H). |
| 1-2-001a | δ 8.99 (s, 1H), 8.91 (d, J = 0.9 Hz, 1H), 8.16 (s, 1H), 8.14 (d, J = 9.6 Hz, 1H), 7.75 (dd, J = 9.6, 1.2 Hz, 1H), 4.13 (s, 3H), 3.86 (q, J = 7.5 Hz, 2H), 1.38 (t, J = 7.5 Hz, 3H). |
| 1-1-012a | δ 8.81-8.67 (m, 3H), 8.39 (d, J = 2.0 Hz, 1H), 7.33 (dd, J = 7.5, 2.0 Hz, 1H), 4.15 (s, 3H), 4.00 (q, J = 7.2 Hz, 2H), 1.43 (t, J = 7.2 Hz, 3H). |
| 1-1-012b | δ 8.77-8.73 (m, 1H), 8.63 (d, J = 7.2 Hz, 1H), 8.45-8.40 (m, 1H), 8.25-8.16 (m, 1H), 7.13 (dd, J = 7.2, 2.0 Hz, 1H), 4.21 (s, 3H), 2.98 (q, J = 7.2 Hz, 2H), 1.16 (t, J = 7.2 Hz, 3H). |
| 1-1-013a | δ 8.77-8.73 (m, 1H), 8.41-8.35 (m, 2H), 7.93 (d, J = 2.0 Hz, 1H), 6.97 (dd, J = 7.2, 2.0 Hz, 1H), 4.10 (s, 3H), 3.87 (q, J = 7.5 Hz, 2H), 2.63 (s, 3H), 1.40 (t, J = 7.5 Hz, 3H). |
| 1-1-014a | δ 8.85-8.75 (m, 2H), 8.65-8.55 (m, 1H), 8.38 (d, J = 2.0 Hz, 1H), 7.54 (dd, J = 7.2, 2.0 Hz, 1H), 4.16 (s, 3H), 4.09-3.86 (m, 2H), 2.88 (s, 3H), 1.42 (t, J = 7.5 Hz, 3H). |
| 1-1-015a | δ 9.05-8.95 (m, 1H), 8.84-8.73 (m, 2H), 8.39 (d, J = 2.0 Hz, 1H), 7.62 (dd, J = 7.2, 2.0 Hz, 1H), 4.16 (s, 3H), 4.02 (q, J = 7.5 Hz, 2H), 3.21 (s, 3H), 1.44 (t, J = 7.5 Hz, 3H). |
| 1-1-016a | δ 8.80-8.67 (m, 3H), 8.45 (d, J = 2.0 Hz, 1H), 7.33 (dd, J = 7.2, 2.0 Hz, 1H), 4.14 (s, 3H), 4.01 (q, J = 7.2 Hz, 2H), 1.43 (t, J = 7.2 Hz, 3H). |
| 1-1-016b | δ 8.69 (d, J = 2.0 Hz, 1H), 8.62 (d, J = 7.2 Hz, 1H), 8.49 (d, J = 2.0 Hz, 1H), 8.22-8.16 (m, 1H), 7.13 (dd, J = 7.2, 2.0 Hz, 1H), 4.20 (s, 3H), 2.99 (q, J = 7.2 Hz, 2H), 1.17 (t, J = 7.2 Hz, 3H). |
| 1-1-017a | δ 8.80 (d, J = 2.0 Hz, 1H), 8.77-8.66 (m, 2H), 8.62 (d, J = 1.4 Hz, 1H), 7.35 (dd, J = 7.5, 2.0 Hz, 1H), 4.18 (s, 3H), 4.00 (q, J = 7.2 Hz, 2H), 1.44 (t, J = 7.2 Hz, 3H). |
| 1-2-001b | δ 8.96 (s, 1H), 8.83-8.77 (m, 1H), 8.24-8.19 (m, 1H), 7.66 (d, J = 9.3 Hz, 1H), 7.54-7.48 (m, 1H), 4.20 (s, 3H), 2.91 (q, J = 7.5 Hz, 2H), 1.13 (t, J = 7.5 Hz, 3H). |
| 1-2-002a | δ 8.97 (s, 1H), 8.70 (dd, J = 6.9, 0.9 Hz, 1H), 8.27 (dd, J = 7.8, 1.2 Hz, 1H), 8.13 (d, J = 0.9 Hz, 1H), 6.94 (dd, J = 6.9, 6.9 Hz, 1H), 3.92 (s, 3H), 3.70 (q, J = 7.5 Hz, 2H), 1.42 (t, J = 7.5 Hz, 3H). |
| 1-2-002b | δ 8.97 (s, 1H), 8.60-8.55 (m, 1H), 8.20 (s, 1H), 7.94-7.88 (m, 1H), 7.62 (dd, J = 7.5, 7.5 Hz, 1H), 4.06 (s, 3H), 2.81 (q, J = 7.5 Hz, 2H), 1.11 (t, J = 7.5 Hz, 3H). |
| 1-4-001a | δ 8.88-8.72 (m, 3H), 8.20 (s, 1H), 7.37-7.26 (m, 2H), 4.01 (q, J = 7.5 Hz, 2H), 1.43 (t, J = 7.5 Hz, 3H). |
| 1-10-001b | δ 8.84 (s, 1H), 8.39 (s, 1H), 8.31 (d, J = 9.3 Hz, 1H), 8.25 (s, 1H), 7.61 (d, J = 9.3 Hz, 1H), 3.91 (s, 3H), 3.85 (q, J = 7.5 Hz, 2H), 1.46 (t, J = 7.5 Hz, 3H). |
| 1-10-002a | δ 9.00-8.80 (m, 2H), 8.40 (d, J = 2.0 Hz, 1H), 8.34 (d, J = 9.6 Hz, 1H), 8.23 (dd, J = 9.6, 1.8 Hz, 1H), 3.93 (s, 3H), 3.89 (q, J = 7.5 Hz, 2H), 1.47 (t, J = 7.5 Hz, 3H). |
| 1-10-003a | δ 8.85-8.80 (m, 1H), 8.40-8.30 (m, 2H), 7.90 (d, J = 9.0 Hz, 1H), 7.67 (dd, J = 9.0, 1.2 Hz, 1H), 3.88 (s, 3H), 3.82 (q, J = 7.4 Hz, 2H), 1.43 (t, J = 7.4 Hz, 3H). |
| 1-10-004a | δ 8.80-8.75 (m, 1H), 8.35-8.30 (m, 1H), 7.94 (d, J = 9.6 Hz, 1H), 6.92 (dd, J = 9.6, 1.8 Hz, 1H), 6.85-6.80 (m, 1H), 4.20-4.00 (brs, 2H), 3.89 (s, 3H), 3.80 (q, J = 7.4 Hz, 2H), 1.43 (t, J = 7.4 Hz, 3H). |
| 1-11-001a | δ 9.06 (s, 1H), 8.34-8.28 (m, 1H), 8.25 (s, 1H), 8.18 (s, 1H), 7.62 (dd, J = 9.0, 1.5 Hz, 1H), 3.93 (s, 3H), 3.83 (q, J = 7.2 Hz, 2H), 1.46 (t, J = 7.2 Hz, 3H). |
| 1-11-001b | δ 9.03 (s, 1H), 8.22 (s, 1H), 8.15 (s, 1H), 7.97 (d, J = 9.0 Hz, 1H), 7.43 (dd, J = 9.0, 1.2 Hz, 1H), 3.93 (s, 3H), 3.09 (q, J = 7.3 Hz, 2H), 1.24 (t, J = 7.3 Hz, 3H). |
| i-1-002 | δ 8.85-8.82 (m, 1H), 8.72-8.68 (m, 1H), 8.30 (d, J = 1.2 Hz, 1H), 7.44 (d, J = 0.9 Hz, 1H), 7.47-7.34 (m, 2H), 4.38 (s, 3H). |
| i-1-003 | δ 8.73-8.69 (m, 2H), 8.32 (s, 1H), 7.56 (d, J = 9.0 Hz, 1H), 7.38 (s, 1H), 7.33-7.26 (m, 1H), 4.40 (s, 3H). |

TABLE 12-continued

| No. | ¹H NMR (CDCl₃, Me₄Si, 300 MHz). |
|---|---|
| i-1-004 | δ 8.89 (s, 1H), 8.71 (d, J = 2.1 Hz, 1H), 8.32 (d, J = 2.1 Hz, 1H), 7.77 (d, J = 9.3 Hz, 1H), 7.46 (s, 1H), 7.36 (d, J = 9.3 Hz, 1H), 4.41 (s, 3H). |
| i-10-002 | δ 8.85-8.80 (m, 1H), 8.45-8.40 (m, 1H), 8.09 (s, 1H), 7.82 (d, J = 9.3 Hz, 1H), 7.39 (d, J = 9.3 Hz, 1H), 4.04 (s, 3H). |
| i-10-004 | δ 9.12 (s, 1H), 8.96 (s, 1H), 8.14 (s, 1H), 8.09 (s, 1H), 7.90 (d, J = 9.2 Hz, 1H), 7.35 (d, J = 9.2 Hz, 1H), 4.47 (s, 3H). |

Now, usefulness of the compounds of the present invention as pesticides will be described in detail by referring to the following Test Examples, but the present invention is by no means restricted thereto.

Test Example 1: Insecticidal Test on *Nilaparvata lugens*

10% emulsifiable concentrates (or 10% wettable powders) of compounds of the present invention were diluted with water containing a spreader to obtain 500 ppm solutions. Rice sheaths were soaked in the solutions for about 10 seconds. After the soaking, the rice sheaths were dried in air and put in test tubes. In each tube, five 3rd-instar larvae of *Nilaparvata lugens* were released, and the tubes were capped with sponge and placed in an incubator at 25° C. 6 days after, dead insects in the test tubes were counted, and the mortality was calculated in accordance with the following equation. The test was carried out in duplicate.

Mortality (%)=(the number of dead insects/the number of released insects)×100)

Among the compounds tested, the following compounds showed a mortality of at least 90%.
Compounds Nos. 1-1-004a, 1-1-005a, 1-1-013a, 1-1-014a, 1-1-015a, 1-2-001a, 1-2-002a, 1-10-001a and 1-11-001a of the present invention.

Test Example 2: Insecticidal Test on *Plutella xylostella*

10% emulsifiable concentrates (or 10% wettable powders) of compounds of the present invention were diluted with water containing a spreader to obtain 500 ppm solutions. Leaves of cabbage were soaked in the solutions for about 10 seconds. After the soaking, the leaves were dried in air and placed in dishes. In each dish, five 3rd-instar larvae of *Plutella xylostella* were released, and the dishes were covered with lids and placed in an incubator at 25° C. 6 days after, dead insects in the dishes were counted, and the mortality was calculated by using the same equation as in Test Example 1. The test was carried out in duplicate.
Among the compounds tested, the following compounds showed a mortality of at least 90%.
Compounds 1-1-001a, 1-1-002a, 1-1-002b, 1-1-003a, 1-1-004a, 1-1-005a, 1-1-006a, 1-1-006b, 1-1-007a, 1-1-008a, 1-1-009a, 1-1-010a, 1-1-011a, 1-1-012a, 1-1-012b, 1-1-013a, 1-1-014a, 1-1-015a, 1-1-016a, 1-1-016b, 1-1-017a, 1-2-001a, 1-3-001a, 1-4-001a, 1-5-001a, 1-10-001a, 1-10-003a, 1-11-001a and 1-11-001b of the present invention.

Test Example 3: Insecticidal Test on *Spodoptera litura*

10% emulsifiable concentrates (or 10% wettable powders) of compounds of the present invention were diluted with water containing a spreader to obtain 500 ppm solutions. Leaves of cabbage were soaked in the solutions for about 10 seconds. After the soaking, the leaves were dried in air and placed in dishes. In each dish, five 3rd-instar larvae of *Spodoptera litura* were released, and the dishes were covered with lids and placed in an incubator at 25° C. 6 days after, dead insects in the dishes were counted, and the mortality was calculated by using the same equation as in Test Example 1. The test was carried out in duplicate.
Among the compounds tested, the following compounds showed a mortality of at least 90%.
Compounds Nos. 1-1-001a, 1-1-002a, 1-1-002b, 1-1-003a, 1-1-004a, 1-1-005a, 1-1-006a, 1-1-006b, 1-1-007a, 1-1-008a, 1-1-009a, 1-1-010a, 1-1-011a, 1-1-012a, 1-1-012b, 1-1-013a, 1-1-014a, 1-1-015a, 1-1-016a, 1-1-016b, 1-1-017a, 1-2-001a, 1-3-001a, 1-4-001a, 1-5-001a, 1-10-001a, 1-10-003a, 1-11-001a and 1-11-001b of the present invention.

Test Example 4: Insecticidal Activity on *Frankliniella occidentalis*

In styrol cups having an inner diameter of 7 cm, wet filter paper was laid, kidney bean leaves cut into a 3 cm square were laid on the paper, and each leaf was inoculated with 20 larvae of *Frankliniella occidentalis*. 10% emulsifiable concentrates (or 10% wettable powders) of compounds of the present invention were diluted with water containing a spreader to obtain 500 ppm solutions. 2.5 ml of the solutions were sprayed from a rotary spray tower into the styrol cups (2.5 mg/cm²). 2 days after, dead insects were counted, and the insect damage degree on kidney bean leaves was examined. The mortality was calculated by using the same equation as in Test Example 1. The insect damage degree was evaluated from the proportion of the area with insect damage on the leaves, as follows. 1: 0 to 20% insect damage, 2: 20 to 50% insect damage, 3: 50 to 70% insect damage, and 4: 70% or higher insect damage. The test was carried out in duplicate.
Among the compounds tested, the following compounds showed a mortality of at least 50% and an insect damage degree of 2 or 1.
Compounds Nos. 1-1-002a, 1-1-004a, 1-1-006a, 1-1-006b, 1-1-007a, 1-1-008a, 1-1-012a, 1-1-012b, 1-1-013a, 1-1-014a, 1-1-015a, 1-1-016b, 1-2-001a and 1-3-001a of the present invention.

Test Example 5: Insecticidal Test on *Myzus persicae*

Wet absorbent cotton was laid on glass dishes having an inner diameter of 3 cm, and covered with leaves of cabbage cut into circles having a diameter of 3 cm, and 4 apterous adults of *Myzus persicae* were released. After a day, 10% emulsifiable concentrates (or 10% wettable powders) of compounds of the present invention were diluted with water containing a spreader to obtain 500 ppm solutions. The solutions were sprayed from a rotary spray tower (2.5 mg/cm$^2$), and the dishes were covered with lids and placed in an incubator at 25° C. 6 days after, dead insects were counted, and the mortality was calculated by using the same equation as in Test Example 1. The test was carried out in duplicate.

Among the compounds tested, the following compounds showed a mortality of at least 90%.

Compounds Nos. 1-1-001a, 1-1-002a, 1-1-002b, 1-1-004a, 1-1-005a, 1-1-006a, 1-1-006b, 1-1-007a, 1-1-008a, 1-1-010a, 1-1-011a, 1-1-012a, 1-1-012b, 1-1-013a, 1-1-014a, 1-1-015a, 1-1-016a, 1-1-016b, 1-1-017a, 1-2-001a, 1-2-002a, 1-10-001a and 1-11-001b of the present invention.

Test Example 6: Soil Irrigation Test on *Myzus persicae*

10% emulsifiable concentrates of compounds of the present invention were diluted with tap water to obtain 500 ppm solutions.

The soil around the bases of cabbage seedlings (at the 2.5-leaf stage) planted in plastic cups was irrigated with 10 ml of the solutions. After the irrigation, the cabbage seedlings were placed in a greenhouse. One day after the irrigation, adults of *Myzus persicae* were released at a ratio of 20 insects per seedling, and the seedlings were left in the greenhouse. 6 days after the release of the insects, living insects were counted, and the control value was calculated from the following equation.

Control value (%)={1−($Cb \times Tai$)/($Cai \times Tb$)}×100

Cb: the number of insects in a non-treated plot before treatment
Cai: the final number of living insects in a non-treated plot
Tb: the number of insects in a treated plot before treatment
Tai: the final number of living insects in a treated plot Among the compounds tested, the following compounds showed a control value of at least 90%.

Compounds Nos. 1-1-004a, 1-1-006a, 1-1-013a, 1-1-014a, 1-1-015a and 1-2-001a of the present invention.

Test Example 7: Systemic Insecticidal Test on *Nilaparvata lugens*

10% emulsifiable concentrates of compounds of the present invention were diluted with tap water to obtain 20 ppm solutions, and root of rice plug seedlings (at the 2-leaf stage) were dipped in the solutions. 7 days after, the rice seedlings were picked and put in test tubes, and in each tube, five 3rd-instar larvae of *Nilaparvata lugens* were released, and the tubes were capped with sponge and placed in an incubator at 25° C. 6 days after the release of the insects, dead insects were counted, the and the mortality was calculated by using the same equation as in Test Example 1. The test was carried out in duplicate.

Among the compounds tested, the following compounds showed a mortality of at least 90%.

Compounds Nos. 1-1-001a, 1-1-004a, 1-1-013a, 1-1-014a, 1-1-015a, 1-2-001a, 1-4-001a and 1-10-001a of the present invention.

Test Example 8: Soil Irrigation Test on *Plutella xylostella*

10% emulsifiable concentrates of compounds of the present invention were diluted with tap water to obtain 500 ppm solutions. The soil around the bases of cabbage seedlings (at the 2.5-leaf stage) planted in plastic cups was irrigated with 10 ml of the solutions. After the irrigation, the cabbage seedlings were placed in a greenhouse. 5 days after the irrigation, leaves of cabbage were picked and placed in dishes. In each dish, five 3rd-instar larvae of *Plutella xylostella* were released, and the dishes were covered with lids and placed in an incubator at 25° C. 6 days after, dead insects in the dishes were counted, and the control value was calculated by using the same equation as in Test Example 6. The test was carried out in duplicate.

Among the compounds tested, the following compounds showed a control value of at least 90%.

Compounds Nos. 1-1-001a, 1-1-002a, 1-1-004a, 1-1-005a, 1-1-006a, 1-1-013a, 1-1-014a, 1-1-015a, 1-2-001a, 1-4-001a and 1-10-001a of the present invention.

Test Example 9: Test on the Effect of Seed Treatment on *Aphis glycines*

2.4 mg of compounds of the present invention were diluted with 97.6 µl of acetone. Four soybean seeds were put in each 50 ml plastic tube, and the solutions of compounds of the present invention were poured onto the seeds and stirred until the acetone evaporated completely so that the seeds were evenly coated with the compounds. The treated seeds were sown in pots, 4 seeds per pot, and placed in a greenhouse. After the primary leaf folded out, two adults of *Aphis glycines* were released per seedling. 7 days after the release of the insects, living insects were counted, and the control value was calculated by using the same equation as in Test Example 6.

Among the compounds tested, the following compounds showed a control value of at least 90%.

Compounds Nos.: 1-1-004a, 1-1-006a, 1-1-013a, 1-1-014a, 1-1-015a and 1-2-001a of the present invention.

Test Example 10: Test on the Effect on *Rhipicephalus sanguineus*

3.5 mg of compounds of the present invention were diluted with 3.5 ml of acetone to obtain 1,000 ppm solutions. 350 µl of the solutions were applied to the bottoms and the side walls of glass containers with an inner wall surface area of 35 cm$^2$, and acetone was volatilized to prepare thin films of the compounds on the inner walls of the glass containers. Since the inner wall surface area of each glass container was 35 cm$^2$, the application dose was 10 µg/cm$^2$.

To each glass container, five protonymphs (male and female) of *Rhipicephalus sanguineus* were released, and the containers were covered with lids and placed in an incubator at 25° C. 4 days after the release of the ticks, dead ticks were counted, and the mortality was calculated by using the same equation as in Test Example 1.

Among the compounds tested, the following compounds showed a mortality of at least 50%.

Compounds Nos. 1-1-001a, 1-1-002a, 1-1-002b, 1-1-004a, 1-1-005a, 1-1-007a, 1-1-009a, 1-1-010a, 1-1-012a, 1-1-013a, 1-1-014a, 1-1-015a, 1-1-016a, 1-1-016b, 1-1-017a, 1-3-001a, 1-4-001a, 1-5-001a and 1-11-001a of the present invention.

Test Example 11: Test on the Effect on *Ctenocephalides felis*

3.5 mg of compounds of the present invention were diluted with 3.5 ml of acetone to obtain 1,000 ppm solutions.

350 µl of the solutions were applied to the bottoms and the side walls of glass containers with an inner wall surface area of 35 cm$^2$, and acetone was volatilized to prepare thin films of the compounds on the inner walls of the glass containers. Since the inner wall surface area of each glass container was 35 cm$^2$, the application dose was 10 µg/cm$^2$.

To each glass container, five adults (male and female) of *Ctenocephalides felis* were released, and the containers were covered with lids and placed in an incubator at 25° C. 4 days after the release of the fleas, dead fleas were counted, and the mortality was calculated by using the same equation as in Test Example 1.

Among the compounds tested, the following compounds showed a mortality of at least 50%.
Compounds Nos. 1-1-001a, 1-1-002a, 1-1-002b, 1-1-003a, 1-1-004a, 1-1-005a, 1-1-006a, 1-1-006b, 1-1-007a, 1-1-009a, 1-1-010a, 1-1-012a, 1-1-013a, 1-1-014a, 1-1-015a, 1-1-016a, 1-1-016b, 1-1-017a, 1-2-001a, 1-3-001a, 1-4-001a, 1-5-001a, 1-10-001a and 1-11-001a of the present invention.

Test Example 12: Test on the Parasiticidal Effect by Rat Oral Administration on *Rhipicephalus sanguineus*

5 mg of compounds of the present invention were dissolved in 5 ml of olive oil to prepare administration solutions. The solutions were orally administered to rats in a dose of 10 ml/kg body weight by a feeding tube. The oral administration was repeated twice in each group. 1 hour after the administration, 50 protonymphs (male and female) of *Rhipicephalus sanguineus* were released for each rat. 3 days after the release of the ticks, the number of ticks parasitic on the rats were counted, and the parasiticidal degree was calculated from the following equation.

Parasiticidal degree (%)=100×(1−the number of parasitic ticks on administered group/the number of parasitic ticks on non-administered group)

Among the compounds tested, the following compounds showed a parasiticidal degree of at least 70%.
Compounds Nos. 1-1-002a, 1-1-004a, 1-1-005a and 1-1-007a of the Present Invention.

Test Example 13: Insecticidal Test on *Musca domestica*

2 mg of compounds of the present invention were dissolved in 1 ml of acetone to prepare 2 µg/µl solutions. Female adults of *Musca domestica* were anesthetized with carbon dioxide gas, and 1 µl of the solutions were applied to thorax notum of the insects by a topical applicator (manufactured by Burkard Scientific Ltd.). After the application, the insects were put in plastic cups with lids having an inner diameter of 7.5 cm and a height of 4 cm, and the cups were placed in an incubator at 25° C. 3 days after, dead insects in the cups were counted, and the mortality was calculated by using the same equation as in Test Example 1. The test was carried out in duplicate with 5 insects.

Among the compounds tested, the following compounds showed a mortality of at least 70%.
Compounds Nos. 1-1-001a, 1-1-002a, 1-1-006a, 1-1-007a, 1-10-001a and 1-2-001a of the present invention.

Test Example 14: Insecticidal Test on *Blattela germanica*

2 mg of compounds of the present invention were dissolved in 0.2 ml of acetone to prepare 10 µg/µl solutions.

Male adults of *Blattela germanica* were anesthetized with carbon dioxide gas, and 1 µl of the solutions were applied to abdomens of the insects by a topical applicator (manufactured by Burkard Scientific Ltd.). After the application, the insects were put in deep dishes having an inner diameter of 6 cm and a height of 6 cm, and the dishes were placed in an incubator at 25° C. 3 days after, writhing insects and dead insects were counted, and the writhing/dead insects ratio (%) was calculated from the following equation. The test was carried out in quadruplicate with 5 insects.

Writhing/dead insects ratio (%)=(the number of writhing insects+the number of dead insects)/the number of insects tested×100

Among the compounds tested, the following compounds showed a writhing/dead insects ratio of at least 70%.
Compounds Nos. 1-1-001a, 1-1-002a, 1-10-001a and 1-2-001a of the Present Invention.

Test Example 15: Insecticidal Test on *Reticulitermes speratus*

10% emulsifiable concentrates of the compounds of the present invention were prepared. The emulsifiable concentrates were diluted with water to prepare 100 ppm solutions. 0.5 ml of the solutions were dropped on 10 g of river sand and mixed. In dishes having an inner diameter of 4 cm, 1% agar (2 cm square) was laid, and the treated river sand and a filter paper piece as bait were placed. Adults of *Reticulitermes speratus* were released in the dishes, and the dishes were placed in an incubator at 25° C. 10 days after, dead insects in the dishes were counted, and the mortality was calculated by using the same equation as in Test Example 1. The test was carried out in duplicate.

Among the compounds tested, the following compounds showed a mortality of at least 70%.
Compound Nos. 1-1-001a, 1-1-002a, 1-1-006a, 1-1-007a, 1-10-001a and 1-2-001a of the present invention.

Test Example 16: Insecticidal Test on *Culex pipiens* Molestus 2 mg of compounds of the present invention were dissolved in 0.2 ml of dimethyl sulfoxide to prepare 1% (w/v) dimethyl sulfoxide solutions. The solutions were diluted with distilled water by a factor of 100 to prepare 100 ppm solutions. To 1.9 ml plastic plates (Cellstar 24 well plate, manufactured by Greiner Bio-One International GmbH) as test plates, 0.7 ml of water containing 10 to 30 larvae of *Culex pipiens* molestus one day after hatching, and 0.2 ml of an aqueous suspension of aquarium fish food (TetraMin manufactured by Spectrum Brands Japan) as bait, were dropped. 0.1 ml of the 100 ppm solutions were dropped, and the plates were placed in an incubator at 25° C. 1 day after, dead larvae were counted, and the mortality was calculated by using the same equation as in Test Example 1. The test was carried out in duplicate.

Among the compounds tested, the following compounds showed a mortality of 100%.
Compound Nos. 1-1-001a, 1-1-002a, 1-1-006a and 1-1-007a of the Present Invention.

Test Example 17: Insecticidal Test on *Aedes albopictus*

2 mg of compounds of the present invention were dissolved in 0.2 ml of dimethyl sulfoxide to prepare 1% (w/v) dimethyl sulfoxide solutions. 0.01 ml of the solutions were mixed with 0.99 ml of pure water to prepare 0.01% (w/v) solutions. To 0.3 ml plastic plates (Cellstar 96 well culture plates, manufactured by Greiner Bio-One International GmbH) as test plates, 0.09 ml of distilled water containing 30 larvae of Aedes albopictus one day after hatching was dropped, and 0.01 ml of the 0.01% (w/v) solutions were dropped so that the final concentration would be 10 ppm. The plates were covered with lids and placed in an incubator at 25° C. 3 days after, dead larvae were counted, and the mortality was calculated by using the same equation as in Test Example 1.

Among the compounds tested, the following compounds showed a mortality of at least 70%.

Compound Nos. 1-1-001a, 1-1-002a, 1-1-003a, 1-1-004a, 1-1-005a, 1-1-006a, 1-1-006b, 1-1-007a, 1-1-010a, 1-1-011a, 1-1-013a, 1-1-016b, 1-2-001a, 1-2-002a, 1-2-002b, 1-3-001a, 1-4-001a, 1-5-001a, 1-11-001a and 1-11-001 b of the present invention.

INDUSTRIAL APPLICABILITY

The compounds of the present invention are very useful as novel pesticides which have excellent pesticidal activities, which have little harmful effect on non-target organisms such as mammals, fishes and useful insects, which have low toxicity, and which have low persistence.

The entire disclosures of the following Japanese Patent Applications including specification, claims, drawings and summary are incorporated herein by reference in their entireties.

JP-A-2016-047064 (Mar. 10, 2016)
JP-A-2016-054191 (Mar. 17, 2016)
JP-A-2016-199515 (Oct. 7, 2016)
JP-A-2016-255131 (Dec. 28, 2016)

The invention claimed is:

1. A condensed heterocyclic compound represented by the following formula (1) or its salt, or N-oxide thereof:

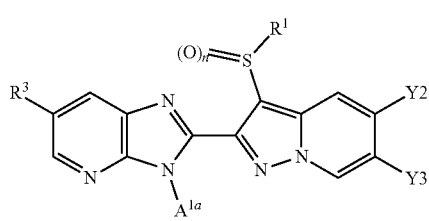

(1)

wherein $R^1$ is $C_1$-$C_6$ alkyl, $R^3$ is halo ($C_1$-$C_6$) alkyl, halo ($C_1$-$C_6$) alkylthio, halo ($C_1$-$C_6$) alkylsulfinyl or halo ($C_1$-$C_6$) alkylsulfonyl, each of Y2 and Y3 is independently a hydrogen atom, a halogen atom, or halo ($C_1$-$C_6$) alkyl, $A^{1a}$ is $C_1$-$C_6$ alkyl, and n is an integer of 0, 1 or 2.

2. The condensed heterocyclic compound or its salt, or N-oxide thereof according to claim 1, wherein $R^3$ is halo ($C_1$-$C_6$) alkyl, Y2 is a hydrogen atom, Y3 is a halogen atom, and n is an integer of 2.

3. A pesticide, comprising at least one condensed heterocyclic compound or its salt, or N-oxide thereof according to claim 1, as an active ingredient.

4. An agricultural chemical, comprising at least one condensed heterocyclic compound or its salt, or N-oxide thereof according to claim 1, as an active ingredient.

5. A parasiticide against internal or external parasites in or on a mammal or bird, comprising at least one condensed heterocyclic compound or its salt, or N-oxide thereof according to claim 1, as an active ingredient.

6. The parasiticide according to claim 5, wherein the external parasites are Siphonaptera or ticks.

7. An insecticide or acaricide, comprising at least one condensed heterocyclic compound or its salt, or N-oxide thereof according to claim 1, as an active ingredient.

8. A soil treatment agent, comprising at least one condensed heterocyclic compound or its salt, or N-oxide thereof according to claim 1, as an active ingredient.

9. A soil treatment method, comprising treating soil with the soil treatment agent according to claim 8 by irrigation.

10. A seed treatment agent, comprising at least one condensed heterocyclic compound or its salt, or N-oxide thereof according to claim 1, as an active ingredient.

11. A seed treatment method, comprising treating seeds with the seed treatment agent according to claim 10, by dipping.

* * * * *